(12) United States Patent
Baroudy et al.

(10) Patent No.: US 6,387,930 B1
(45) Date of Patent: May 14, 2002

(54) PIPERIDINE DERIVATIVES USEFUL AS CCR5 ANTAGONISTS

(75) Inventors: Bahige M. Baroudy, Westfield; John W. Clader, Cranford; Hubert B. Josien, Jersey City; Stuart W. McCombie, Caldwell; Brian A. McKittrick, Bloomfield; Michael W. Miller, Westfield; Bernard R. Neustadt, West Orange; Anandan Palani, Kenilworth; Ruo Steensma, Weehawken; Jayaram R. Tagat, Westfield; Susan F. Vice, Mountainside; Mark A. Laughlin, Edison, all of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/562,815

(22) Filed: May 1, 2000

Related U.S. Application Data

(60) Provisional application No. 60/132,510, filed on May 4, 1999.

(51) Int. Cl.⁷ .................... C07D 401/04; A61K 31/454; A61P 43/04

(52) U.S. Cl. .................. 514/316; 546/186; 546/187; 546/188; 546/191; 544/242; 544/336

(58) Field of Search ................ 546/191, 186, 546/187, 188; 514/316; 544/242, 336

(56) References Cited

U.S. PATENT DOCUMENTS

| | | | |
|---|---|---|---|
| 5,368,854 A | 11/1994 | Rennick | 424/85.2 |
| 5,883,096 A | 3/1999 | Lowe et al. | 514/852 |
| 5,889,006 A | 3/1999 | Lowe et al. | 544/215 |
| 5,952,349 A | 9/1999 | Asberom et al. | 514/316 |

(List continued on next page.)

FOREIGN PATENT DOCUMENTS

| | | |
|---|---|---|
| WO | WO 97/24324 | 7/1997 |
| WO | WO 98/01425 | 1/1998 |
| WO | WO 98/06697 | 2/1998 |
| WO | WO 99/04794 | 2/1999 |

OTHER PUBLICATIONS

Vandamme et al, *Antiviral Chemistry and Chemotherapy*, 9 (1998) pp. 187–203.
Conner et al, *Virology*, 206 (1995) pp. 935–944.

(List continued on next page.)

Primary Examiner—Mukund J. Shah
Assistant Examiner—Venkataraman Balasubramanian
(74) Attorney, Agent, or Firm—Anita W. Magatti

(57) ABSTRACT

The use of CCR5 antagonists of the formula

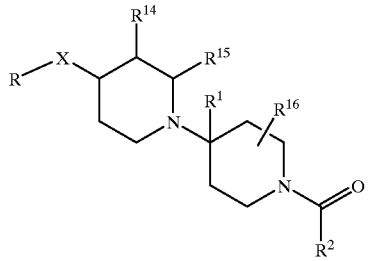

or a pharmaceutically acceptable salt thereof, wherein
X is $-C(R^{13})_2-$, $-C(R^{13})(R^{19})-$, $-C(O)-$, $-O-$, $-NH-$, $-N(alkyl)-$,

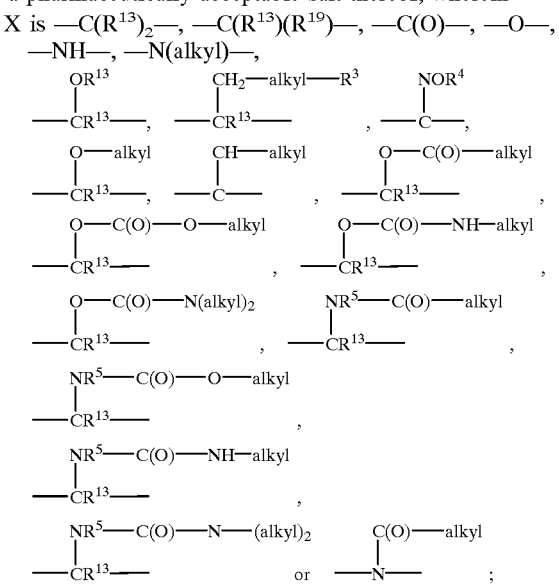

R is optionally substituted phenyl, pyridyl, thiophenyl or naphthyl;
$R^1$ is H, alkyl or alkenyl;
$R^2$ is optionally substituted phenyl, phenylalkyl, heteroaryl or heteroarylalkyl, naphthyl, fluorenyl or diphenylmethyl;
$R^3$ is optionally substituted phenyl, heteroaryl or naphthyl;
$R^4$ is H, alkyl, fluoro-alkyl, cyclopropylmethyl, $-CH_2CH_2OH$, $-CH_2CH_2-O$-alkyl, $-CH_2C(O)-$O-alkyl, $-CH_2C(O)NH_2$, $-CH_2C(O)-$NHalkyl or $-CH_2C(O)-N(alkyl)_2$;
$R^{19}$ is optionally substituted phenyl, heteroaryl or naphthyl, cycloalkyl, cycloalkylalkyl or alkoxyalkyl; and
$R^5$, $R^{13}$, $R^{14}$, $R^{15}$ and $R^{16}$ are hydrogen or alkyl for the treatment of HIV, solid organ transplant rejection, graft v. host disease, arthritis, rheumatoid arthritis, inflammatory bowel disease, atopic dermatitis, psoriasis, asthma, allergies or multiple sclerosis is disclosed, as well as novel compounds, pharmaceutical compositions comprising them, and the combination of CCR5 antagonists of the invention in combination with antiviral agents useful in the treatment of HIV or agents useful in the treatment of inflammatory diseases.

14 Claims, No Drawings

U.S. PATENT DOCUMENTS

| | | | |
|---|---|---|---|
| 5,977,138 A | 11/1999 | Wang et al. | 514/316 |
| 6,037,352 A | 3/2000 | Lowe et al. | 514/316 |

OTHER PUBLICATIONS

Plater–Zyberk et al, *Immunol. Let.*, 57 (1997) pp. 117–120.

Boiardi et al, *Clinical and Experimental Rheumatology*, 17 (1999) pp. 419–425.

Hatano et al, *Clin. Exp. Immunol.*, 117 (1999) pp. 237–243.

Raychaudhuri et al, International J. of *Immunopharmacology*, 20 (1998) pp. 661–667.

Chihara et al, *J. Allergy Clin. Immunol.*, 100, 6, part 2 (1997) pp. S52–S55.

Beck et al, *J. Immunol.*, 159, 6 (1997) pp. 2962–2972.

Chen et al, *Tet. Let.*, 37, 30 (1996) pp. 5233–5234.

PIPERIDINE DERIVATIVES USEFUL AS CCR5 ANTAGONISTS

CROSS REFERENCE TO RELATED APPLICATIONS

This application claims the benefit of U.S. Provisional Application 60/132,510, filed May 4, 1999.

BACKGROUND

The present invention relates to piperidine derivatives useful as selective CCR5 antagonists, pharmaceutical compositions containing the compounds, and methods of treatment using the compounds. The invention also relates to the use of a combination of a CCR5 antagonist of this invention and one or more antiviral or other agents useful in the treatment of Human Immunodeficiency Virus (HIV). The invention further relates to the use of a CCR-5 antagonist of this invention, alone or in combination with another agent, in the treatment of solid organ transplant rejection, graft v. host disease, arthritis, rheumatoid arthritis, inflammatory bowel disease, atopic dermatitis, psoriasis, asthma, allergies or multiple sclerosis.

The global health crisis caused by HIV, the causative agent of Acquired Immunodeficiency Syndrome (AIDS), is unquestioned, and while recent advances in drug therapies have been successful in slowing the progression of AIDS, there is still a need to find a safer, more efficient, less expensive way to control the virus.

It has been reported that the CCR5 gene plays a role in resistance to HIV infection. HIV infection begins by attachment of the virus to a target cell membrane through interaction with the cellular receptor CD4 and a secondary chemokine co-receptor molecule, and proceeds by replication and dissemination of infected cells through the blood and other tissue. There are various chemokine receptors, but for macrophage-tropic HIV, believed to be the key pathogenic strain that replicates in vivo in the early stages of infection, the principal chemokine receptor required for the entry of HIV into the cell is CCR5. Therefore, interfering with the interaction between the viral receptor CCR5 and HIV can block HIV entry into the cell. The present invention relates to small molecules which are CCR5 antagonists.

CCR-5 receptors have been reported to mediate cell transfer in inflammatory diseases such as arthritis, rheumatoid arthritis, atopic dermatitis, psoriasis, asthma and allergies, and inhibitors of such receptors are expected to be useful in the treatment of such diseases, and in the treatment of other inflammatory diseases or conditions such as inflammatory bowel disease, multiple sclerosis, solid organ transplant rejection and graft v. host disease.

Related piperidine derivatives which are muscarinic antagonists useful in the treatment of cognitive disorders such as Alzheimer's disease are disclosed in U.S. Pat. Nos. 5,883,096; 6,037,352; 5,889,006; 5,952,349; and 5,977,138.

A-M. Vandamme et al., *Antiviral Chemistry & Chemotherapy*, 9:187–203 (1998) disclose current clinical treatments of HIV-1 infections in man including at least triple drug combinations or so-called Highly Active Antiretroviral Therapy ("HAART"); HAART involves various combinations of nucleoside reverse transcriptase inhibitors ("NRTI"), non-nucleoside reverse transcriptase inhibitors ("NNRTI") and HIV protease inhibitors ("PI"). In compliant drug-naive patients, HAART is effective in reducing mortality and progression of HIV-1 to AIDS. However, these multidrug therapies do not eliminate HIV-1 and long-term treatment usually results in multidrug resistance. Development of new drug therapies to provide better HIV-1 treatment remains a priority.

SUMMARY OF THE INVENTION

The present invention relates to the treatment of HIV comprising administering to a human in need of such treatment an effective amount of a CCR5 antagonist represented by the structural formula I:

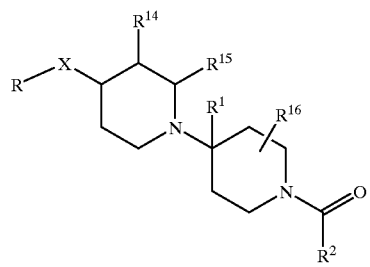

or a pharmaceutically acceptable salt thereof, wherein
X is —C($R^{13}$)$_2$—, —C($R^{13}$)($R^{19}$)—, —C(O)—, —O—, —NH—, —N(($C_1$–$C_6$)alkyl)—,

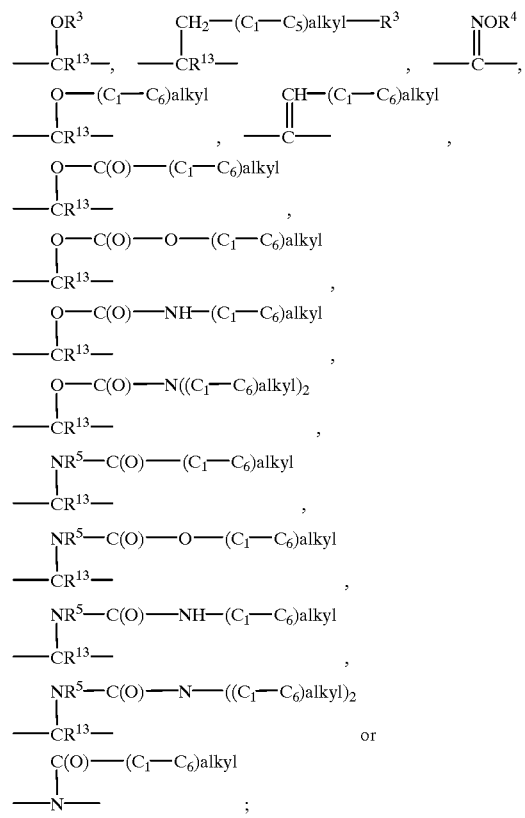

R is $R^6$-phenyl, $R^6$-pyridyl, $R^6$-thiophenyl or $R^6$-naphthyl;
$R^1$ is hydrogen, $C_1$–$C_6$ alkyl or $C_2$–$C_6$ alkenyl;
$R^2$ is $R^7$, $R^8$, $R^9$-phenyl; $R^7$, $R^8$, $R^9$-substituted 6-membered heteroaryl; $R^7$, $R^8$, $R^9$-substituted 6-membered heteroaryl N-oxide; $R^{10}$, $R^{11}$-substituted 5-membered heteroaryl; naphthyl; fluorenyl; diphenylmethyl

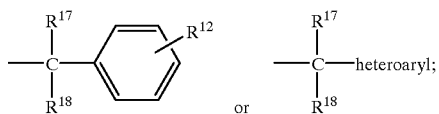

$R^3$ is $R^6$-phenyl, $R^6$-heteroaryl or $R^6$-naphthyl;

$R^4$ is hydrogen, $C_1$–$C_6$ alkyl, fluoro-$C_1$–$C_6$ alkyl, cyclopropylmethyl, —CH$_2$CH$_2$OH, —CH$_2$CH$_2$—O—($C_1$–$C_6$)alkyl, —CH$_2$C(O)—O—($C_1$–$C_6$)alkyl, —CH$_2$C(O)NH$_2$, —CH$_2$C(O)—NH($C_1$–$C_6$)alkyl or —CH$_2$C(O)—N(($C_1$–$C_6$)alkyl)$_2$;

$R^5$ and $R^{11}$ are independently selected from the group consisting of hydrogen and ($C_1$–$C_6$)-alkyl;

$R^6$ is 1 to 3 substituents independently selected from the group consisting of hydrogen, halogen, $C_1$–$C_6$ alkyl, $C_1$–$C_6$ alkoxy, —CF$_3$, CF$_3$O—, CH$_3$C(O)—, —CN, CH$_3$SO$_2$—, CF$_3$SO$_2$—, $R^{14}$-phenyl, $R^{14}$-benzyl, CH$_3$C(=NOCH$_3$)—, CH$_3$C(=NOCH$_2$CH$_3$)—,

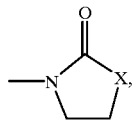

—NH$_2$, —NHCOCF$_3$, —NHCONH($C_1$–$C_6$ alkyl), —NHCO($C_1$–$C_6$ alkyl), —NHSO$_2$($C_1$–$C_6$ alkyl), 5-membered heteroaryl and

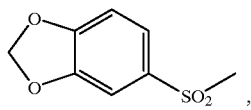

wherein X is —O—, —NH— or —N(CH$_3$)—;

$R^7$ and R8 are independently selected from the group consisting of ($C_1$–$C_6$)alkyl, halogen, —NR$^{20}$R$^{21}$, —OH, —CF$_3$, —OCH$_3$, —O-acyl, and —OCF$_3$;

$R^9$ is $R^7$, hydrogen, phenyl, —NO$_2$, —CN, —CH$_2$F, —CHF$_2$, —CHO, —CH=NOR$^{20}$, pyridyl, pyridyl N-oxide, pyrimidinyl, pyrazinyl, —N(R$^{20}$)CONR$^{21}$R$^{22}$, —NHCONH(chloro-($C_1$–$C_6$)alkyl), —NHCONH(($C_3$–$C_{10}$)-cycloalkyl($C_1$–$C_6$)alkyl), —NHCO($C_1$–$C_6$)alkyl, —NHCOCF$_3$, —NHSO$_2$N(($C_1$–$C_6$)alkyl)$_2$, —NHSO$_2$($C_1$–$C_6$)alkyl, —N(SO$_2$CF$_3$)$_2$, —NHCO$_2$($C_1$–$C_6$)alkyl, $C_3$–$C_{10}$ cycloalkyl, —SR$^{23}$, —SOR$^{23}$, —SO$_2$R$^{23}$, —SO$_2$NH($C_1$–$C_6$ alkyl), —OSO$_2$($C_1$–$C_6$)alkyl, —OSO$_2$CF$_3$, hydroxy($C_1$–$C_6$)alkyl, —CON R$^{20}$R$^{21}$, —CON(CH$_2$CH$_2$—O—CH$_3$)$_2$, —OCONH($C_1$–$C_6$)alkyl, —CO$_2$R$^{20}$, —Si(CH$_3$)$_3$ or —B(OC(CH$_3$)$_2$)$_2$;

$R^{10}$ is ($C_1$–$C_6$)alkyl, —NH$_2$ or $R^{12}$-phenyl;

$R^{12}$ is 1 to 3 substituents independently selected from the group consisting of hydrogen, ($C_1$–$C_6$) alkyl, —CF$_3$, —CO$_2$R$^{20}$, —CN, ($C_1$–$C_6$)alkoxy and halogen;

$R^{13}$, $R^{14}$, $R^{15}$ and $R^{16}$ are independently selected from the group consisting of hydrogen and ($C_1$–$C_6$)alkyl;

$R^{17}$ and $R^{18}$ are independently selected from the group consisting of hydrogen and $C_1$–$C_6$ alkyl, or $R^{17}$ and $R^{18}$ together are a $C_2$–$C_5$ alkylene group and with the carbon to which they are attached form a spiro ring of 3 to 6 carbon atoms;

$R^{19}$ is $R^6$-phenyl, $R^6$-heteroaryl, $R^6$-naphthyl, $C_3$–$C_{10}$ cycloalkyl, ($C_3$–$C_{10}$)cycloalkyl($C_1$–$C_6$)alkyl or ($C_1$–$C_6$)alkoxy($C_1$–$C_6$)alkyl;

$R^{20}$, $R^{21}$ and $R^{22}$ are independently selected from the group consisting of H and $C_1$–$C_6$ alkyl; and $R^{23}$ is $C_1$–$C_6$ alkyl or phenyl.

Preferred are compounds of formula I wherein R is $R^6$-phenyl, especially wherein $R^6$ is a single substituent, and especially wherein the $R^6$ substituent is in the 4-position. Also preferred are compounds of formula I wherein $R^{13}$, $R^{14}$, $R^{15}$ and $R^{16}$ are each hydrogen or methyl, especially hydrogen. Also preferred are compounds of formula I wherein X is —CHOR$^3$, —C(R$^{13}$)(R$^{19}$)— or —C(=NOR$^4$)—; a preferred definition for $R^3$ is pyridyl, especially 2-pyridyl, a preferred definition for $R^4$ is ($C_1$–$C_6$) alkyl, especially methyl, ethyl or isopropyl, a preferred definition for $R^{13}$ is hydrogen, and a preferred definition for $R^{19}$ is $R^6$-phenyl. For compounds of formula I, $R^1$ is preferably ($C_1$–$C_6$)alkyl, especially methyl.

In compounds of formula I, $R^2$ is preferably $R^7$, $R^8$, $R^9$-phenyl, $R^7$, $R^8$, $R^9$-pyridyl or an N-oxide thereof, or $R^7$, $R^8$, $R^9$-pyrimidyl. When $R^2$ is pyridyl, it is preferably 3- or 4-pyridyl, and when pyrimidyl, it is preferably 5-pyrimidyl. The $R^7$ and $R^8$ substituents are preferably attached to carbon ring members adjacent to the carbon joining the ring to the rest of the molecule and the $R^9$ substituent can be attached to any of the remaining unsubstituted carbon ring members, for example as shown in the following structures:

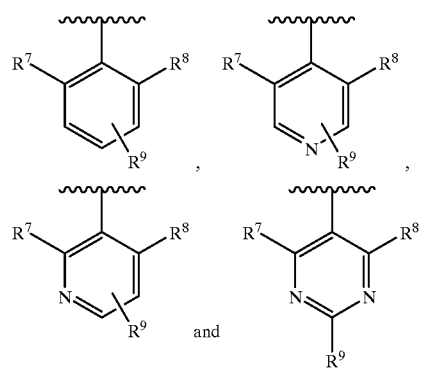

Preferred $R^7$ and $R^8$ substituents are: ($C_1$–$C_6$)alkyl, especially methyl; halogen, especially chloro; and —NH$_2$. A preferred $R^9$ substituent is hydrogen.

Also claimed are novel CCR5 antagonist compounds represented by the structural formula II

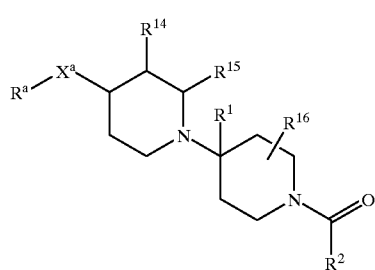

or a pharmaceutically acceptable salt thereof, wherein (1) $X^a$ is —C(R$^{13}$)$_2$—, —C(R$^{13}$)(R$^{19}$)—, —C(O)—, —O—, —NH—, —N(($C_1$–$C_6$)alkyl)—,

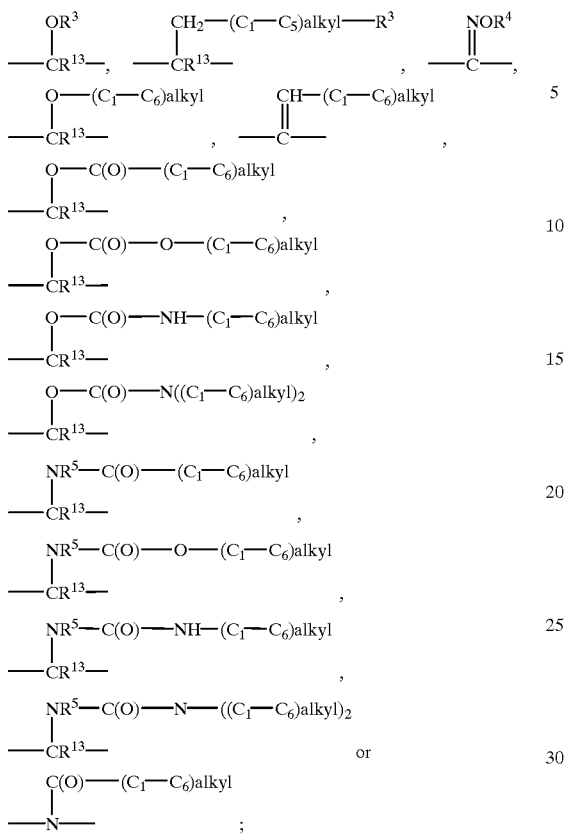

$R^a$ is $R^{6a}$-phenyl, $R^{6a}$-pyridyl, $R^{6a}$-thiophenyl or $R^6$-naphthyl;

$R^1$ is hydrogen, $C_1$–$C_6$ alkyl or $C_2$–$C_6$ alkenyl;

$R^2$ is $R^7$, $R^8$, $R^9$-phenyl; $R^7$, $R^8$, $R^9$-substituted 6-membered heteroaryl; $R^7$, $R^8$, $R^9$-substituted 6-membered heteroaryl N-oxide; $R^{10}$, $R^{11}$-substituted 5-membered heteroaryl; naphthyl; fluorenyl; diphenylmethyl $R^3$ is $R^{10}$-phenyl, pyridyl, pyrimidyl, pyrazinyl or thiazolyl;

$R^4$ is hydrogen, $C_1$–$C_6$ alkyl, fluoro-$C_1$–$C_6$ alkyl, cyclopropylmethyl, —$CH_2CH_2OH$, —$CH_2CH_2$—O—($C_1$–$C_6$)alkyl, —$CH_2C(O)$—O—($C_1$–$C_6$)alkyl, —$CH_2C(O)NH_2$, —$CH_2C(O)$—NH($C_1$–$C_6$)alkyl or —$CH_2C(O)$—N(($C_1$–$C_6$)alkyl)$_2$;

$R^5$ and $R^{11}$ are independently selected from the group consisting of hydrogen and ($C_1$–$C_6$)-alkyl;

$R^{6a}$ is 1 to 3 substituents independently selected from the group consisting of hydrogen, halogen, —$CF_3$, $CF_3O$—, —CN, —$CF_3SO_2$—, $R^{12}$-phenyl, —$NHCOCF_3$, 5-membered heteroaryl and wherein X is —O—, —NH— or —N($CH_3$)—;

$R^6$ is independently selected from the group consisting of $R^{6a}$ and $CH_3SO_2$—;

$R^7$ and $R^8$ are independently selected from the group consisting of ($C_1$–$C_6$)alkyl, halogen, —$NR^{20}R^{21}$, —OH, —$CF_3$, —$OCH_3$, —O-acyl, and —$OCF_3$;

$R^9$ is $R^7$, hydrogen, phenyl, —$NO_2$, —CN, —$CH_2F$, —$CHF_2$, —CHO, —CH=$NOR^{20}$, pyridyl, pyridyl N-oxide, pyrimidinyl, pyrazinyl, —N($R^{20}$)$CONR^{21}R^{22}$, —NHCONH(chloro-($C_1$–$C_6$)alkyl), —NHCONH((($C_3$–$C_{10}$)-cycloalkyl($C_1$–$C_6$)alkyl), —NHCO($C_1$–$C_6$)alkyl, —$NHCOCF_3$, —$NHSO_2N$(($C_1$–$C_6$)alkyl)$_2$, —$NHSO_2$($C_1$–$C_6$)alkyl, —N($SO_2CF_3$)$_2$, —$NHCO_2$($C_1$–$C_6$)alkyl, $C_3$–$C_{10}$ cycloalkyl, —$SR^{23}$, -$SOR^{23}$, —$SO_2R^{23}$, —$SO_2NH$($C_1$–$C_6$ alkyl), —$OSO_2$($C_1$–$C_6$)alkyl, —$OSO_2CF_3$, hydroxy($C_1$–$C_6$)alkyl, —CON $R^{20}R^{21}$, —CON($CH_2CH_2$—O—$CH_3$)$_2$, —OCONH($C_1$–$C_6$)alkyl, —$CO_2R^{20}$, —Si($CH_3$)$_3$ or —B(OC($CH_3$)$_2$)$_2$;

$R^{10}$ is ($C_1$–$C_6$)alkyl, —$NH_2$ or $R^{12}$-phenyl;

$R^{12}$ is 1 to 3 substituents independently selected from the group consisting of hydrogen, ($C_1$–$C_6$) alkyl, —$CF_3$, —$CO_2R_{20}$, —CN, ($C_1$–$C_6$)alkoxy and halogen;

$R^{13}$, $R^{14}$, $R^{15}$ and $R^{16}$ are independently selected from the group consisting of hydrogen and ($C_1$–$C_6$)alkyl;

$R^{17}$ and $R^{18}$ are independently selected from the group consisting of hydrogen and $C_1$–$C_6$ alkyl, or $R^{17}$ and $R^{18}$ together are a $C_2$–$C_5$ alkylene group and with the carbon to which they are attached form a spiro ring of 3 to 6 carbon atoms;

$R^{19}$ is $R^6$-phenyl, $R^6$-heteroaryl, $R^6$-naphthyl, $C_3$–$C_{10}$ cycloalkyl, ($C_3$–$C_{10}$)cycloalkyl($C_1$–$C_6$)alkyl or ($C_1$–$C_6$)alkoxy($C_1$–$C_6$)alkyl;

$R^{20}$, $R^{21}$ and $R^{22}$ are independently selected from the group consisting of H and $C_1$–$C_6$ alkyl; and $R^{23}$ is $C_1$–$C_6$ alkyl or phenyl; or (2): $X^a$ is —$C(R^{13})(R^{19})$—, —C(O)—, —O—, —NH—, —N(($C_1$–$C_6$)alkyl)—, -continued

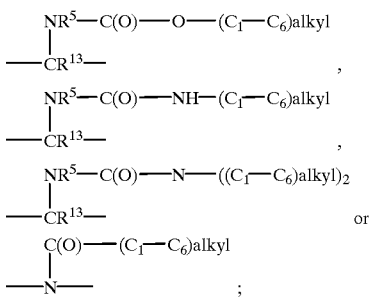

R$^a$ is R$^{6b}$-phenyl, R$^{6b}$-pyridyl or R$^{6b}$-thiophenyl;
R$^{4a}$ is fluoro-C$_1$–C$_6$ alkyl, cyclopropylmethyl, —CH$_2$CH$_2$OH, —CH$_2$CH$_2$—O—(C$_1$–C$_6$)alkyl, —CH$_2$C(O)—O—(C$_1$–C$_6$)alkyl, —CH$_2$C(O)NH$_2$, —CH$_2$C(O)—NH—(C$_1$–C$_6$)alkyl or —CH$_2$C(O)—N((C$_1$–C$_6$)alkyl)$_2$;
R$^{6b}$ is CH$_3$SO$_2$—; and
R$^1$, R$^2$, R$^3$, R$^5$, R$^{14}$, R$^{15}$, R$^{16}$ and R$^{19}$ are as defined in (1).

Preferred are compounds of formula II(1) wherein R$^a$ is R$^{6a}$-phenyl, especially wherein R$^{6a}$ is a single substituent, and especially wherein the R$^{6a}$ substituent is in the 4-position. Also preferred are compounds of formula II(1) wherein X$^a$ is —CHOR$^3$, —C(R$^{13}$)(R$^{19}$)— or —C(=NOR$^4$)—; a preferred definition for R$^3$ is pyridyl, especially 2-pyridyl, a preferred definition for R$^4$ is (C$_1$–C$_6$) alkyl, especially methyl, ethyl or isopropyl, a preferred definition for R$^{13}$ is hydrogen, and a preferred definition for R$^{19}$ is R$^6$-phenyl. For compounds of formula II(1), R$^1$ is preferably (C$_1$–C$_6$)alkyl, Preferred are compounds of formula II(2) wherein R$^a$ is R$^{6b}$-phenyl, especially wherein R$^{6b}$ is a single substituent, and especially wherein the R$^{6b}$ substituent is in the 4-position. Also preferred are compounds of formula II(2) wherein X$^a$ is —CHOR$^3$, —C(R$^{13}$)(R$^{19}$)— or C(=NOR$^{4a}$)—; a preferred definition for R$^3$ is pyridyl, especially 2-pyridyl, preferred definitions for R$^{4a}$ are cyclopropylmethyl and trifluoroethyl, a preferred definition for R$^{13}$ is hydrogen, and a preferred definition for R$^{19}$ is R$^6$-phenyl. For compounds of formula II(2), R$^1$ is preferably (C$_1$–C$_6$)alkyl, especially methyl. Also for compounds of formula II(2), R$^{14}$, R$^{15}$ and R$^{16}$ are preferably hydrogen.

In compounds of formula II(1) and (2), R$^2$ is preferably R$^7$, R$^8$, R$^9$-phenyl; R$^7$, R$^8$, R$^9$-pyridyl or an N-oxide thereof; or R$^7$, R$^8$, R$^9$-pyrimidyl. When R$^2$ is pyridyl, it is preferably 3- or 4-pyridyl, and when pyrimidyl, it is preferably 5-pyrimidyl. The R$^7$ and R$^8$ substituents are preferably attached to carbon ring members adjacent to the carbon joining the ring to the rest of the molecule and the R$^9$ substituent can be attached to any of the remaining unsubstituted carbon ring members as shown above for compounds of formula I. Preferred R$^7$ and R$^8$ substituents for compounds of formula II are: (C$_1$–C$_6$)alkyl, especially methyl; halogen, especially chloro; and —NH$_2$; a preferred R$^9$ substituent is hydrogen.

Another aspect of the invention is a pharmaceutical composition for treatment of HIV comprising an effective amount of a CCR5 antagonist of formula II in combination with a pharmaceutically acceptable carrier. Another aspect of the invention is a pharmaceutical composition for treatment of solid organ transplant rejection, graft v. host disease, arthritis, rheumatoid arthritis, inflammatory bowel disease, atopic dermatitis, psoriasis, asthma, allergies or multiple sclerosis comprising an effective amount of a CCR5 antagonist of formula II in combination with a pharmaceutically acceptable carrier.

Yet another aspect of this invention is a method of treatment of HIV comprising administering to a human in need of such treatment an effective amount of a CCR5 antagonist compound of formula II. Another aspect of the invention is a method of treatment of solid organ transplant rejection, graft v. host disease, arthritis, rheumatoid arthritis, inflammatory bowel disease, atopic dermatitis, psoriasis, asthma, allergies or multiple sclerosis comprising administering to a human in need of such treatment an effective amount of a CCR5 antagonist compound of formula I or II. comprising administering to a human in need of such treatment an effective amount of a CCR5 antagonist compound of formula I or II.

Still another aspect of this invention is the use of a CCR5 antagonist of formula I or II of this invention in combination with one or more antiviral or other agents useful in the treatment of Human Immunodeficiency Virus for the treatment of AIDS. Still another aspect of this invention is the use of a CCR5 antagonist of formula I or II of this invention in combination with one or more other agents useful in the treatment of solid organ transplant rejection, graft v. host disease, inflammatory bowel disease, rheumatoid arthritis or multiple sclerosis. The CCR5 and antiviral or other agents which are components of the combination can be administered in a single dosage form or they can be administered separately; a kit comprising separate dosage forms of the actives is also contemplated.

DETAILED DESCRIPTION OF THE INVENTION

As used herein, the following terms are used as defined below unless otherwise indicated.

Alkyl (including the alkyl portions of alkoxy, alkylamino and dialkylamino) represents straight and branched carbon chains and contains from one to six carbon atoms.

Alkenyl represents C$_2$–C$_6$ carbon chains having one or two unsaturated bonds, provided that two unsaturated bonds are not adjacent to each other.

Substituted phenyl means that the phenyl group can be substituted at any available position on the phenyl ring.

Acyl means a radical of a carboxylic acid having the formula alkyl-C(O)—, aryl-C(O)—, aralkyl-C(O)—, (C$_3$–C$_7$)cycloalkyl-C(O)—, (C$_3$–C$_7$)cycloalkyl-(C$_1$–C$_6$) alkyl-C(O)—, and heteroaryl-C(O)—, wherein alkyl and heteroaryl are as defined herein; aryl is R$^{12}$-phenyl or R$^{12}$-naphthyl; and aralkyl is aryl-(C$_1$–C$_6$)alkyl, wherein aryl is as defined above.

Heteroaryl represents cyclic aromatic groups of 5 or 6 atoms or bicyclic groups of 11 to 12 atoms having 1 or 2 heteroatoms independently selected from O, S or N, said heteroatom(s) interrupting a carbocyclic ring structure and having a sufficient number of delocalized pi electrons to provide aromatic character, provided that the rings do not contain adjacent oxygen and/or sulfur atoms. For 6-membered heteroaryl rings, carbon atoms can be substituted by R$^7$, R$^8$ or R$^9$ groups. Nitrogen atoms can form an N-oxide. All regioisomers are contemplated, e.g., 2-pyridyl, 3-pyridyl and 4-pyridyl. Typical 6-membered heteroaryl groups are pyridyl, pyrimidinyl, pyrazinyl, pyridazinyl and the N-oxides thereof. For 5-membered heteroaryl rings, carbon atoms d(an be substituted by R$^{10}$ or R$^{11}$ groups. Typical 5-membered heteroaryl rings are furyl, thienyl, pyrrolyl, thiazolyl, isothiazolyl, imidazolyl, pyrazolyl and isoxazolyl. 5-Membered rings having one heteroatom can be joined through the 2- or 3-position; 5-membered rings having two heteroatoms are preferably joined through the 4-position. Bicyclic groups typically are benzo-fused ring systems derived from the heteroaryl groups named above, e.g. quinolyl, phthalazinyl, quinazolinyl, benzofuranyl, benzothienyl and indolyl.

Preferred points of substitution for 6-membered heteroaryl rings at $R^2$ are described above. When $R^2$ is a 5-membered heteroaryl group, the $R^{10}$ and $R^{11}$ substituents are preferably attached to carbon ring members adjacent to the carbon joining the ring to the rest of the molecule, and $R^{11}$ is preferably alkyl; however, if a heteroatom is adjacent to the carbon joining the ring to the rest of the molecule (i.e., as in 2-pyrrolyl), $R^{10}$ is preferably attached to a carbon ring member adjacent to the carbon joining the ring to the rest of the molecule.

Halogen represents fluoro, chloro, bromo and iodo.

Fluoro($C_1$–$C_6$)alkyl represents a straight or branched alkyl chain substituted by 1 to 5 fluoro atoms, which can be attached to the same or different carbon atoms, e.g., —$CH_2F$, —$CHF_2$, —$CF_3$, $F_3CCH_2$— and —$CF_2CF_3$.

A therapeutically effective amount of a CCR5 antagonist is an amount sufficient to lower HIV-1-RNA plasma levels.

One or more, preferably one to four, antiviral agents useful in anti-HIV-1 therapy may be used in combination with a CCR5 antagonist of the present invention. The antiviral agent or agents may be combined with the CCR5 antagonist in a single dosage form, or the CCR5 antagonist and the antiviral agent or agents may be administered simultaneously or sequentially as separate dosage forms. The antiviral agents contemplated for use in combination with the compounds of the present invention comprise nucleoside and nucleotide reverse transcriptase inhibitors, non-nucleoside reverse transcriptase inhibitors, protease inhibitors and other antiviral drugs listed below not falling within these classifications. In particular, the combinations known as HMRT are contemplated for use in combination with the CCR5 antagonists of this invention.

The term "nucleoside and nucleotide reverse transcriptase inhibitors" ("NRTI" s) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA.

Typical suitable NRTIs include zidovudine (AZT) available under the RETROVIR tradename from Glaxo-Welicome Inc., Research Triangle, N.C. 27709; didanosine (ddI) available under the VIDEX tradename from Bristol-Myers Squibb Co., Princeton, N.J. 08543; zalcitabine (ddC) available under the HIVID tradename from Roche Pharmaceuticals, Nutley, N.J. 07110; stavudine (d4T) available under the ZERIT trademark from Bristol-Myers Squibb Co., Princeton, N.J. 08543; lamivudine (3TC) available under the EPIVIR tradename from Glaxo-Wellcome Research Triangle, N.C. 27709; abacavir (1592U89) disclosed in WO96/30025 and available under the ZIAGEN trademark from Glaxo-Wellcome Research Triangle, N.C. 27709; adefovir dipivoxil [bis(POM)-PMEA] available under the PREVON tradename from Gilead Sciences, Foster City, Calif. 94404; lobucavir (BMS-180194), a nucleoside reverse transcriptase inhibitor disclosed in EP-0358154 and EP-0736533 and under development by Bristol-Myers Squibb, Princeton, N.J. 08543; BCH-10652, a reverse transcriptase inhibitor (in the form of a racemic mixture of BCH-10618 and BCH-10619) under development by Biochem Pharma, Laval, Quebec $H_7V$, 4A7, Canada; emitricitabine [(−)-FTC] licensed from Emory University under Emory Univ. U.S. Pat. No. 5,814,639 and under development by Triangle Pharmaceuticals, Durham, N.C. 27707; beta-L-FD4 (also called beta-L-D4C and named beta-L-2', 3'-dicleoxy-5-fluoro-cytidene) licensed by Yale University to Vion Pharmaceuticals, New Haven Conn. 06511; DAPD, the purine nucleoside, (−)-beta-D-2,6,-diamino-purine dioxolane disclosed in EP 0656778 and licensed by Emory University and the University of Georgia to Triangle Pharmaceuticals, Durham, N.C. 27707; and lodenosine (FddA), 9-(2,3-dideoxy-2-fluoro-b-D-threo-pentofuranosyl) adenine, an acid stable purine-based reverse transcriptase inhibitor discovered by the NIH and under development by U.S. Bioscience Inc., West Conshohoken, Pa. 19428.

The term "non-nucleoside reverse transcriptase inhibitors" ("NNRTI"s) as used herein means non-nucleosides that inhibit the activity of HIV-1 reverse transcriptase.

Typical suitable NNRTIs include nevirapine (BI-RG-587) available under the VIRAMUNE tradename from Boehringer Ingelheim, the manufacturer for Roxane Laboratories, Columbus, Ohio 43216; delaviradine (BHAP, U-90152) available under the RESCRIPTOR tradename from Pharmacia & Upjohn Co., Bridgewater N.J. 08807; efavirenz (DMP-266) a benzoxazin-2-one disclosed in WO94/03440 and available under the SUSTIVA tradename from DuPont Pharmaceutical Co., Wilmington, Del. 19880–0723; PNU-142721, a furopyridine-thio-pyrimide under development by Pharmacia and Upjohn, Bridgewater N.J. 08807; AG-1549 (formerly Shionogi #S-1153); 5-(3,5-dichlorophenyl)-thio-4-isopropyl-1-(4-pyridyl)methyl-1H-imidazol-2-ylmethyl carbonate disclosed in WO 96/10019 and under clinical development by Agouron Pharmaceuticals, Inc., LaJolla Calif. 92037–1020; MKC-442 (1-(ethoxy-methyl)-5-(1-methylethyl)-6-(phenylmethyl)-(2,4(1H,3H)-pyrimidinedione) discovered by Mitsubishi Chemical Co. and under development by Triangle Pharmaceuticals, Durham, N.C. 27707; and (+)-calanolide A (NSC-675451) and B, coumarin derivatives disclosed in NIH U.S. Pat. No. 5,489,697, licensed to Med Chem Research, which is co-developing (+) calanolide A with Vita-Invest as an orally administrable product.

The term "protease inhibitor" ("PI") as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character, e.g. CRIXIVAN(available from Merck) as well as nonpeptide protease inhibitors e.g., VIRACEPT (available from Agouron).

Typical suitable PIs include saquinavir (Ro 31-8959) available in hard gel capsules under the INVIRASE tradename and as soft gel capsules under the FORTOVASE tradename from Roche Pharmaceuticals, Nutley, N.J. 07110-1199; ritonavir (ABT-538) available under the NORVIR tradename from Abbott Laboratories, Abbott Park, Ill. 60064; indinavir (MK-639) available under the CRIXIVAN tradename from Merck & Co., Inc., West Point, Pa. 19486-0004; nelfnavir (AG-1343) available under the VIRACEPT tradename from Agouron Pharmaceuticals, Inc., LaJolla Calif. 92037-1020; amprenavir (141W94), tradename AGENERASE, a non-peptide protease inhibitor under development by Vertex Pharmaceuticals, Inc., Cambridge, Mass. 02139-4211 and available from Glaxo-Wellcome, Research Triangle, N.C. under an expanded access program; lasinavir (BMS-234475) available from Bristol-Myers Squibb, Princeton, N.J. 08543 (originally discovered by Novartis, Basel, Switzerland (CGP-61755); DMP-450, a cyclic urea discovered by Dupont and under development by Triangle Pharmaceuticals; BMS-2322623, an azapeptide under development by Bristol-Myers Squibb, Princeton, N.J. 08543, as a 2nd-generation HIV-1 PI; ABT-378 under development by Abbott, Abbott Park, Ill. 60064; and AG-1549 an orally active imidazole carbamate discovered by Shionogi (Shionogi #S-1153) and under development by Agouron Pharmaceuticals, Inc., LaJolla Calif. 92037-1020.

Other antiviral agents include hydroxyurea, ribavirin, IL-2, IL-12, pentafuside and Yissum Project No.11607. Hydroyurea (Droxia), a ribonucleoside triphosphate reductase inhibitor, the enzyme involved in the activation of T-cells, was discovered at the NCI and is under development by Bristol-Myers Squibb; in preclinical studies, it was shown to have a synergistic effect on the activity of didanosine and has been studied with stavudine. IL-2 is disclosed in Ajinomoto EP-0142268, Takeda EP-0176299, and Chiron U.S. Pat. Nos. RE 33,653, 4,530,787, 4,569,790, 4,604,377, 4,748,234, 4,752,585, and 4,949,314, and is available under the PROLEUKIN (aldesleukin) tradename from Chiron Corp., Emeryville, Calif. 94608-2997 as a lyophilized powder for IV infusion or sc administration upon reconstitution and dilution with water; a dose of about 1 to about 20 million IU/day, sc is preferred; a dose of about 15 million IU/day, sc is more preferred. IL-12 is disclosed in WO96/25171 and is available from Roche Pharmaceuticals, Nutley, N.J. 07110-1199 and American Home Products, Madison, N.J. 07940; a dose of about 0.5 microgram/kg/day to about 10 microgram/kg/day, sc is preferred. Pentafuside (DP-178, T-20) a 36-amino acid synthetic peptide, disclosed in U.S. Pat. No. 5,464,933 licensed from Duke University to Trimeris which is developing pentafuside in collaboration with Duke University; pentafuside acts by inhibiting fusion of HIV-1 to target membranes. Pentafuside (3–100 mg/day) is given as a continuous sc infusion or injection together with efavirenz and 2 PI's to HIV-1 positive patients refractory to a triple combination therapy; use of 100 mg/day is preferred. Yissum Project No. 11607, a synthetic protein based on the HIV-1 Vif protein, is under preclinical development by Yissum Research Development Co., Jerusalem 91042, Israel. Ribavirin, 1-β-D-ribofuranosyl-1H-1,2,4-triazole-3-carboxamide, is available from ICN Pharmaceuticals, Inc., Costa Mesa, Calif; its manufacture and formulation are described in U.S. Pat. No. 4,211,771.

The term "anti-HIV-1 therapy" as used herein means any anti-HIV-1 drug found useful for treating HIV-1 infections in man alone, or as part of multidrug combination therapies, especially the HAART triple and quadruple combination therapies. Typical suitable known anti-HIV-1 therapies include, but are not limited to multidrug combination therapies such as (i) at least three anti-HIV-1 drugs selected from two NRTIs, one PI, a second PI, and one NNRTI; and (ii) at least two anti-HIV-1 drugs selected from NNRTIs and PIs. Typical suitable HAART—multidrug combination therapies include:

(a) triple combination therapies such as two NRTIs and one PI; or (b) two NRTIs and one NNRTI; and (c) quadruple combination therapies such as two NRTIs, one PI and a second PI or one NNRTI. In treatment of naive patients, it is preferred to start anti-HIV-1 treatment with the triple combination therapy; the use of two NRTIs and one PI is prefered unless there is intolerance to PIs. Drug compliance is essential. The CD4[+] and HIV-1-RNA plasma levels should be monitored every 3–6 months. Should viral load plateau, a fourth drug, e.g., one PI or one NNRTI could be added. See the table below wherein typical therapies are further described:

ANTI-HIV-1 MULTI DRUG COMBINATION THERAPIES

A. Triple Combination Therapies
1. Two NRTIs[1]+one PI[2]
2. Two NRTIs[1]+one NNRTI[3]
B. Quadruple Combination Therapies[4]
   Two NRTIs+one PI+a second PI or one NNRTI
C. ALTERNATIVES:[5]
   Two NRTI[1]
   One NRTI[5]+one PI[2]
   Two PIs[6]±one NRTI[7] or NNRTI[3]
   One PI[2]+one NRTI[7]+one NNRTI[3]

FOOTNOTES TO TABLE

1. One of the following: zidovudine+lamivudine; zidovudine+didanosine; stavudine+lamivudine; stavudine+didanosine; zidovudine+zalcitabine
2. Indinavir, nelfinavir, ritonavir or saquinavir soft gel capsules.
3. Nevirapine or delavirdine.
4. See A-M. Vandamne et al Antiviral Chemistry & Chemotherapy 9:187 at p 193–197 and FIGS. 1+2. who fail or relapse on a recommended regimen. Double nucleoside combinations may lead to HIV-resistance and clinical failure in many patients.
6. Most data obtained with saquinavir and ritonavir (each 400 mg bid).
7. Zidovudine, stavudine or didanosine.

Agents known in the treatment of rheumatoid arthritis, transplant and graft v. host disease, inflammatory bowel disease and multiple sclerosis which can be administered in combination with the CCR5 antagonists of the present invention are as follows:

solid organ transplant rejection and graft v. host disease: immune suppressants such as cyclosporine and Interleukin-10 (IL-10), tacrolimus, a antilymphocyte globulin, OKT-3 antibody, and steroids;

inflammatory bowel disease: IL-10 (see U.S. Pat. No. 5,368,854), steroids and azulfidine;

rheumatoid arthritis: methotrexate, azathioprine, cyclophosphamide, steroids and mycophenolate mofetil;

multiple sclerosis: interferon-beta, interferon-alpha, and steroids.

Certain CCR5 antagonist compounds of the invention may exist in different isomeric (e.g., enantiomers, diastereoisomers and atropisomers) forms. The invention contemplates all such isomers both in pure form and in admixture, including racemic mixtures.

Certain compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Compounds of the invention can be made by the procedures known in the art, for example by the procedures described in the following reaction schemes, by the methods described in the examples below, and by using the methods described in U.S. Pat. Nos. 5,883,096; 6,037,352; 5,889,006; 5,952,349; and 5,977,138.

The following solvents and reagents may be referred to herein by the abbreviations indicated: tetrahydrofuran (THF); ethanol (EtOH); methanol (MeOH); acetic acid (HOAC or ACOH); ethyl acetate (EtOAc); N,N-dimethylformamide (DMF); trifluoroacetic acid (TFA); trifluoroacetic anhydride (TFAA); 1-hydroxy-benzotriazole (HOBT); m-chloroperbenzoic acid (MCPBA); triethylamine ($Et_3N$); diethyl ether ($Et_2O$); tert-butoxycarbonyl (BOC); 1,8-diazabicyclo[5.4.0]undec-7-ene (DBU); dimethylsulfoxide (DMSO); p-toluene sulfonic acid (p-TSA); potassium bis(trimethylsilyl)-amide (KHMDA); 4-dimethylaminopryidine (DMAP); N,N,N-diiospropylethylamine (Dipea); and 1-(3-dimethylaminopropyl)-3-ethyl carbodiimide hydrochloride (DEC). RT is room temperature.

Compounds of formula I and II wherein X is CHO (C=O)—($C_1$-$C_6$)-alkyl, CHO(C=O)—($C_1$-$C_6$)alkoxy, CHO(C=O)—NH—($C_1$-$C_6$)alkyl, $CHNR^5$(C=O)—($C_1$-$C_6$)alkyl, $CHNR^5$(C=O)—($C_1$-$C_6$)alkoxy, $CHNR^5$(C=O)—NH—($C_1$-$C_6$)alkyl or —$CHOR^3$ (and wherein $R^{14}$, $R^{15}$ and $R^{16}$ are hydrogen) are prepared according to Schemes 1–4:

Scheme 1

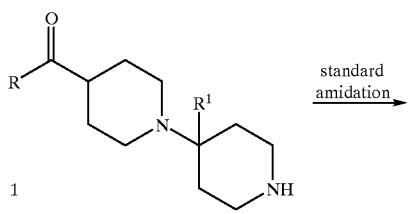

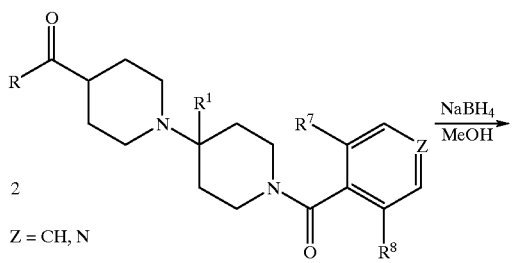

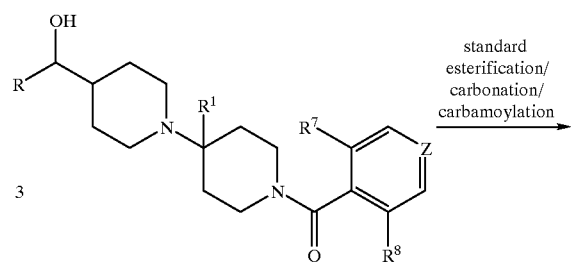

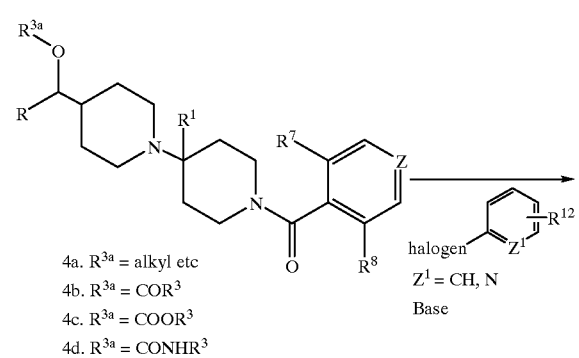

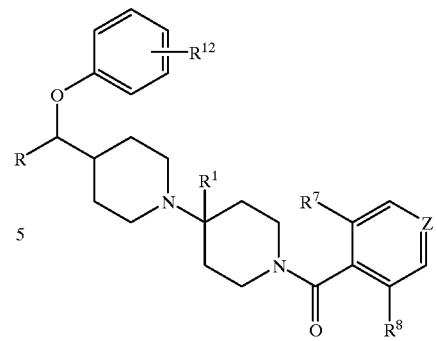

Compounds of formula 3, wherein R, $R^7$ and $R^8$ are as defined for formula I, Z is CH or N, and $R^1$ is an alkyl group such as methyl were prepared as depicted in Scheme 1. Ketone 1, the synthesis of which was described in WO98/05292, was subjected to standard amidation with ArCOOH, EDCl or DEC, and HOBT, or ArCOCl, wherein Ar is $R^7$, $R^8$-substituted phenyl or pyridyl, followed by reduction with $NaBH_4$ to obtain 3. Derivatization of the free hydroxyl moiety with alkyl halides, acyl chlorides ($R^3COCl$), alkyl chloroformates ($ClCOOR^3$) and isocyanides ($O=C=NR^3$) afforded ethers 4a, esters 4b, carbonates 4c, and carbamates 4d, respectively, wherein $R^3$ is a lower alkyl group. The aryloxy compounds, 5, were obtained after condensation of the hydroxyl 3 with phenyl or pyridyl halides in the presence of a base.

Scheme 2

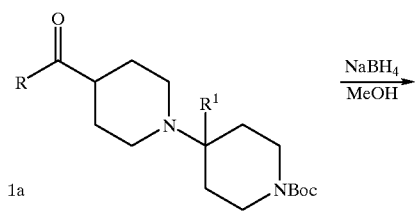

1a

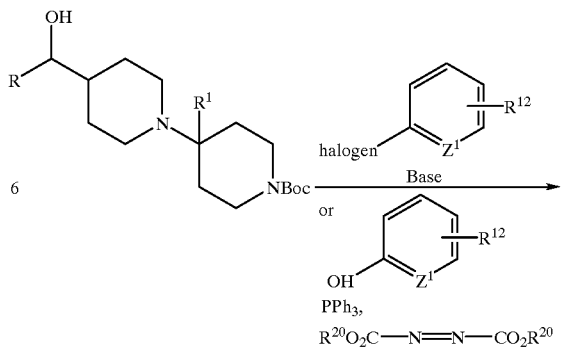

6

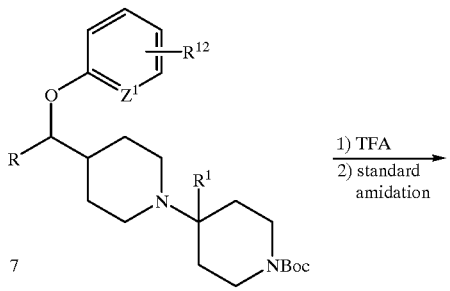

7

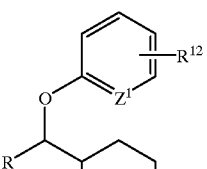

5

Alternatively, compounds of formula 5 can be prepared by reduction of the N-Boc ketone 1a to the alcohol 6 first, followed by functionalization of the free hydroxyl group with a halogen-substituted aryl in the presence of a base as shown in Scheme 2, or by a hydroxy-substituted aryl or heteroaryl (wherein $Z^1$ is as defined in Scheme 1) in the presence of $PPh_3$ and an azodicarboxylate of the formula $R^{19}O_2C-N=N-CO_2R^{20}$, wherein $R^{20}$ is $C_1-C_6$ lower alkyl. Removal of the Boc protecting group and conversion to the amide is performed as in Scheme 1. This route allows the introduction of various aryloxy and heteroaryloxy moieties at $R^3$ through the use of nucleophilic displacement or Mitsunobu-type reaction on intermediate 6.

Scheme 3

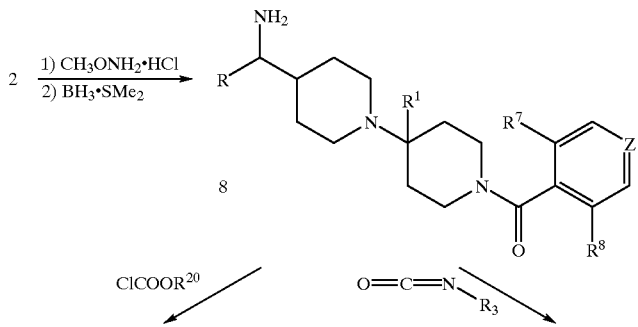

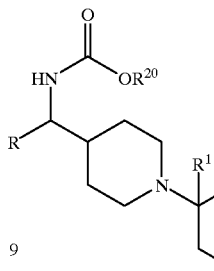 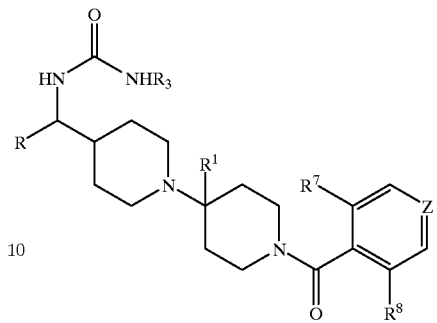

Compounds of formula 8, wherein R, $R^1$, $R^7$, $R^8$ and Z are as described in Scheme 1, were prepared by conversion of the ketone 2 to an oxime group with $CH_3ONH_2·HCl$, and reduction with $BH_3·S(CH_3)_2$ to provide amine 8. Derivatization of the free amine moiety with an alkyl chloroformate ($ClCOOR^{20}$, wherein $R^{20}$ is $C_1$–$C_6$ alkyl) or an isocyanide ($O=C=NR^3$) affords carbamate compounds 9 and urea compounds 10, respectively.

Scheme 3

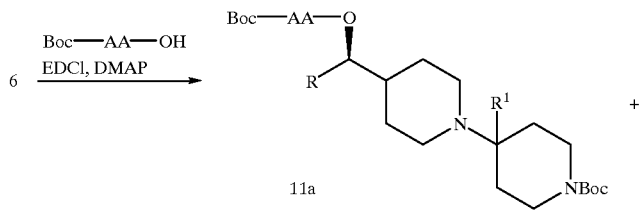

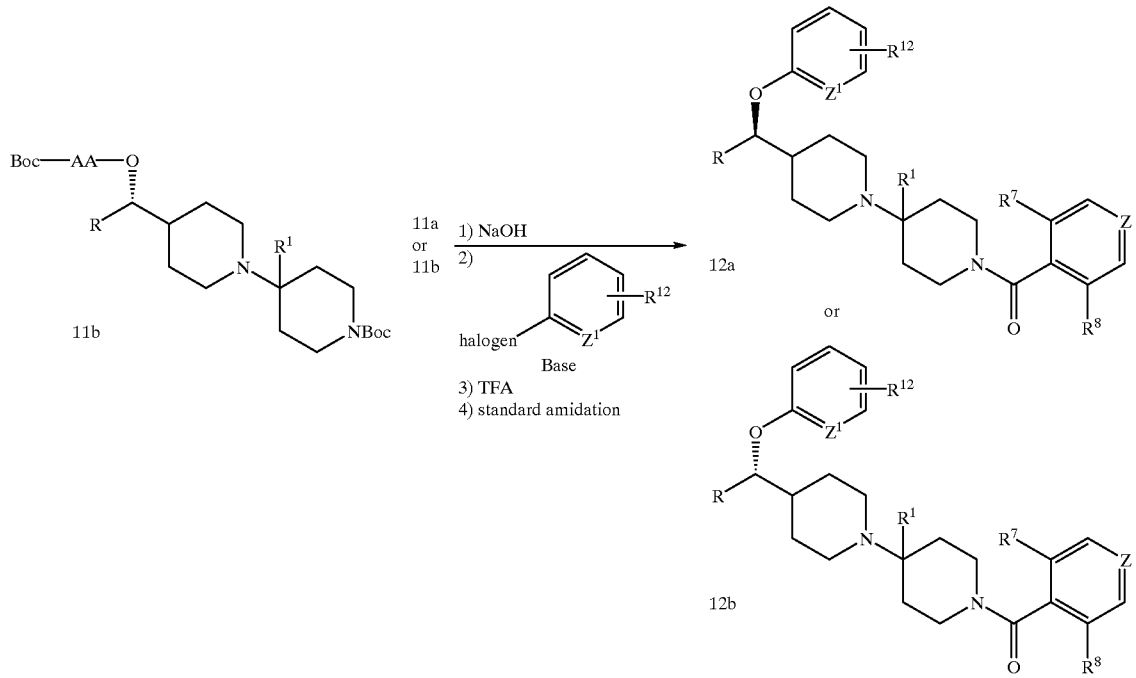

Preparation of chiral analogs was performed through chemical resolution. The alcohol 6 was coupled with a chiral Boc-protected amino acid to obtain diastereoisomers 11a and 11b which were separated by chromatography. The chiral auxialiary was then removed with NaOH for each diastereoisomer and the same sequence of reactions described in Scheme 2 was carried out on each individual enantiomer to obtain compounds 12a and 12b.

Oximes of formula I or II wherein X is C=NOR$^4$ are prepared from the corresponding ketones from any of several methods known to those skilled in the art.

Scheme 5

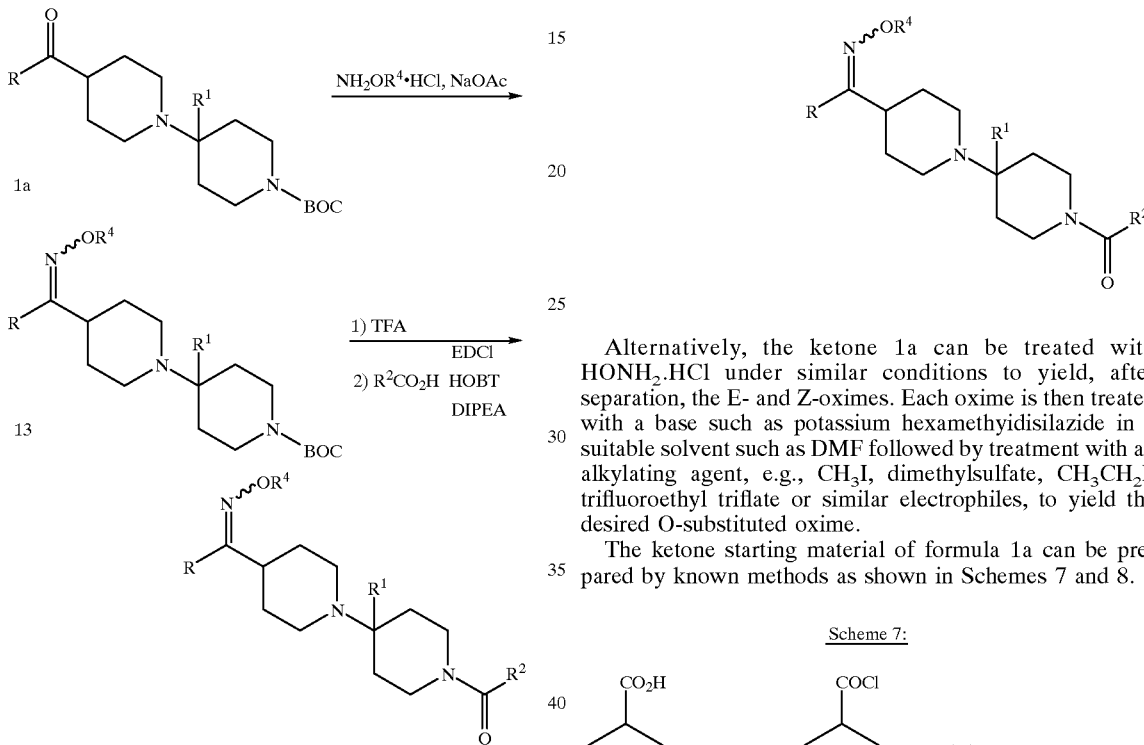

In Scheme 5, the ketone 1a, wherein R and R$^1$ are as defined for formula I and II, is dissolved in a solvent such as CH$_3$OH or ethanol and treated with an R$^4$-substituted hydroxylamine such as O-methylhydroxylamine hydrochloride in the presence of a base such as sodium acetate. The resulting mixture of Z- and E-O-substituted oximes 13 can be separated or the mixture carried through and separated at the end. The BOC protecting group is removed by treatment with an acid such as aqueous HCl or trifluoroacetic acid, and the resulting amine is coupled to an acid under standard conditions to obtain a compound of formula I or II.

Scheme 6

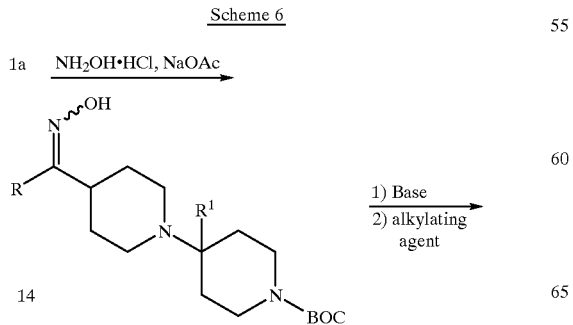

Alternatively, the ketone 1a can be treated with HONH$_2$.HCl under similar conditions to yield, after separation, the E- and Z-oximes. Each oxime is then treated with a base such as potassium hexamethyidisilazide in a suitable solvent such as DMF followed by treatment with an alkylating agent, e.g., CH$_3$I, dimethylsulfate, CH$_3$CH$_2$I, trifluoroethyl triflate or similar electrophiles, to yield the desired O-substituted oxime.

The ketone starting material of formula 1a can be prepared by known methods as shown in Schemes 7 and 8.

Scheme 7:

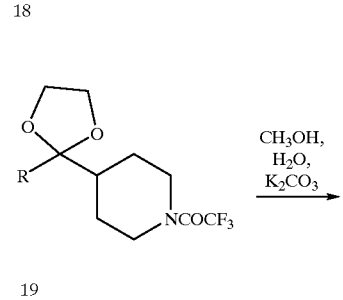

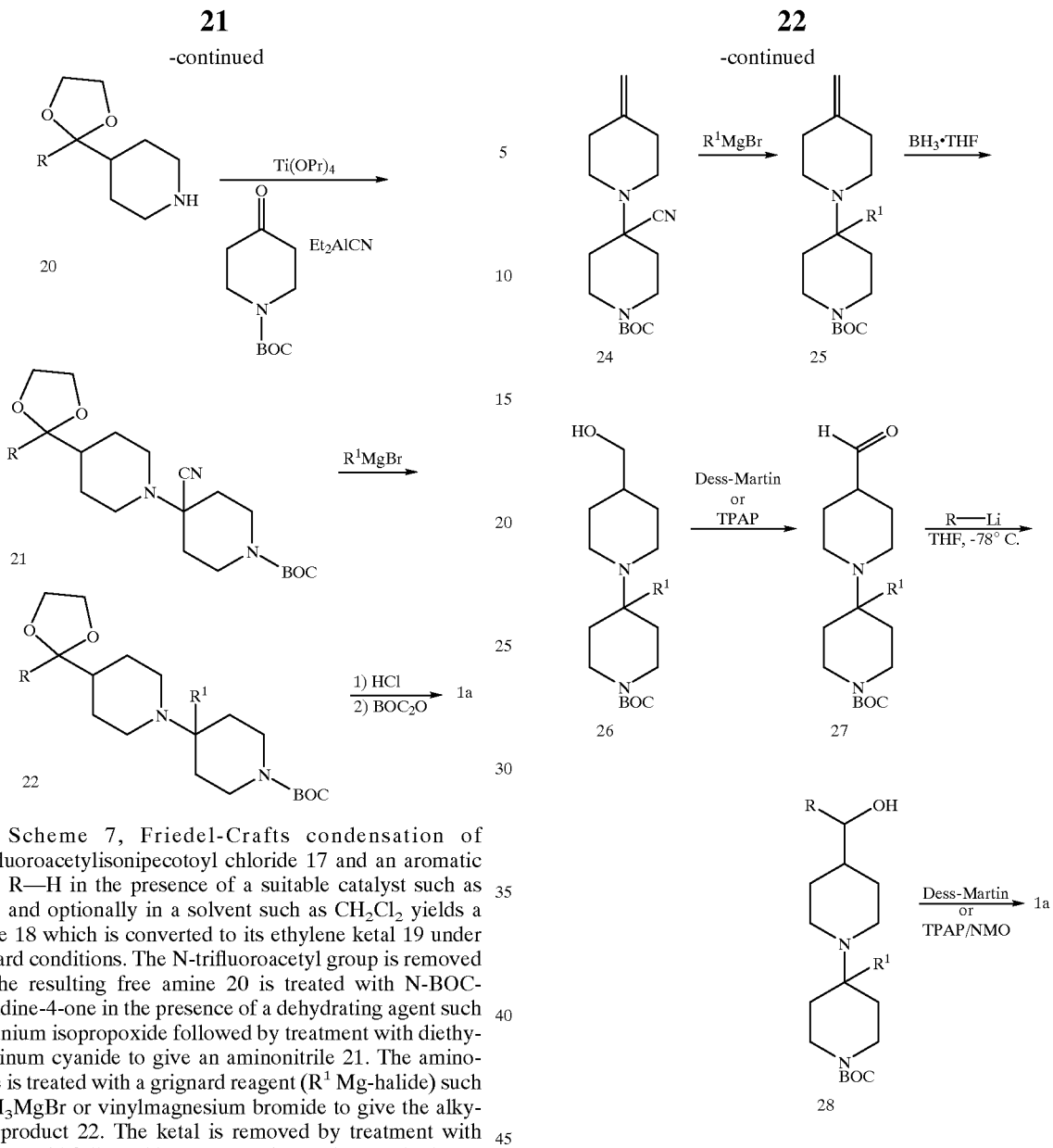

In Scheme 7, Friedel-Crafts condensation of N-trifluoroacetylisonipecotoyl chloride 17 and an aromatic group R—H in the presence of a suitable catalyst such as AlCl$_3$ and optionally in a solvent such as CH$_2$Cl$_2$ yields a ketone 18 which is converted to its ethylene ketal 19 under standard conditions. The N-trifluoroacetyl group is removed and the resulting free amine 20 is treated with N-BOC-piperidine-4-one in the presence of a dehydrating agent such as titanium isopropoxide followed by treatment with diethylaluminum cyanide to give an aminonitrile 21. The aminonitrile is treated with a grignard reagent (R$^1$ Mg-halide) such as CH$_3$MgBr or vinylmagnesium bromide to give the alkylated product 22. The ketal is removed by treatment with aqueous acid followed by re-protection under standard conditions using BOC anhydride to give 1a.

Scheme 8:

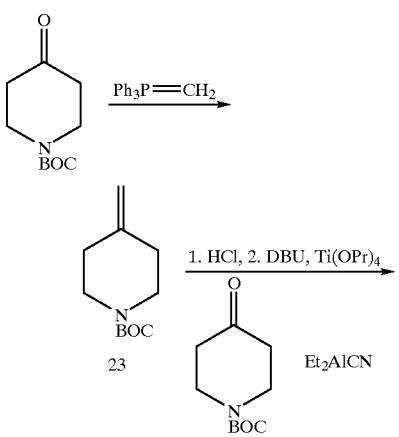

Alternatively, 23, prepared via Wittig olefination of N-BOC-piperidone (Chen et al, *Tetrahedron Lett.*, 37, 30 (1996), 5233–5234), is transformed to intermediate 25 by analogy to the procedure described in Scheme 7. 25 is converted to alcohol 26 by hydroboration/oxidation. Alcohol 26 is treated with a suitable oxidant such as a mixture tetrapropylammonium perruthenate (TPAP) and N-methylmorpholine N-oxide (NMO) to give aldehyde 27. The aldehyde is treated with an aryllithium reagent in a suitable solvent such as ether or THF and the resulting alcohol 28 is treated with an oxidizing agent such as Dess-Martin periodinane or TPAP/NMO to give the desired ketone.

Compounds of formula I or II wherein X is —C(R$^{13}$)(R$^{19}$)—, wherein R and R$^{19}$ are the same, or wherein R and R$^{19}$ are different are prepared according to schemes 9 and 10, respectively. The schemes are exemplified by processes wherein R and R$^{19}$ are each phenyl and wherein R is phenyl and R$^{19}$ is CF$_3$-phenyl, respectively, but the general procedures apply to other R and R$^{19}$ groups.

Scheme 9

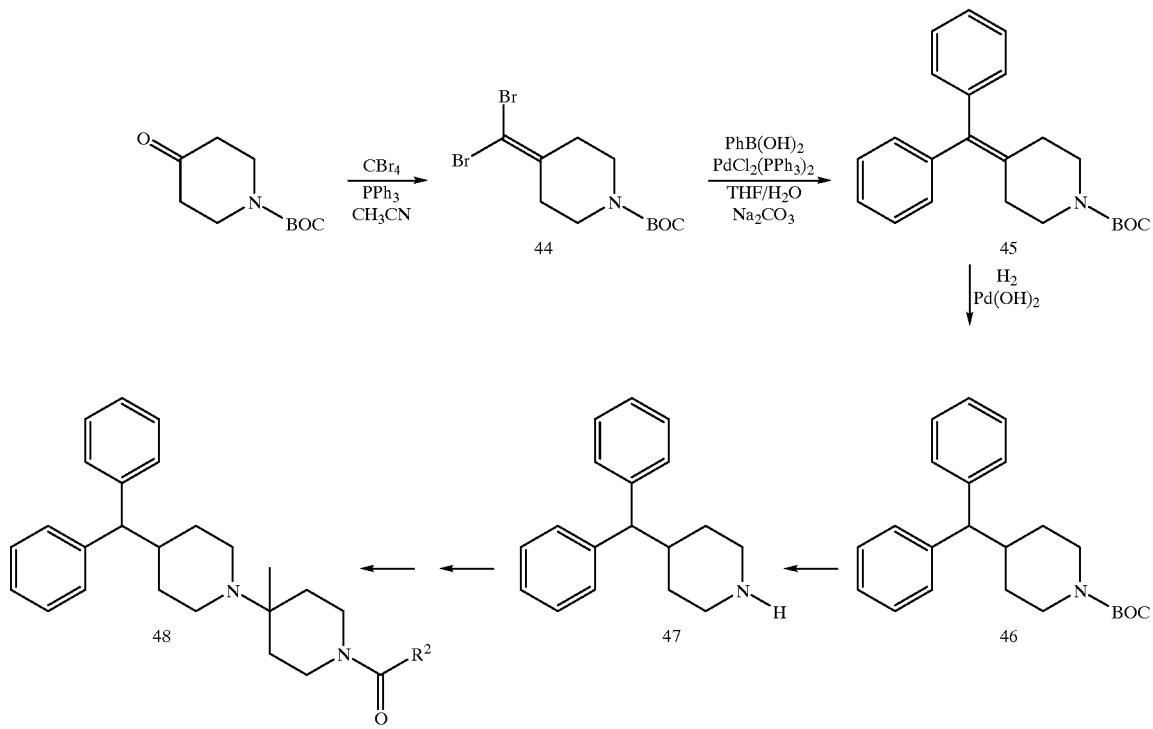

N-BOC-4-piperidone is treated with CBr$_4$ to obtain the di-bromo compound of formula 44, which is then treated with phenylboronic acid to obtain the BOC-protected diphenylmethylene-piperidine of formula 45. The methylene bond is reduced using standard conditions to obtain the BOC-protected diphenylmethyl-piperidine of formula 46, the BOC group is removed and the amine of formula 47 is treated as described for compounds 20–22 of Scheme 7, the BOC group is removed by treatment with TFA, and the resultant amine subjected to a standard amidation procedure, e.g., treatment with a reagent R$^2$COOH and coupling agents such as EDCl, HOBT and a base, to obtain the compounds of formula 48.

Scheme 10

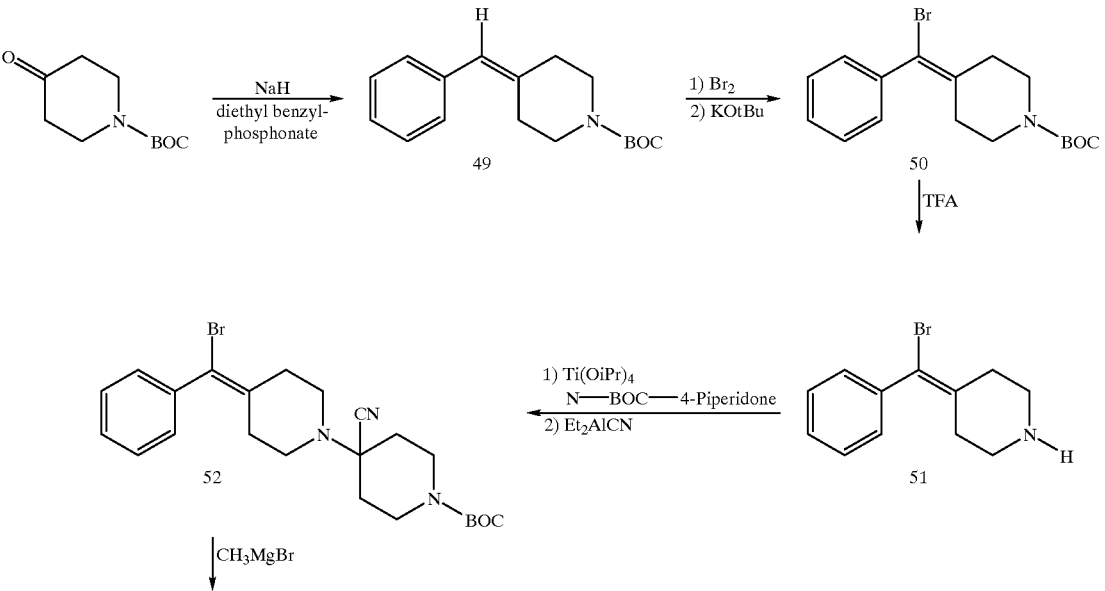

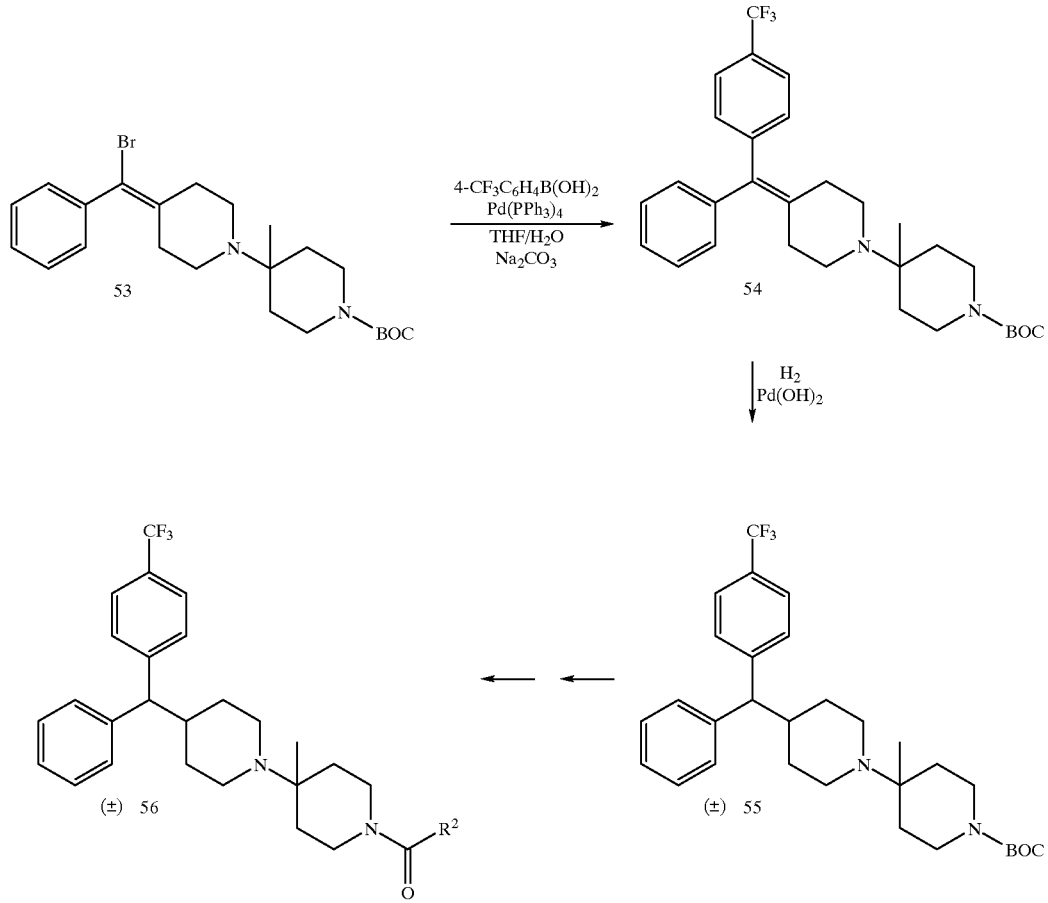

N-BOC-4-piperidone is treated with a reagent such as diethyl benzylphosphonate to obtain the phenylmethylene-piperidine of formula 49, which is then brominated to obtain the bromophenylmethylene-piperidine of fomula 50. The BOC protecting group is removed using standard conditions, e.g., treatment with TFA, to obtain amine 51, and the amine 51 is treated as described for compounds 20–22 of Scheme 7 to obtain the aminonitrile 52, then the protected amine 53. The amine 53 is treated with a reagent such as 4-CF$_3$-phenylboronic acid to obtain compound 54 and the methylene bond is reduced using standard conditions to obtain racemic 55. The BOC group is removed by treatment with TFA, and the resultant amine subjected to a standard amidation procedure, e.g., treatment with a reagent R$^2$COOH and coupling agents such as EDCl, HOBT and a base, to obtain the racemic compounds of formula 56.

Compounds useful in this invention are exemplified by the following preparative examples, which should not be construed to limit the scope of the disclosure. Alternative mechanistic pathways and analogous structures within the scope of the invention may be apparent to those skilled in the art.

EXAMPLE 1

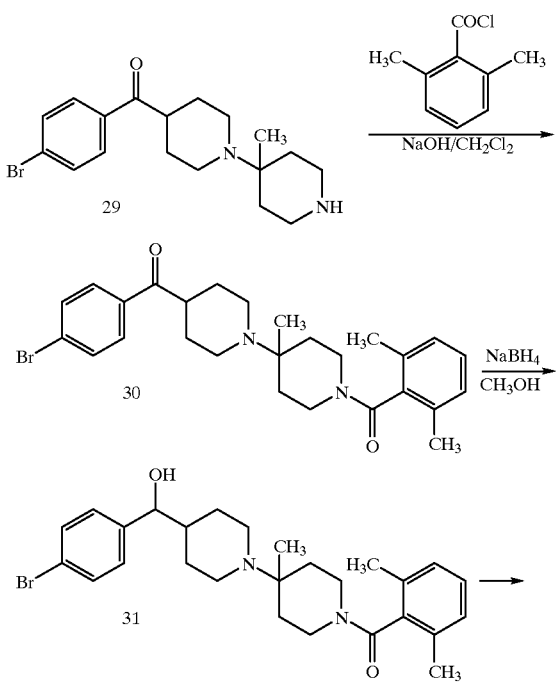

-continued

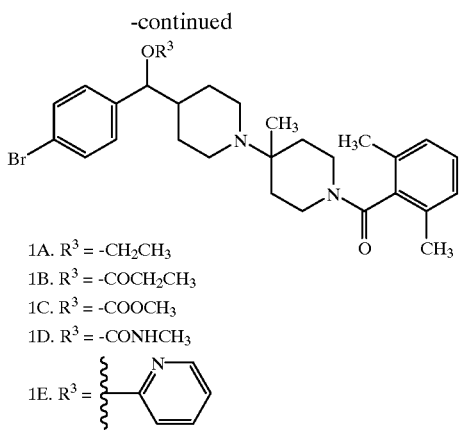

1A. $R^3$ = -CH$_2$CH$_3$
1B. $R^3$ = -COCH$_2$CH$_3$
1C. $R^3$ = -COOCH$_3$
1D. $R^3$ = -CONHCH$_3$

1E. $R^3$ =

A solution of free amine 29 (1.45 g, 3.97 mmol) and 2,6-dimethylbenzoyl chloride (840 mg, 5.0 mmol) in aqueous 1 N NaOH (20 ml) and CH$_2$Cl$_2$ (20 ml) was stirred overnight at RT. The reaction mixture was extracted with CH$_2$Cl$_2$, dried over Na$_2$SO$_4$ and concentrated under high vacuum to provide 30 (1.97 g, 97%), as a slightly yellow foam.

To a solution of ketone 30 (550 mg, 1.11 mmol) in CH$_3$OH (6 ml) was added NaBH$_4$ (60 mg, 1.59 mmol) and the solution was stirred overnight at RT. The reaction mixture was then poured into 0.1 N NaOH, extracted with CH$_2$Cl$_2$, dried over Na$_2$SO$_4$, and concentrated to give 31 (543 mg, 98%), as a slightly yellow foam.

EXAMPLE 1A

To a solution of alcohol 31 (50 mg, 0.10 mmol) in anhydrous DMF (0.5 ml) was added NaH (6.0 mg, 0.25 mmol) followed by ethyl iodide (12 µl, 0.15 mmol) and the reaction was stirred 4 h at 40° C. The reaction mixture was poured into aqueous 0.1 N NaOH, extracted with CH$_2$Cl$_2$, dried over Na$_2$SO$_4$, and concentrated. Purification by preparative chromatography (eluting with CH$_2$Cl$_2$/CH$_3$OH, 9:1) yielded 1A (31 mg, 59%) as a colorless oil: $^1$H-NMR (300 MHz, CDCl$_3$) δ 7.39 (br d, J=8.4 Hz, 2H), 7.02–7.12 (m, 3H), 6.95 (m, 2H), 3.94 (m, 1H), 3.79 (d, J=7.2 Hz, 1H), 3.10–3.35 (m, 4H), 2.60–3.00 (m, 3H), 2.19 (br s, 6H), 1.60–2.10 (m, 5H), 1.05–1.50 (m, 5H), 1.08 (br t, 3H), 0.94 (s, 3H); HRMS (MH$^+$) 527.2271.

EXAMPLE 1B

To a solution of alcohol 31 (50 mg, 0.10 mmol) and pyridine (16.2 µl, 0.20 mmol) in anhydrous CH$_2$Cl$_2$ (0.5 mL) was added propionyl chloride (30 µl, 0.30 mmol) and the solution was stirred overnight at RT. The reaction mixture was treated as for 1A to give, after preparative chromatography (eluting with CH$_2$Cl$_2$/CH$_3$OH, 9:1), 1B (44.7 mg, 81%) as a colorless oil: $^1$H-NMR (300 MHz, CDCl$_3$) δ 7.42 (br d, J=8.2 Hz, 2H), 7.05–7.15 (m, 3H), 6.97 (m, 2H), 5.40 (d, J=7.8 Hz, 1H), 4.09 (m, 1H), 3.43 (m, 1H), 3.23 (m, 1H), 2.96 (m, 1H), 2.82 (m, 1H), 2.70 (m, 1H), 2.21 (d, 3H), 1.60–2.10 (m, 5H), 1.05–1.45 (m, 5H), 1.08 (m, 3H), 0.95 (s, 3H); HRMS (MH$^+$) 555.2230.

EXAMPLE 1C

To a solution of alcohol 31 (29.4 mg, 0.059 mmol) and pyridine (9.5 µl, 0.118 mmol) in anhydrous CH$_2$Cl$_2$ (0.3 mL) was added methylchloro-formate (13.8 µl, 0.18 mmol) and the solution was stirred overnight at RT. The reaction mixture was treated as for 1A to give, after preparative chromatography (eluting with CH$_2$Cl$_2$/CH$_3$OH, 9:1), 1C (15 mg, 46%) as a colorless oil: $^1$H-NMR (300 MHz, CDCl$_3$) δ 7.46 (br d, J=8.4 Hz, 2H), 7.14 (d, J=8.4 Hz, 2H), 7.09 (m, 1H), 6.98 (m, 2H), 5.21 (d, J=7.2 Hz, 1H), 4.09 (m, 1H), 3.71 (m, 3H), 3.45 (m, 1H), 3.24 (m, 1H), 2.97 (m, 1H), 2.82 (m, 1H), 2.70 (m, 1H), 2.22 (br s, 3H), 1.60–2.10 (m, 5H), 1.10–1.50 (m, 5H), 0.95 (s, 3H); HRMS (MH$^+$) 557.2017.

EXAMPLE 1D

A solution of alcohol 31 (30 mg, 0.060 mmol), pyridine (9.7 µl, 0.12 mmol) and methylisocyanate (40 µl, 0.68 mmol) in anhydrous THF (0.3 ml) was stirred 5 h at 45° C. The reaction mixture was treated as for 1A to give, after preparative chromatography (eluting with CH$_2$Cl$_2$/CH$_3$OH, 9:1), 1D (25 mg, 75%) as a colorless oil: $^1$H-NMR (300 MHz, CDCl$_3$) δ 7.42 (br d, J=8.2 Hz, 2H), 7.05–7.15 (m, 3H), 6.98 (m, 2H), 5.34 (m, 1H), 4.08 (m, 1H), 3.44 (m, 1H), 3.24 (m, 1H), 3.19 (s, 3H), 2.96 (m, 1H), 2.65–2.85 (m, 2H), 2.20 (br s, 3H), 1.55–2.10 (m, 5H), 1.10–1.50 (m, 5H), 0.95 (s, 3H); HRMS (MH$^+$) 556.2169.

EXAMPLE 1E

A solution of alcohol 31 (50 mg, 0.10 mmol), NaH 60% in mineral oil (6 mg, 0.15 mmol), and 2-chloropyridine (28.2 µl, 0.30 mmol) in anhydrous DMF (0.5 ml) was stirred 16 h at 90° C. The reaction mixture was treated as for 1A to give, after preparative chromatography (eluting with CH$_2$Cl$_2$/CH$_3$OH, 9:1), 1E (50 mg, 86%) as a colorless oil: $^1$H-NMR (300 MHz, CDCl$_3$) δ 7.98 (m, 1H), 7.47 (br t, J=7.2 Hz, 1H), 7.38 (d, J=8.0 Hz, 2H), 7.21 (d, J=8.0 Hz, 2H), 6.95–7.15 (m, 3H), 6.65–6.80 (m, 2H), 5.74 (br d, J=7.0 Hz, 1H), 4.09 (m, 1H), 3.44 (m, 1H), 3.24 (m, 1H), 2.65–3.05 (m, 3H), 2.22 and 2.23 (s, 3H), 1.60–2.15 (m, 5H), 1.10–1.50 (m, 5H), 0.87 (s, 3H); HRMS (MH$^+$) 576.2230.

Using similar procedures, compounds of the following structure were prepared wherein $R^3$, $R^6$ and $R^2$ are as defined in the table:

| Ex. | $R^6$ | $R^3$ | $R^2$ | HRMS (MH$^+$) found |
|---|---|---|---|---|
| 1F | Br | —C(O)OCH$_2$CH$_3$ | 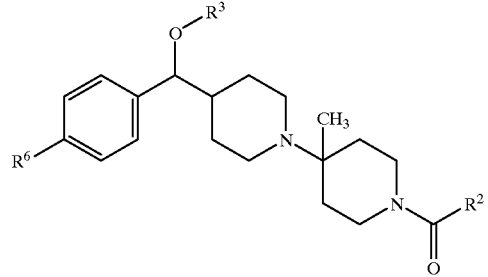 | 571.2181 |

-continued

| Ex. | R⁶ | R³ | R² | HRMS (MH⁺) found |
|---|---|---|---|---|
| 1G | Br | —C(O)CH₃ | 2,6-dimethylphenyl | 541.2054 |
| 1H | Br | —C(O)—(CH₂)₂CH₃ | 2,6-dimethylphenyl | 569.2392 |
| 1I | Br | —C(O)NHCH₂CH₃ | 2,6-dimethylphenyl | 572.2322 |
| 1J | Br | thiazol-2-yl | 2,6-dimethylphenyl | 584.1786 |

-continued

| Ex. | R⁶ | R³ | R² | HRMS (MH⁺) found |
|---|---|---|---|---|
| 1K | Br | pyrimidin-2-yl | 2,6-dimethylphenyl | 577.2162 |
| 1L | Br | pyrazin-2-yl | 2,6-dimethylphenyl | 577.2183 |

Additional data for compounds of Example 1:

| Ex. | ¹H—NMR (300 MHz ¹H NMR (CDCl₃)) |
|---|---|
| 1J | 7.49 (d, J=8.4 Hz, 2H), 7.20–7.35 (m, 3H), 7.15 (m, 1H), 7.04 (m, 2H), 6.64 (d, J=4.5 Hz, 1H), 5.58 and 5.60 (d, J=7.2 Hz, 1H), 4.13 (m, 1H), 3.25–3.60 (m, 2H), 2.70–3.10 (m, 3H), 2.28 and 2.29 (s, 3H), 1.65–2.20 (m, 5H), 1.20–1.55 (m, 5H), 0.92 (br s, 3H) |
| 1K | 8.39 (d, J=5.6 Hz, 1H), 7.42 (d, J=8.4 Hz, 2H), 7.27 (d, J=8.4 Hz, 2H), 7.05–7.20 (m, 2H), 6.99 (m, 2H), 6.84 (m, 1H), 5.70 (d, J=7.8Hz, 1H), 4.11 (m, 1H), 3.43 (m, 1H), 3.25 (m, 1H), 2.65–3.05 (m, 3H), 2.23 and 2.25 (s, 3H), 1.55–2.10 (m, 5H), 1.10–1.50 (m, 5H), 0.88 br s, 3H) |

EXAMPLE 2

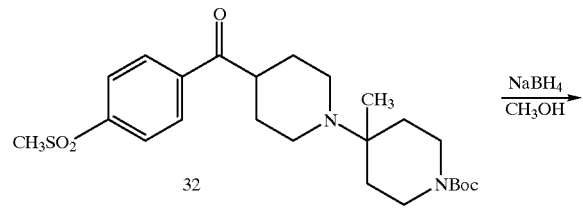

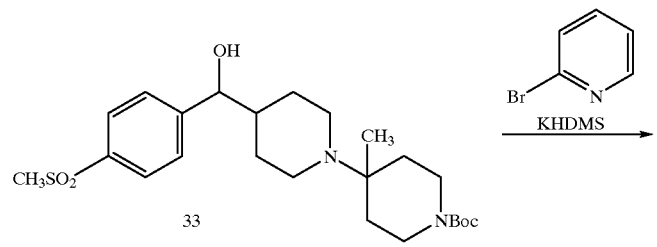

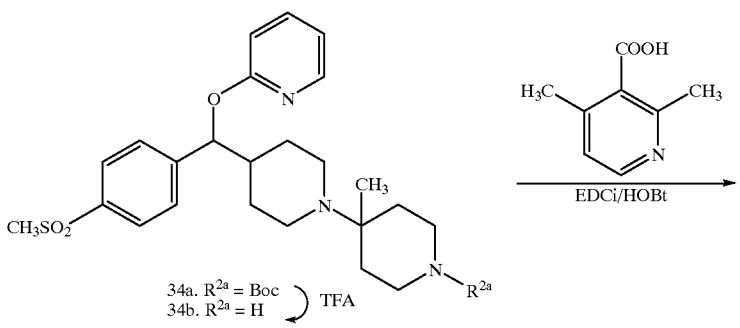

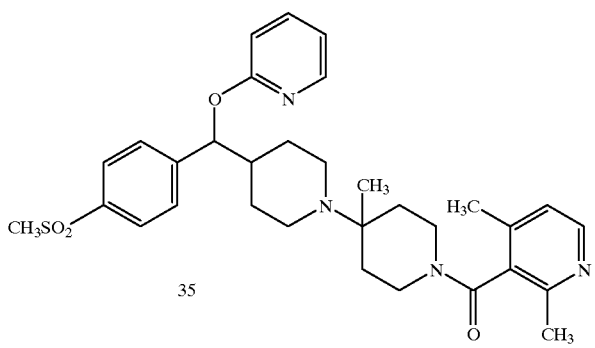

A solution of ketone 32 (0.60 g, 1.29 mmol) and NaBH₄ (60 mg, 1.59 mmol) in CH₃OH (5 ml) was stirred overnight at RT. The reaction mixture was poured into 0.1 N NaOH, extracted with CH₂Cl₂, dried over Na₂SO₄, and concentrated to give 33 (0.60 g, 100%), as a white foam.

To a solution of alcohol 33 (543 mg, 1.2 mmol) in anhydrous toluene (4 ml) was added KHMDA, 0.5 N in toluene (2.6 ml, 1.30 mmol) followed, 15 min. later, by 2-bromopyridine (125 μl, 1.30 mmol). The reaction was heated 5 h at 60° C., cooled to RT and poured into 5% aqueous NaHCO₃ (25 ml). Extraction with CH₂Cl₂, drying over Na₂SO₄ and concentration afforded an oil which was purified by flash chromatography over silica gel (eluting with CH₂Cl₂/AcOEt/Et₃N 50:50:1 to 40:60:1) to yield 34a (310 mg, 49%), as a yellow foam.

A solution of 34a (310 mg, 0.57 mmol) in anhydrous CH₂Cl₂ (2 ml) and TFA (2 ml) was stirred 30 min. at RT. After concentration, the residue was taken up in aqueous 1 N NaOH, extracted with CH₂Cl₂, dried over Na₂SO₄ and concentrated to give 34b (220 mg, 87%), as a white foam.

A solution of free amine 34b (85 mg, 0.19 mmol), 2,4-dimethylnicotinic acid (50 mg, 1.45 mmol), DEC (60 mg, 0.31 mmol), HOBT (50 mg, 0.37 mmol) and N-methylmorpholine (80 ml, 0.72 mmol) in anhydrous DMF (1 ml) was stirred overnight at 40° C. After concentration, the residue was taken up in aqueous 0.1 N NaOH, extracted with CH₂Cl₂, and dried over Na₂SO₄. The residue obtained after concentration of the solvent was purified by preparative chromatography over silica gel (eluting with CH₂Cl₂/CH₃OH/NH₄OH, 96:4:1) to afford 35 (95 mg, 85%), as a colorless oil: ¹H-NMR (300 MHz, CDCl₃) δ 8.33 (d, J=5.1 Hz, 1H), 7.99 (dd, J=4.8 and 1.8 Hz, 1H), 7.86 (d, J=8.4 Hz, 2H), 7.56 (d, J=8.4 Hz, 2H), 7.53 (m, 1H), 6.96 (d, J=5.1 Hz, 1H), 6.75–6.85 (m, 2H), 4.15 (m, 1H), 3.45 (m, 1H), 3.30 (m, 1H), 3.02 (s, 3H), 2.99 (m, 2H), 2.79 (m, 1H), 2.47 and 2.48 (s, 3H), 2.45 (m, 1H), 2.25 and 2.26 (s, 3H), 1.65–2.15 (m, 5H), 1.15–1.55 (m, 5H), 0.90 (s, 3H); HRMS (MH⁺) 577.2858.

Using similar procedures, compounds of the following structure were prepared

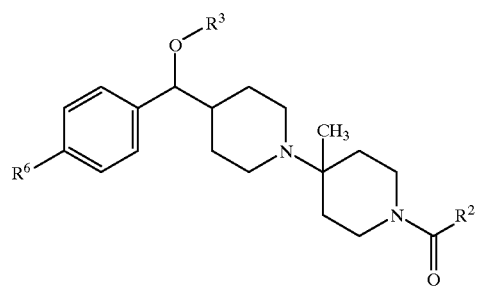

wherein R³, R⁶ and R² are as defined in the table:

| Ex. | R⁶ | R³ | R² | HRMS (MH⁺) found |
|---|---|---|---|---|
| 2A | Br | 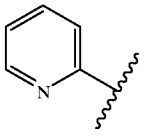 | 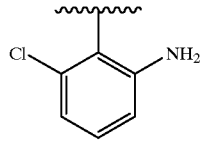 | 599.1062 |
| 2B | Br | 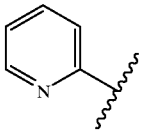 | 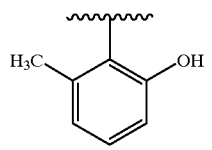 | 578.2006 |
| 2C | Br | 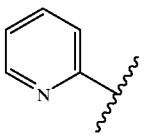 | 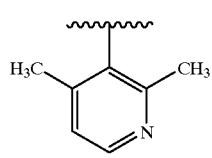 | 577.2172 |
| 2D | Br | 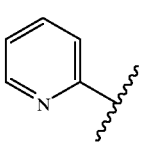 | 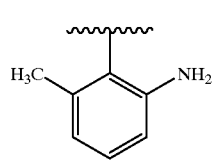 | 577.2172 |
| 2E | H₃CSO₂— | 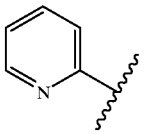 | 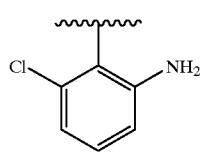 | 597.2296 |
| 2F | H₃CSO₂— | 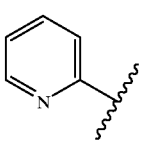 | 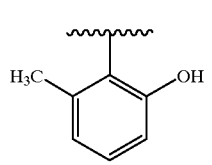 | 578.2697 |
| 2G | F₃C— | 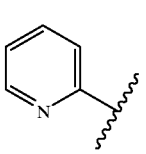 | 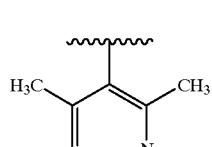 | 567.2947 |
| 2H | H₃CSO₂— | 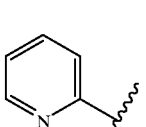 | 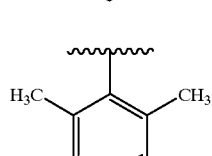 | 576.2890 |
| 2I | H₃CSO₂— | 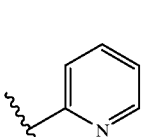 | 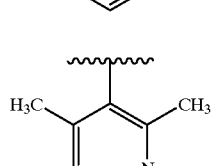 | 593.2805 |

-continued

| Ex. | R⁶ | R³ | R² | HRMS (MH⁺) found |
|---|---|---|---|---|
| 2J | F₃CO— | 2-pyridyl | 2,6-dimethylphenyl | 582.2969 |
| 2K | F₃CO— | 2-pyridyl | 2-methyl-6-hydroxyphenyl | 584.2744 |
| 2L | F₃CO— | 2-pyridyl | 2,4-dimethylpyridin-3-yl | 583.2913 |
| 2M | Br | 2-pyrazinyl | 2,4-dimethylpyridin-3-yl | 580.2123 |
| 2N | Br | 2-pyrazinyl | 2-methyl-6-hydroxyphenyl | 579.1986 |
| 2O | F₃CO— | 2-pyridyl | 2,4-dimethylpyridin-3-yl N-oxide | 599.2847 |
| 2P | Br | 2-pyridyl | 2,4-dimethylpyridin-3-yl N-oxide | 595.2114 |
| 2Q | Br | 2-pyrazinyl | 2,4-dimethylpyridin-3-yl N-oxide | 594.2072 |
| 2R | H₃CSO₂— | 2-pyridyl | 4,6-dimethylpyrimidin-5-yl | 578.2792 |

-continued
| Ex. | R⁶ | R³ | R² | HRMS (MH⁺) found |
|---|---|---|---|---|
| 2S | H₃CSO₂— | 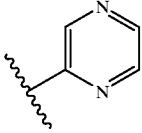 | 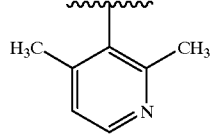 | 578.2801 |
| 2T | H₃CSO₂— | 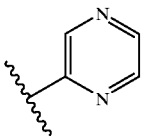 | 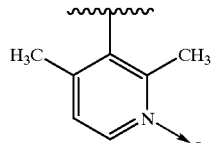 | 594.2750 |
| 2U | H₃CSO₂— | 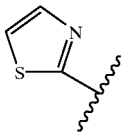 | 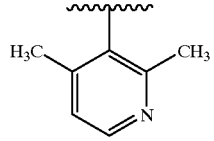 | 583.2426 |
| 2V | H₃CSO₂— | 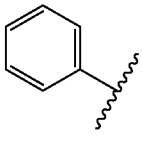 | 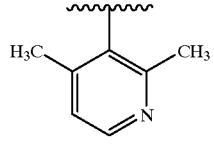 | 576.2896 |
| 2W | H₃CSO₂— | 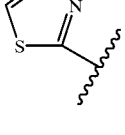 | 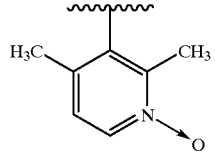 | 599.2362 |
| 2X | F₃C— | 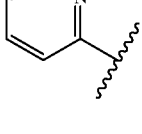 | 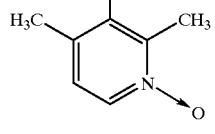 | 583.2905 |
| 2Y | F₃CO— | 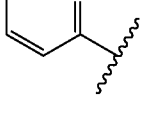 | 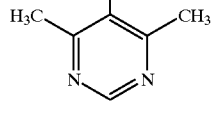 | 584.2848 |
| 2Z | F₃CO— | 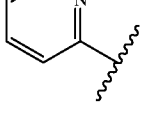 | 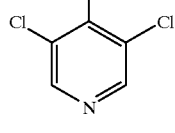 | 623.1790 |
| 2AA | Cl | 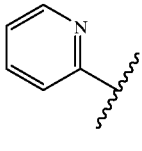 | 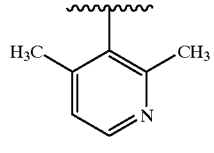 | 533.2673 |

-continued
| Ex. | R⁶ | R³ | R² | HRMS (MH⁺) found |
|---|---|---|---|---|
| 2BB | Cl | 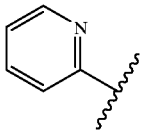 | 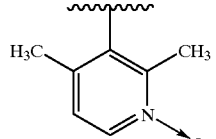 | 549.2646 |
| 2CC | Cl | 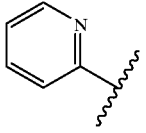 | 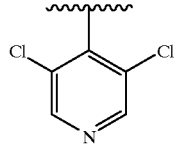 | 573.1606 |
| 2DD | Cl | 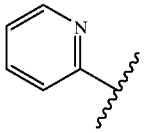 | 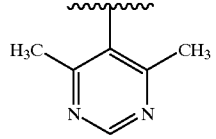 | 534.2637 |
| 2EE | Br | 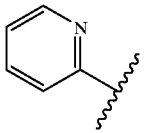 | 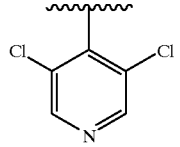 | 619.1062 |
| 2FF | H₃CSO₂— | 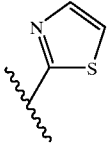 | 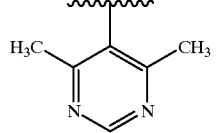 | 584.2375 |
| 2GG | F₃C— | 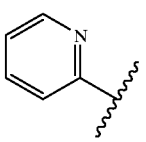 | 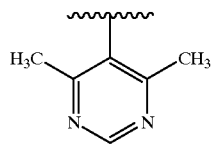 | 568.2913 |
| 2HH | H₃CSO₂— | 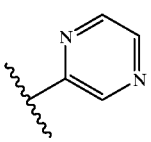 | 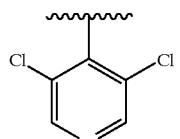 | 618.1722 |
| 2II | H₃CSO₂— | 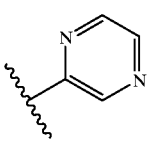 | 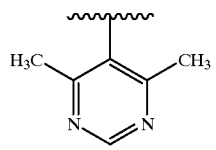 | 579.2749 |
| 2JJ | F₃C— | 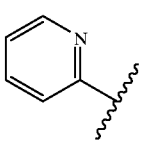 | 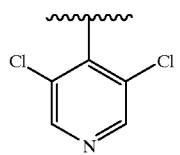 | 607.1871 |

-continued
| Ex. | R⁶ | R³ | R² | HRMS (MH⁺) found |
|---|---|---|---|---|
| 2KK | F | 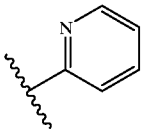 | 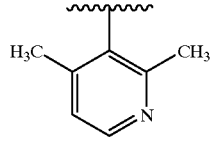 | 517.2696 |
| 2LL | F | 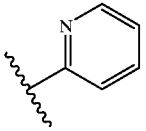 | 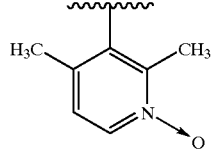 | 533.2916 |
| 2MM | F | 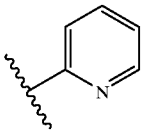 | 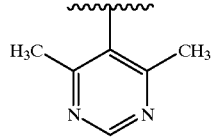 | 518.2944 |
| 2NN | Cl | 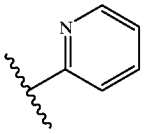 | 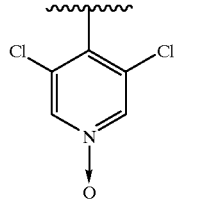 | 589.1534 |
| 2OO | F | 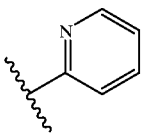 | 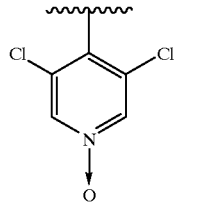 | 573.1818 |
| 2PP | Br | 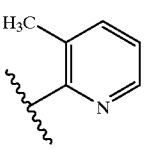 | 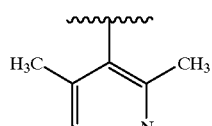 | 591.2330 |
| 2QQ | Br | 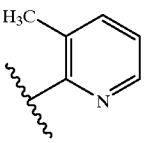 | 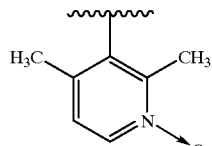 | 607.2291 |
| 2RR | Br | 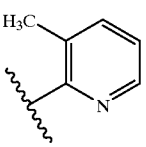 | 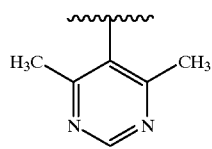 | 592.2294 |

-continued
| Ex. | R⁶ | R³ | R² | HRMS (MH⁺) found |
|---|---|---|---|---|
| 2SS | Br | 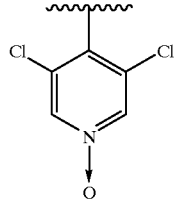 | 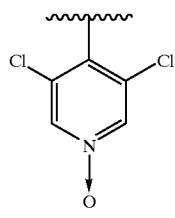 | 633.1040 |
| 2TT | F₃C— | 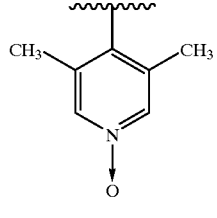 | 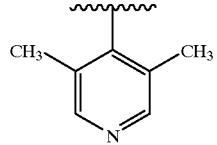 | 623.1809 |
| 2UU | F₃C— | 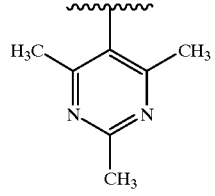 | 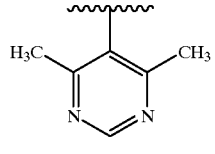 | 583.2909 |
| 2VV | F₃C— | | | 567.2961 |
| 2WW | F | | | 532.3106 |
| 2XX | H | | | 500.3023 |

Additional data for compounds of Example 2:

| Ex. | $^1$H—NMR (300 MHz $^1$H NMR (CDCl$_3$)) |
|---|---|
| 2A | 7.98 (m, 1H), 7.49 (br t, J=7.1 Hz, 1H), 7.39 (d, J=8.1 Hz, 2H), 7.12 (d, J=8.1 Hz, 2H), 7.01 (t, J=8.4 Hz, 1H), 6.65–6.80 (m, 3H), 6.56 (d, J=8.4 Hz, 1H), 5.76 (d, J=7.2 Hz, 1H), 3.95–4.20 (m, 1H); 3.89 and 3.92 (s, 2H), 3.30–3.55 (m, 2H), 3.12 (m, 1H), 2.70–3.00 (m, 2H), 1.65–2.10 (m, 5H), 1.20–1.60 (m, 5H), 0.95 and 0.99 (s, 3H) |
| 2G | 8.31 (d, 1H), 8.01 (d, 1H), 7.50 (m, 4H), 6.95 (d, 1H), 6.80 (m, 2H), 5.90 (d, 1H), 4.15 (d, 1H), 3.25–3.55 (m, 2H), 2.80–3.15 (m, 3H), 2.50 (d, 3H), 2.30 (d, 3H), 1.80–2.15 (m, 7H), 1.20–1.60 (m, 5H), 0.92 (s, 3H) |
| 2K | 7.97 (m, 1H), 7.45 (m, 1H), 7.32 (t, J=8.4 Hz, 2H), 7.06 (m, 2H), 7.01 (m, 1H), 6.60–6.75 (m, 4H), 5.77 and 5.79 (d, J=5.6 Hz, 1H), 3.55 (m, 1H), 3.32 (m, 1H), 2.70–2.95 (m, 2H), 2.18 (s, 3H), 1.65–2.10 (m, 5H), 1.15–1.55 (m, 5H), 0.78 and 0.91 (s, 3H) |
| 2M | 8.29 (d, J=5.2 Hz, 1H), 8.18 (m, 1H), 7.98 (br s, 1H), 7.89 (br s, 1H), 7.38 (d, J=8.4 Hz, 2H), 7.18 (d, J=8.4 Hz, 2H), 6.92 (d, J=5.2 Hz, 1H), 5.67 (d, J=7.2 Hz, 1H), 4.07 (m, 1H), 3.43 (m, 1H), 3.26 (m, 1H), 2.65–3.05 (m, 3H), 2.41 and 2.42 (s, 3H), 2.20 (br s, 3H), 1.60–2.20 (m, 5H), 1.05–1.50 (m, 5H), 0.85 (br s, 3H) |
| 2P | 8.14(d, J=6.8Hz, 1H), 8.02(m, 1H), 7.51 (m, 1H), 7.41 (d, J=8.0 Hz, 2H), 7.25 (d, J=8.0 Hz, 2H), 6.98 (d, J=6.4 Hz, 1H), 6.78 (m, 1H), 6.73 (m, 1H), 5.78 (d, J=6.8 Hz, 1H), 4.17 (m, 1H), 3.43 (m, 1H), 3.32 (m, 1H), 2.95 (m, 1H), 2.86 (m, 1H), 2.75 (m, 1H), 2.44 and 2.46 (s, 3H), 2.23 and 2.25 (s, 3H), 1.65–2.10 (m, 5H), 1.15–1.50 (m, 5H), 0.90 (s, 3H) |
| 2HH | 8.49 (s, 2H), 8.26 (br s, 1H), 8.04 (br s, 1H), 7.80–7.95 (m, 3H), 7.53 (d, J=8.4 Hz, 2H), 5.81 (d, J=6.8 Hz, 1H), 4.16 (m, 1H), 3.30–3.50 (m, 2H), 2.94 (m, 2H), 2.80 (m, 1H), 1.75–2.15 (m, 5H), 1.25–1.50 (m, 5H), 0.89 (s, 3H) |
| 2MM | 8.93 (s, 1H), 8.04 (br d, J=4.8 Hz, 1H), 7.50 (m, 1H), 7.32 (m, 2H), 6.97 (m, 1H), 6.78 (m, 1H), 6.72 (m, 1H), 5.82 (m, 1H), 4.21 (m, 1H), 3.25–3.50 (m, 2H), 2.93 (m, 2H), 2.78(m, 1H), 2.44 and 2.46 (s, 3H), 1.90–2.15 (m, 3H), 1.70–1.90 (m, 2H), 1.15–1.50(m, 5H), 0.90(s, 3H) |
| 2NN | 8.17 (s, 1H), 8.01 (br d, J=4.0 Hz, 1H), 7.50 (br t, J=8.0 Hz, 1H), 7.20–7.35 (m, 4H), 6.78 (t, J=6.8 Hz, 1H), 6.71 (m, 1H), 5.80 (d, J=6.8 Hz, 1H), 4.18 (m, 1H), 3.44 (m, 1H), 3.39 (m, 1H), 3.00 (m, 2H), 2.80 (m, 1H), 1.70–2.15 (m, 5H), 1.10–1.50 (m, 5H), 0.90 (s, 3H) |
| 2PP | 8.37 (d, J=6.0 Hz, 1H), 7.83 (br d, J=4.6 Hz, 1H), 7.41 (d, J=8.4 Hz, 2H), 7.34 (d, J=6.0 Hz, 1H), 7.22 (d, J=8.4 Hz, 2H), 6.97 (d, J=4.6 Hz, 1H), 6.68 (br t, J=6.0 Hz 1H), 5.89 (br d, J=6.8 Hz, 1H), 4.20 (m, 1H), 3.20–3.50 (m, 2H), 2.97 (m, 2H), 2.78 (m, 1H), 2.47 and 2.49 (s, 3H), 2.23 and 2.26 (s, 3H), 2.23 (s, 3H), 1.65–2.15 (m, 5H), 1.15–1.55 (m, 5H), 0.90 (s, 3H) |

EXAMPLE 3

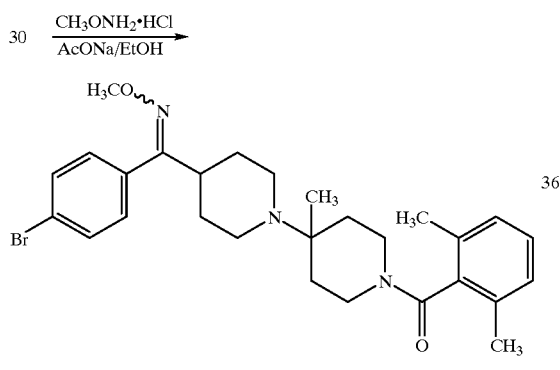

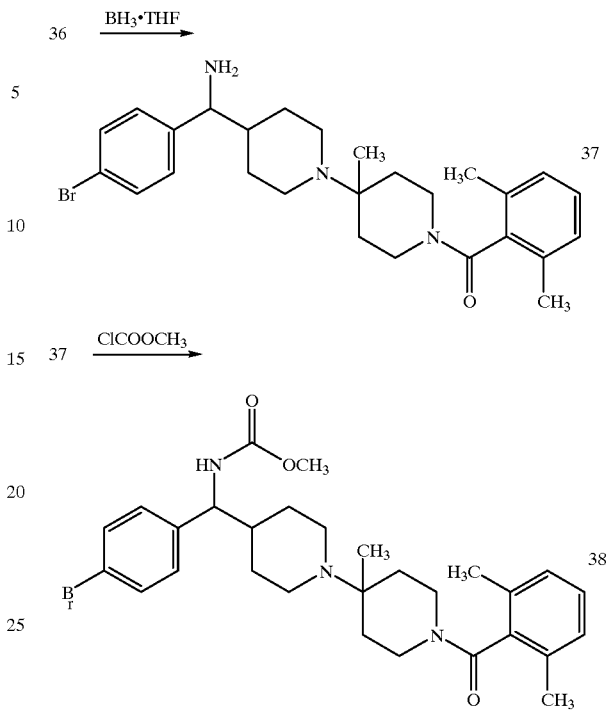

To a solution of ketone 30 (1.5 g, 3.22 mmol) in CH$_3$OH (50 ml) was added sodium acetate (5.0 g, 47 mmol) and O-Methyl hydroxylamine hydrochloride (3.26 g, 47 mmol), and the solution was stirred at RT for 24 h. The resulting mixture was then poured into aqueous NaOH and extracted with CH$_2$Cl$_2$. The combined extracts were dried, concentrated and chromatographed to yield 1.50 g (94%) of oxime 36, as a mixture of E and Z isomers.

To a stirred solution of oxime 36 (0.200 g, 0.380 mmol) in THF (5 ml) was added BH$_3$.THF (1.0 M solution in THF) at 0° C. and the solution was then warmed to RT and stirred for 1 h. The reaction mixture was then cooled to 0° C. and a solution of 1 N KOH in CH$_3$OH (5 ml) was added. The reaction was warmed slowly to 60° C. for 2 h, cooled to RT, quenched with water and extracted with CH$_2$Cl$_2$. Combined organic layers were concentrated and chromatographed over silica gel (eluting with 20% EtOH/EtOAc) to afford 0.100 g (50%) of amine 37.

To a stirred solution of amine 37 (0.015 g, 0.030 mmol) was added pyridine (0.5 ml) and ClCOOCH$_3$ (0.25 ml), and the solution was stirred overnight. It was then poured into water, extracted with EtOAc, dried, concentrated and purified by preparative chromatography to give 0.010 g of desired product 38: $^1$H-NMR (300 MHz, CDCl$_3$) δ 7.45 (d, 2H), 7.05–7.12 (m, 3H), 6.95 (d, 2H), 4.95 (m, 1H), 4.45 (m, 1H), 4.15 (m, 1H), 3.62 (s, 3H), 3.47 (m, 1H), 3.25 (m, 1H), 2.88–3.10 (m, 3H), 2.25 (s, 6H), 1.20–2.10 (m, 12H), 0.90 (s, 3H); HRMS (MH$^+$) 558.3013.

EXAMPLE 4

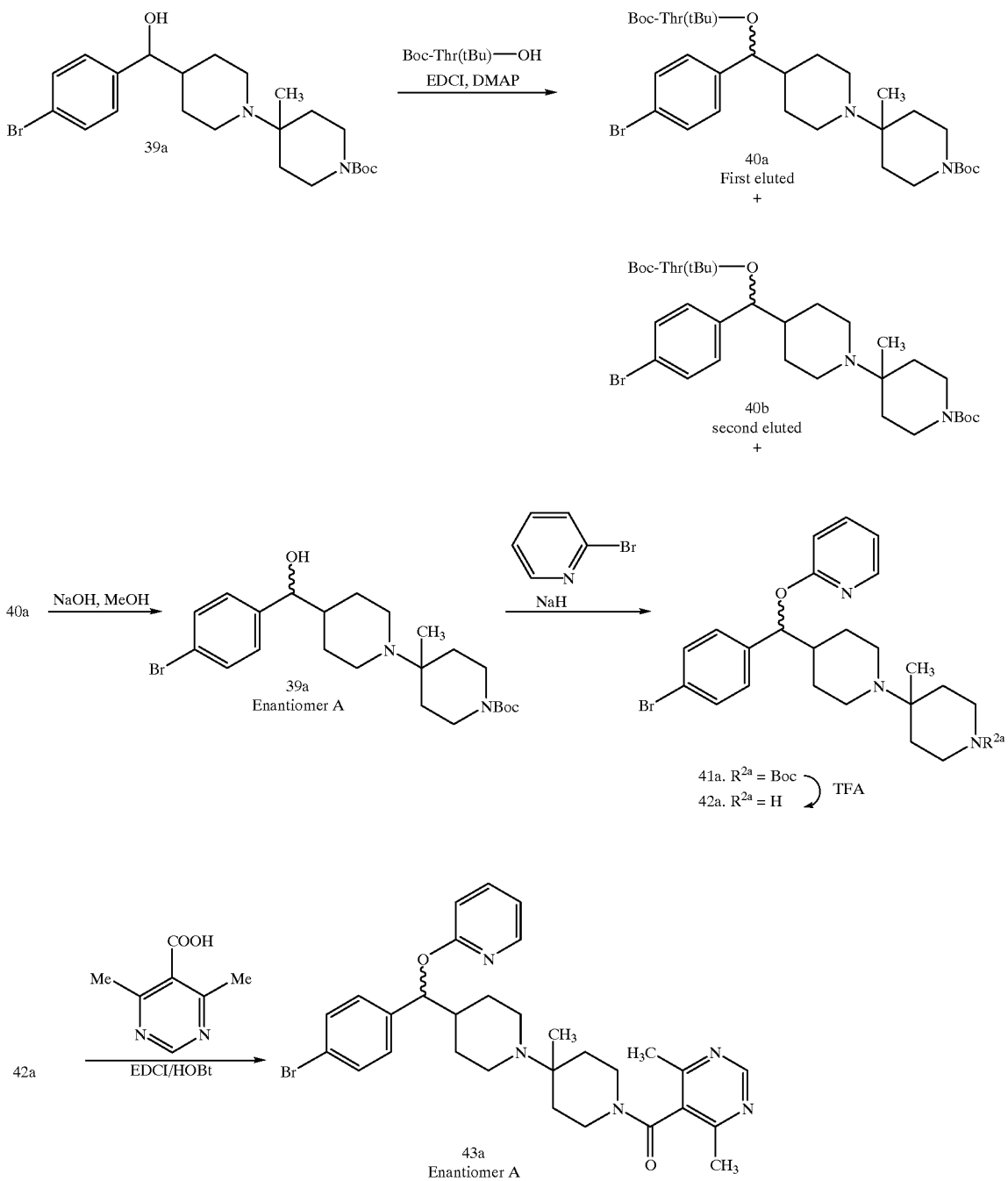

A solution of alcohol 39ab (660 mg, 1.41 mmol), Boc-Thr(t-Bu)-OH (413 mg, 1.50 mmol), DEC (290 mg, 1.50 mmol) and DMAP (190 mg, 1.55 mmol) in anhydrous CH$_2$Cl$_2$ (5 ml) was stirred overnight at RT. The reaction mixture was poured into aqueous saturated NaHCO$_3$, extracted with CH$_2$Cl$_2$, and dried over Na$_2$SO$_4$. The residue obtained after concentration of the solvent was subjected to flash chromatography over silica gel (eluting with CH$_2$Cl$_2$/acetone, 9:1) to afford, in order of elution: (i) first 40a (391 mg, 38%), as a white foam; (ii) second 40b (391 mg, 38%), as a white foam.

To a solution of diastereoisomer 40a (391 mg, 0.54 mmol) in CH$_3$OH (3 ml) was added NaOH (110 mg, 2.75 mmol; 5 equiv.) and the solution was stirred at 65° C. for 3 h. The final mixture was then poured into aqueous 0.1 N NaOH and extracted with CH$_2$Cl$_2$ to yield 39a (Enantiomer A) (246 mg, 98%) as a white foam. (Following the same procedure, 40b gave 39b (Enantiomer B). 40a gives 43a (Enantiomer A) and 40b gives 43b (Enantiomer B.)).

A solution of alcohol 39a (210 mg, 0.45 mmol), NaH 60% in mineral oil (23 mg, 0.96 mmol), and 2-bromopyridine (60 μl; 0.62 mmol) in anhydrous DMF (1.5 ml) was stirred 2 h at 75° C. The reaction mixture was poured into aqueous satrd NaHCO$_3$, extracted with CH$_2$Cl$_2$, dried over Na$_2$SO$_4$ and purified by flash chromatography over silica gel (eluting with CH$_2$Cl$_2$/AcOEt/Et$_3$N, 60:40:0.5 to 40:60:0.5) to afford 41a (143 mg, 59%).

Removal of the Boc-protecting group in 41a (93 mg, 0.17 mmol) proceeded as for 34b to provide 42a (68 mg, 91%), as a white foam.

The amine 42a (50 mg, 0.11 mmol) was coupled with 4,6-dimethylpyrimidine-5-carboxylic acid following the conditions described for the synthesis of 35 to yield 43a (28 mg, 44%). $^1$H-NMR (300 MHz, CDCl$_3$) δ 8.92 (s, 1H), 8.02 (m, 1H), 7.51 (m, 1H), 7.51 (br t, J=8.4 Hz, 1H), 7.41 (d, J=8.4 Hz, 2H), 7.24 (d, J=8.4 Hz, 2H), 6.78 (m, 1H), 6.73 (m, 1H), 5.78 (m, 1H), 4.19 (m, 1H), 3.41 (m, 1H), 3.36 (m, 1H), 2.94 (m, 1H), 2.78 (m, 1H), 2.44 and 2.46 (s, 3H), 1.65–2.15 (m, 5H), 1.15–1.50 (m, 5H), 0.90 (s, 3H)); HRMS (MH$^+$) 578.2140.

The following compounds were prepared via similar methods:

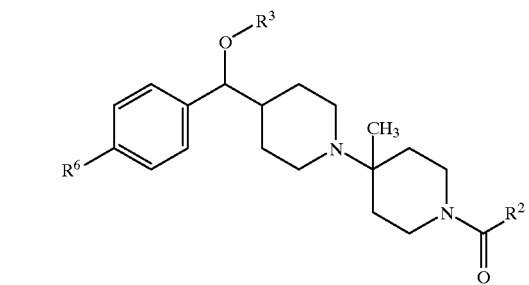

wherein R$^3$, R$^6$ and R$^2$ are as defined in the table:

| Ex. | Enantiomer | R$^6$ | R$^3$ | R$^2$ | HRMS (MH$^+$) found |
|---|---|---|---|---|---|
| 4A | A | Br | 2-pyridyl | 3,4-dimethyl-2-methylpyridin-... (H$_3$C, CH$_3$) | 577.2172 |
| 4B | B | Br | 2-pyridyl | (H$_3$C, CH$_3$) pyridine | 577.2162 |
| 4C | B | Br | 2-pyridyl | 4,6-dimethylpyrimidin-5-yl | 578.2119 |
| 4D | A | F$_3$CO— | 2-pyridyl | 4,6-dimethylpyrimidin-5-yl | 584.2864 |
| 4E | B | F$_3$CO— | 2-pyridyl | 4,6-dimethylpyrimidin-5-yl | 583.2862 |
| 4F | A | F$_3$CO— | 2-pyridyl | 3,5-dimethylpyridin-4-yl | 583.2904 |

-continued
| Ex. | Enantiomer | R$^6$ | R$^3$ | R$^2$ | HRMS (MH$^+$) found |
|---|---|---|---|---|---|
| 4G | A | F$_3$CO— | 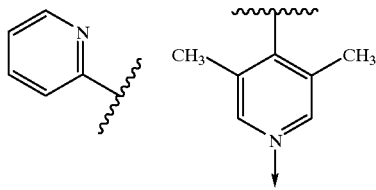 | 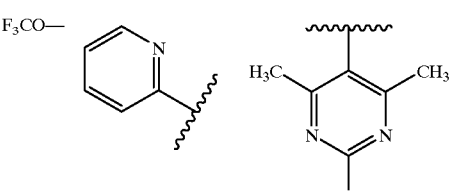 | 599.2857 |
| 4H | A | F$_3$CO— | 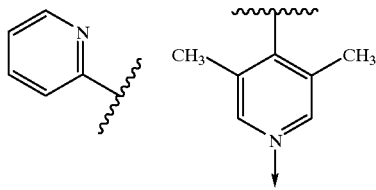 | 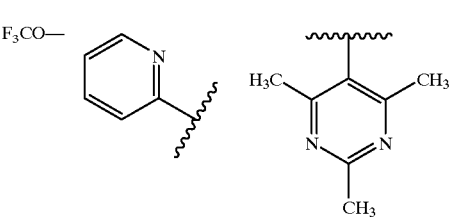 | 595.2994 |
| 4I | B | F$_3$CO— | 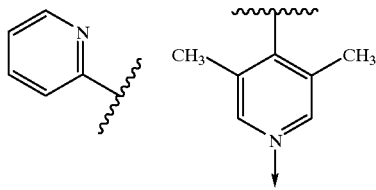 | 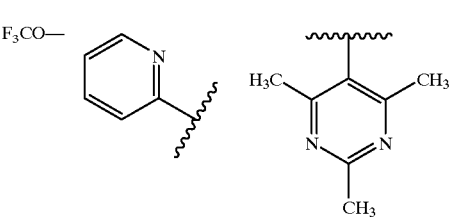 | 598.3000 |
| 4J | A | Cl | 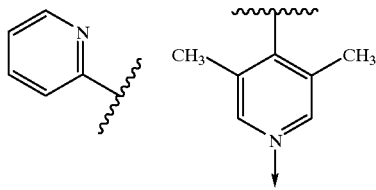 | 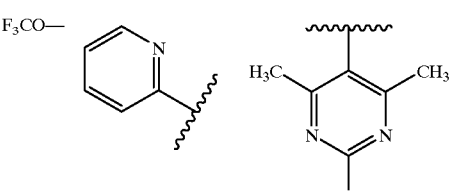 | 534.2639 |
| 4K | A | Cl | 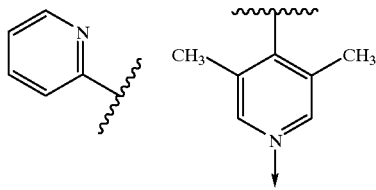 | 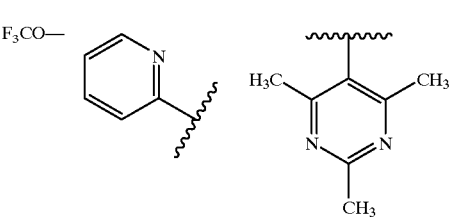 | 548.2784 |
| 4L | B | Cl | 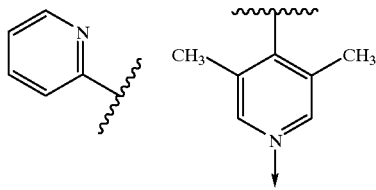 | 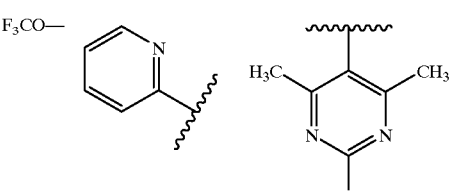 | 534.2644 |
| 4M | B | Cl | 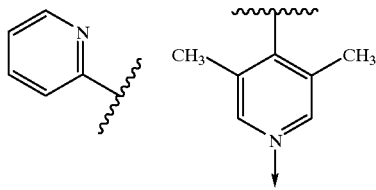 | 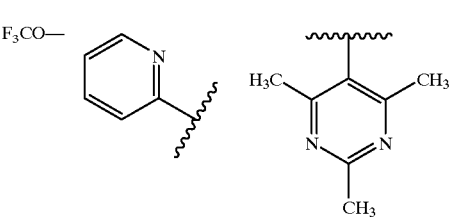 | 548.2784 |

-continued

| Ex. | Enantiomer | R⁶ | R³ | R² | HRMS (MH⁺) found |
|---|---|---|---|---|---|
| 4N | A | F₃CO— | (2-pyridyl) | 4,6-dimethyl-2-aminopyrimidin-5-yl | 599.2947 |
| 4O | B | F₃CO— | (2-pyridyl) | 4,6-dimethyl-2-aminopyrimidin-5-yl | 599.2947 |

Additional data for compounds of Example 4:

| Ex. | ¹H—NMR (300 MHz ¹H NMR (CDCl₃)) |
|---|---|
| 4G | 8.05 (m, 1H), 7.97 (s, 2H), 7.53 (t, J=7.5 Hz, 1H), 7.41 (d, J=8.4 Hz, 2H), 7.16 (d, J=8.4 Hz, 2H), 6.81 (t, J=6.4 Hz, 1H), 6.76 (m, 1H), 5.87 (m, 1H), 4.19 (m, 1H), 3.30–3.50 (m, 2H), 2.99 (m, 2H), 2.79 (m, 1H), 2.20 and 2.22 (s, 3H), 1.70–2.15 (m, 5H), 1.15–1.50 (m, 5H), 0.91 (s, 3H) |
| 4I | 8.03 (m, 1H), 7.53 (m, 1H), 7.39 (d, J=8.4 Hz, 2H), 7.14 (d, J=8.4 Hz, 2H), 6.79 (t, J=6.8 Hz, 1H), 6.73 (m, 1H), 5.87 (m, 1H), 4.19 (m, 1H), 3.42 (m, 1H), 3.37 (m, 1H), 2.98 (m, 2H), 2.80 (m, 1H), 2.41 and 2.43 (s, 3H), 1.90–2.15 (m, 3H), 1.70–1.90 (m, 2H), 1.20–1.50 (m, 5H), 0.91 (s, 3H) |

EXAMPLE 5

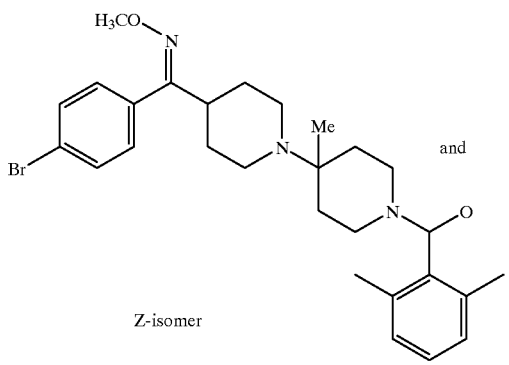

Z-isomer and

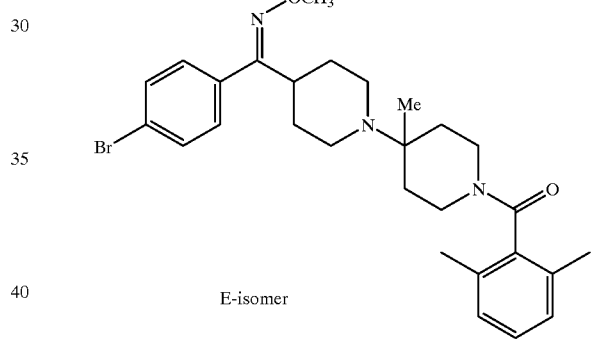

E-isomer

1) Trifluroacetic anhydride (TFAA) (300 ml) is added to isonipecotic acid (96 g) at 0° C. and the reaction mixture is heated at reflux for 4h. Excess TFAA is removed under vacuo, the reaction mixture is taken up in EtOAc, washed with water and concentrated to give 160 g of the amide. 50 g of this amide is treated with SOCl₂ (300 ml) and the reaction mixture heated at reflux overnight. Excess thionyl chloride is then removed under vacuo to give 54 g of the acid chloride.

2) AlCl₃ (11 g) is added slowly to a solution of the product of step 1 (10 g) in bromobenzene (40 ml) at ambient temperature and the reaction mixture is heated at reflux for 4 h. It is then cooled and poured into a mixture of conc. HCl and ice, and the product is extracted with EtOAc. The organic layer is separated and washed with water, half saturated NaHCO₃ solution and concentrated to give 16.21 g of the desired ketone.

3) The product of step 2 (16.21 g) is dissolved in toluene (200 ml) containing ethylene glycol (25 ml) and p-toluenesulfonic acid (0.5 g). The reaction mixture is heated at reflux with azeotropic removal of water until no further water is collected. The reaction mixture is concentrated to give 17.4 g of the desired ketal.

4) The crude product of step 3 (17.4 g) is dissolved in CH₃OH (100 ml) and to this is added water (25 ml) and K$_2$CO$_3$ (12 g) and the reaction mixture is stirred at ambient temperature overnight. The reaction mixture is diluted with water and extracted with EtOAc. The organic layer is separated, washed with water and brine, and concentrated to give 12.55 g of the desired amine.
5) To a stirred solution of the product of step 4 (7.2 g, 23 mmol) and N-BOC-piperidine-4-one (4.8 g, 24 mmol) in 1,2-dichloroethane (20 ml) is added titanium isopropoxide (6.7 ml, 32.3 mmol) and the mixture is stirred for 12 h at RT. The reaction mixture is concentrated and a 1.0 M solution of diethyl aluminium cyanide (35 ml) is added at RT and stirred for 3 h. The reaction mixture is then diluted with EtOAc, quenched with water (5 ml) and stirred for 2 h. The mixture is then filtered through celite and the resulting filtrate is concentrated and chromatographed with 30% EtOAc/hexanes to afford 7.3 g (63%) of the desired cyanide.
6) To a stirred solution of the product of step 5 (7.3 g, 14.03 mmol) in THF (100 ml) is added a 3.0M solution CH$_3$MgBr in Et$_2$O (14.0 ml, 42 mmol) at RT and the mixture is stirred for 2 h. The reaction mixture is then quenched with saturated aqueous NH$_4$Cl and extracted with CH$_2$Cl$_2$. The extracts are concentrated to afford 7.0 g of desired methylated compound.
7) The crude ketal of step 6 is dissolved in EtOAc (100 ml) and 6 N HCl (40 ml) and conc. HCl (10 ml) is added and the mixture stirred at RT for 24 h. The reaction mixture is then neutralised with 20% NaOH and extracted with EtOAc, dried and concentrated to yield 5.0 g (98%) of amine.
8) To a stirred solution of the product of step 7 (5.0 g, 13.6 mmol) in Et$_2$O (200 ml) is added 10% NaOH (50 ml) and BOC$_2$O, and the mixture is stirred at RT overnight. The layers are separated and the organic layer is washed with brine, dried, concentrated and chromatographed with 20% EtOAc/hexanes to yield 5.1 g (79%) of the desired product.
9) To a stirred solution of the product of step 8 (1.5 g, 3.22 mmol) in CH$_3$OH (50 ml) is added sodium acetate (5.0 g, 47 mmol) and O-Methyl hydroxylamine hydrochloride and the mixture is stirred at RT for 24 h. The resulting mixture is then poured into aqueous NaOH and extracted with CH$_2$Cl$_2$. The combined extracts are dried, concentrated and chromatographed to yield 1.5 g (94%) of oxime as a mixture of E and Z isomers.
10) To a stirred solution of the product of step 9 (1.5 g, 3.0 mmol) in CH$_2$Cl$_2$ (10 ml) is added TFA (3 mL) and the mixture is stirred at RT for 2 h. The reaction mixture is concentrated and poured into 10% NaOH and extracted with CH$_2$Cl$_2$. The combined extracts are dried concentrated to afford 1.2 g (100%) of amine.
11) To stirred solution of the product of step 10 (1.3 g, 3.2 mmol) in CH$_2$Cl$_2$ is added 2,6-dimethylbenzoic acid (0.74 g, 4.96 mmol), EDCl (0.94 g, 4.94 mmol), DIPEA (0.84 g, 6.58 mmol) and HOBT (0.66g, 4.94 mmol) and the mixture is stirred for 12 h at RT. The reaction mixture is quenched with NaHCO$_3$ and extracted with CH$_2$Cl$_2$. The combined extracts are dried and concentrated to yield 1.6 g of oxime as a mixture of E and Z isomers. The isomers are separated by chromatography by eluting with CH$_2$Cl$_2$:Et$_2$O (4:1) to afford 0.77 g of E isomer and 0.49 g of Z isomer.

E isomer: 300 MHz-$^1$H NMR (CDCl$_3$) δ 7.5 (d, 2H), 7.23 (m, 2H), 7.10 (m, 1H), 6.90 (d, 2H), 4.03 (m, 1H), 3.90 (s, 3H), 3.55 (m, 1H), 3.20 (m, 3H), 3.00 (m, 3H), 2.82 (m, 1H), 2.24 (s, 3H), 2.23 (s, 3H), 2.15 (m, 3H), 1.80–1.20 (m, 5H), 0.92 (s, 3H); MS FAB+observed=526.2070; estimated=526.2069.

Z isomer: 300 Mhz-$^1$H NMR (CDCl$_3$) δ 7.50 (d, 2H), 7.15 –6.95 (m, 5H), 4.15 (m, 1H), 3.80 (s, 3H), 3.45 (s, 3), 3.25 (s, 3H), 3.00 (m, 2H), 2.24 (s, 3H), 2.25 (s, 3H), 2.10 (m, 2H), 1.80–1.50 (m, 7H), 0.92 (s, 3H); MS FAB+observed=526.2072; estimated=526.2069.

The following compounds were prepared via similar methods:

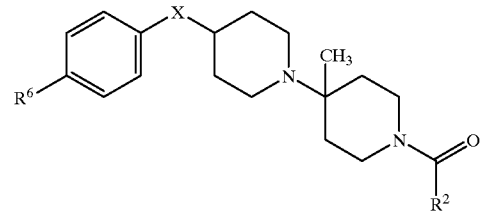

wherein X, R$^6$ and R$^2$ are as defined in the table:

| Ex. | R$^6$ | X | R$^2$ | HRMS (MH$^+$) found |
|---|---|---|---|---|
| 5A (mixture E/Z) | Br | N-OCH$_3$, =C— | 2-methyl-6-amino phenyl (H$_3$C, NH$_2$) | 529.1017 |
| 5B (mixture E/Z) | Br | N-OCH$_3$, =C— | 2-chloro-6-amino phenyl (Cl, NH$_2$) | 549.1023 |

-continued
| Ex. | R⁶ | X | R² | HRMS (MH⁺) found |
|---|---|---|---|---|
| 5C | Br | 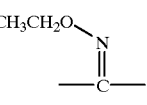 | 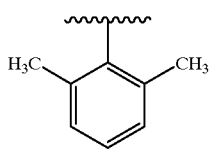 | 542.2210 |
| 5D | Br | 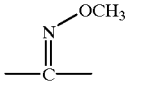 | 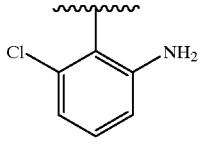 | 549.1011 |
| 5E | Br | 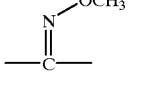 | 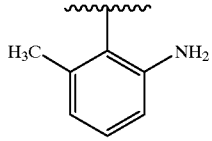 | 529.1128 |
| 5F | Br | 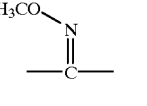 | 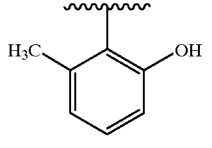 | 530.1020 |
| 5G | Br | 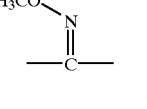 | 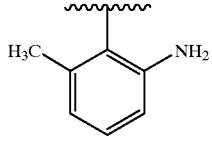 | 529.1017 |
| 5H | Br | 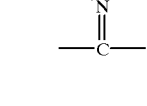 | 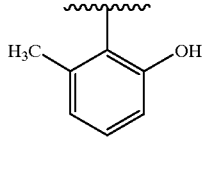 | 542.1997 |
| 5I | Br | 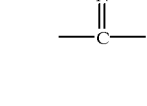 | 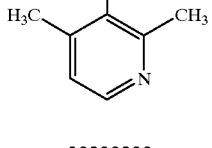 | 541.2178 |
| 5J | Br | 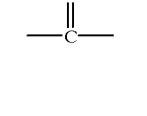 | 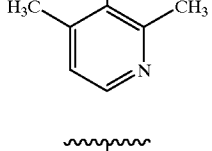 | 527.2787 |
| 5K | Br | 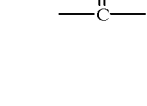 | 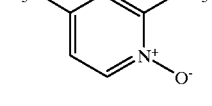 | 543.1000 |

-continued

| Ex. | R⁶ | X | R² | HRMS (MH⁺) found |
|---|---|---|---|---|
| 5L | Br | H₃CO-N=C (methoxyimino) | 4,6-dimethylpyrimidin-5-yl | 528.1971 |
| 5M | Br | CH₃CH₂O-N=C (ethoxyimino) | 2,4-dimethylpyridin-3-yl | 541.2194 |
| 5N | Br | CH₃CH₂O-N=C (ethoxyimino) | 4,6-dimethylpyrimidin-5-yl | 542.2132 |
| 5O | Br | CH₃CH₂O-N=C (ethoxyimino) | 3,5-dichloropyridin-4-yl | 583.1061 |
| 5P | Br | CF₃CH₂O-N=C | 2,4-dimethylpyridin-3-yl | 595.1895 |
| 5Q | Br | CF₃CH₂O-N=C | 4,6-dimethylpyrimidin-5-yl | 596.1831 |
| 5R | Br | CH₃CH₂O-N=C | 3,5-dimethylpyridin-4-yl | 541.2188 |
| 5S | Br | CH₃CH₂O-N=C | 3,5-dichloropyridin-4-yl N-oxide | 597.4911 |
| 5T | Br | H₃CO-N=C | 3,5-dichloropyridin-4-yl | 569.0909 |

-continued

| Ex. | R⁶ | X | R² | HRMS (MH⁺) found |
|---|---|---|---|---|
| 5U | Br | CH₃(CH₂)₂O−N=C− | 2,4-dimethylpyridine N-oxide (attached at 3-position) | 571.2270 |
| 5V | Br | CH₃(CH₂)₂O−N=C− | 4,6-dimethylpyrimidine (attached at 5-position) | 556.2291 |
| 5W | Br | CH₃CH₂O−N=C− | 3,5-dimethylpyridine N-oxide (attached at 4-position) | 557.2119 |
| 5X | Br | CH₃CH₂O−N=C− | 2,4-dimethyl-6-hydroxypyridine (attached at 3-position) | 557.2124 |
| 5Y | Br | (CH₃)₂CHCH₂−O−N=C− | 4,6-dimethylpyrimidine (attached at 5-position) | 570.2454 |
| 5Z | Br | CH₃CH₂O−N=C− | 3,5-dibromopyridine (attached at 4-position) | 671.0058 |
| 5AA | Br | cyclopropyl-CH₂−O−N=C− | 4,6-dimethylpyrimidine (attached at 5-position) | 568.2286 |
| 5BB | Br | (CH₃)₂CH−O−N=C− | 4,6-dimethylpyrimidine (attached at 5-position) | 556.2286 |

-continued

| Ex. | R⁶ | X | R² | HRMS (MH⁺) found |
|---|---|---|---|---|
| 5CC | Br | H₃CO-N=C- | 4,6-dimethylpyrimidin-5-yl | 527.2015 |
| 5DD | Br | CH₃CH₂O-N=C- | 2-bromophenyl | 592.1000 |
| 5EE | Br | H₃CO-N=C- | 3,5-dibromopyridin-4-yl | 656.9889 |
| 5FF | Br | CH₃CH₂O-N=C- | 3,5-dibromopyridin-4-yl N-oxide | 686.9989 |
| 5GG | Br | CH₃CH₂O-N=C- | 2,4,6-trimethylpyrimidin-5-yl | 556.2290 |
| 5HH | F₃C— | CH₃CH₂O-N=C- | 2,4,6-trimethylpyrimidin-5-yl | 546.3056 |
| 5II | F₃C— | CH₃CH₂O-N=C- | 3,5-dimethylpyridin-4-yl | 531.2956 |
| 5JJ | F₃C— | CH₃CH₂O-N=C- | 3,5-dimethylpyridin-4-yl N-oxide | 547.2902 |

-continued
| Ex. | R⁶ | X | R² | HRMS (MH⁺) found |
|---|---|---|---|---|
| 5KK | F₃C— |  | 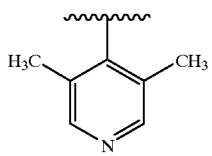 | 517.2812 |
| 5LL | Br | 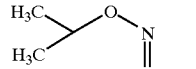 | 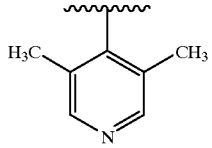 | 555.2336 |
| 5MM | Br | 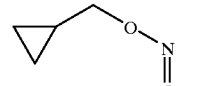 | 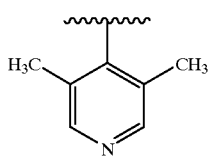 | 567.2327 |
| 5NN | Br |  | 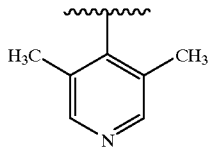 | 555.2341 |
| 5OO | Br |  | 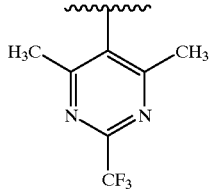 | 610.2016 |
| 5PP | F₃CO— |  | 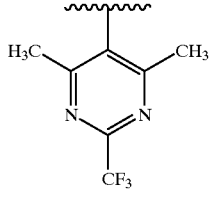 | 616.2746 |
| 5QQ | F₃C— |  | 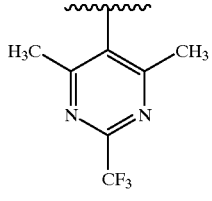 | 600.2788 |
| 5RR | Br |  | 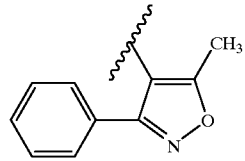 | 593.2131 |

-continued

| Ex. | R⁶ | X | R² | HRMS (MH⁺) found |
|---|---|---|---|---|
| 5SS | Br | CH₃CH₂O-N=C- | 4,6-dimethyl-2-(methylthio)pyrimidin-5-yl | 590.1995 |
| 5TT | Br | CH₃CH₂O-N=C- | 3-(2-chlorophenyl)-5-methylisoxazol-4-yl | 627.1729 |
| 5UU | Br | CH₃CH₂O-N=C- | 4-hydroxy-2,6-dimethylphenyl | 556.218 |
| 5VV | Br | H₃CO-N=C- | 4-hydroxy-2,6-dimethylphenyl | 542.2002 |
| 5WW | Br | CH₃CH₂O-N=C- | 4-amino-2,6-dimethylphenyl | 555.2336 |
| 5XX | Br | CH₃CH₂O-N=C- | 4-(NHBOC)-3,5-dimethylphenyl | 655.287 |
| 5YY | Br | CH₃CH₂O-N=C- | 1-(4-methylphenyl)cyclopropyl | 566.2407 |

-continued

| Ex. | R⁶ | X | R² | HRMS (MH⁺) found |
|---|---|---|---|---|
| 5ZZ | Br | H₃CO-N=C- | 3,5-dimethyl-4-(pyridin-4-yl)phenyl | 603.2349 |
| 5AB | Br | CH₃CH₂O-N=C- | 3,5-dimethyl-4-(pyridin-4-yl)phenyl | 617.2488 |
| 5AC | Br | CH₃CH₂O-N=C- | 3,5-dimethyl-4-(NHC(O)NH-iPr)phenyl | 640.2868 |

Additional data for compounds of Example 5:

| Ex. | ¹H—NMR (300 MHz ¹H NMR (CDCl₃)) |
|---|---|
| 5J | 7.50 (d, 2H), 7.15–6.95 (m, 5H), 4.15 (m, 1H), 3.80 (s, 3H), 3.45 (s, 3H), 3.25 (s, 3H), 3.00 (m, 2H), 2.24 (s, 3H), 2.25 (s, 3H), 2.10 (m, 2H), 1.80–1.50 (m, 7H), 0.92 (s, 3H) |
| 5L | 8.95 (s, 1H), 7.53 (d, J=8.4 Hz, 2H), 7.10 (d, J=8.4 Hz, 2H), 4.24 (m, 1H), 3.81 (s, 3H), 3.98 (m, 2H), 2.75–3.00 (m, 3H), 2.48 (s, 3H), 2.45 (s, 3H), 1.99–2.20 (m, 4H), 1.73 (m, 3H), 1.20–1.62 (m, 4H), 0.94 (s, 3H) |
| 5N | 8.92 (s, 1H), 7.45 (d, J=9.0 Hz, 2H), 7.10 (d, J=8.7 Hz, 2H), 4.21 (m, 1H), 4.02 (q, J=6.9 Hz, 2H), 3.98 (m, 2H), 2.75–2.92 (m, 3H), 2.46 (s, 3H), 2.41 (s, 3H), 1.90–2.20 (m, 4H), 1.73 (m, 3H), 1.27–1.62 (m, 4H), 1.15 (t, J=8.1 Hz, 3H), 0.93 (s, 3H) |

EXAMPLE 6

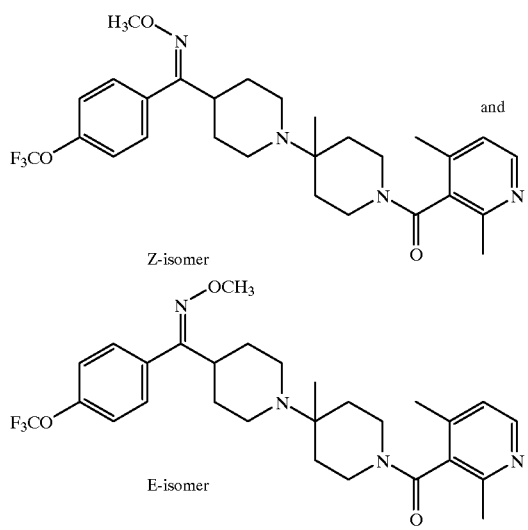

Z-isomer

E-isomer and

A) Preparation of Intermediate 27 (Scheme 8 (R$^1$= CH$_3$))

1) 23 (40.0 g, 0.203 mol) is vigorously stirred in EtOAc (200 ml) and concentrated aqueous HCl (80 ml) for 1.5 h. The solution is concentrated, diluted with Et$_2$O (300 ml) and H$_2$O (150 ml), the aqueous layer is separated and the organic layer is extracted once with H$_2$O (20 ml). Combined aqueous layers are concentrated and the residue is dried 24 h under high vaccum to provide 26.7 g (84%) of a white solid. To this hydrochloride and N-tert-butoxycarbonyl-4-piperidone (43.8 g, 0.22 mol) in anhydrous ClCH$_2$CH$_2$Cl (80 mL) with 4 Å molecular sieves, are successively added DBU (33.2 ml, 0.22 mol) and titanium(IV) isopropoxide (65.5 ml, 0.22 mol) at 0° C., the reaction mixture is allowed to warm to RT and is stirred overnight at RT. The mixture is then cooled to 0° C. and diethylaluminum cyanide, 1 N in toluene (260 ml, 0.26 mol) is added with vigorous stirring. The reaction is allowed to warm to RT and stirred an additional 3 h, after which are added CH$_2$Cl$_2$ (300 ml), EtOAc (300 ml), and Celite (50 g). The reaction mixture is cooled to 0° C., water (40 ml) is added slowly with vigorous stirring and, after an additional 5 min. stirring at RT, the excess of water is quenched with Na$_2$SO$_4$. The final mixture is then filtered over Celite, evaporated and subjected to flash chromatography over silica gel (eluting with Hexanes/EtOAc, 8:2), to provide 50.3 g (83%) of 24 as a colorless oil which solidifies upon standing.

2) To a solution of 24 (27.7 g, 90.6 mmol) in anhydrous THF (200 mL) at 0° C. is slowly added CH$_3$MgBr 3 M in Et$_2$O (91 ml, 3 equiv.) with vigorous stirring. After the addition, the reaction is allowed to warm to RT and stirred 3 h. The reaction is then poured into aqueous saturated NH$_4$Cl, extracted with Et$_2$O (4 times), washed with brine, dried over Na$_2$SO$_4$, and concentrated to give 27.1 g (100%) of 25 as a colorless oil.

3) To a solution of 25 (11.6 g, 39.3 mmol) in anhydrous THF (50 ml) at 0° C. is slowly added BH$_3$.S(CH$_3$)$_2$ 2 N in THF (14 ml, 28 mmol) and the solution is stirred 2 days at RT. The final mixture is concentrated to ca. 50 ml and slowly poured into ice-cooled EtOH/THF 1:1 (50 ml). After 15 min. at 0° C., 50 ml of a pH 7 buffer solution are added, followed slowly by 30% H$_2$O$_2$ aqueous solution (50 ml). The reaction mixture is stirred overnight at RT, diluted with 1 N NaOH and extracted with CH$_2$Cl$_2$. Combined organic layers are dried over Na$_2$SO$_4$, concentrated, then subjected to flash chromatography over silica gel (eluting with EtOAc/EtOH, 8:2) to yield 9.69 g (79%) of 26 as a colorless oil.

4) A solution of 26 (11.2 g, 35.8 mmol) and N-methylmorpholine N-oxide (4.67 g, 39.4 mmol) in anhydrous CH$_2$Cl$_2$ (100 ml) is stirred 1 h at RT, cooled to 0° C., and TPAP (885 mg) is added portionwise. The reaction is allowed to warm to RT and stirred 1 h. Additional N-methyl-morpholine N-oxide (1.30 g, 11 mmol) and TPAP (300 mg) are then added to drive the reaction to completion after 1 h. The reaction mixture is filtered over Celite, concentrated, then subjected to flash chromatography over silica gel (eluting with CH$_2$Cl$_2$/acetone, 8:2 to 7:3) to provide 5.91 g (53%) of 27 as a yellow oil.

B) Preparation of Title Compounds of Example 6

1) A solution of 1-bromo-4-(trifluoromethoxy)-benzene (4.20 ml, 28.0 mmol) in anhydrous THF (100 mL) is cooled to −78° C. and n-BuLi 2.5 N in hexanes (11.2 ml, 28.0 mmol) is added via syringe. The reaction mixture is allowed to warm to −50° C. for 10 min, cooled to −78° C., and a solution of aldehyde 27 (6.20 g, 20.0 mmol) in anhydrous THF (15 ml) is added dropwise. After stirring 30 min at −78° C., then 30 min at −20° C., the solution is poured into half-brine and extracted with CH$_2$Cl$_2$ (3×100 ml). Combined organic layers are dried over Na$_2$SO$_4$, and concentrated to give 8.85 g (94%) of an alcohol as a yellow oil.

2) To a solution of the product of step 1 (8.85 g, 39.3 mmol) in CH$_2$Cl$_2$ (100 ml) at 0° C. is added Dess-Martin periodinane (19.70 g, 2.5 equiv.) and the reaction mixture is stirred 2 h at RT. An additional 8.0 g of Dess-Martin periodinane is added and the reaction is stirred for an additional 4 h. The solution is poured into a 1:1 mixture of aqueous saturated NaHCO$_3$ and aqueous saturated Na$_2$S$_2$O$_3$ (200 ml), stirred 10 min, extracted with CH$_2$Cl$_2$, and dried over Na$_2$SO$_4$. The residue obtained after concentration of the solvents is purified by flash chromatography over silica gel (eluting with hexanes/EtOAc, 7:3) to yield 5.48 g (63%) of the ketone as a yellow oil.

3) A solution of the product of step 2 (2.85 g, 6.05 mmol), HONH$_2$.HCl (2.08 g, 30 mmol), and AcONa (2.46 g, 30 mmol) in EtOH (50 mL) is heated at reflux under N$_2$ for 4 h. After evaporation of the solvent, the residue is taken up in aqueous 0.1 N NAOH and extracted with CH$_2$Cl$_2$. The residue obtained after evaporation of the solvents is subjected to flash chromatography over silica gel, to afford first the E-hydroxime (eluting with CH$_2$Cl$_2$/EtOAc, 7:3; 0.84 g; 29%), then the Z-hydroxime (eluting with CH$_2$Cl$_2$/EtOAc 1:1; 1.10 g; 37%), both products as white solids.

4) To a suspension of Z-hydroxime (0.89 g, 1.84 mmol) in anhydrous DMF (5 ml) is slowly added KHMDA 0.5 N in toluene (4.0 ml, 2.02 mmol) at 0° C., leading to the appearance of a yellow solution. After 2 min. at this temperature, dimethylsulfate (350 μl, 3.7 mmol) is slowly added and the solution is allowed to warm to RT and stirred 1 h. The mixture is poured into aqueous 0.1 N NaOH, extracted with CH$_2$Cl$_2$, and dried over Na$_2$SO$_4$. The residue obtained after concentration of the solvents is purified by flash chromatography over silica gel (eluting with hexanes/EtOAc, 75:25) to afford 0.55 g (62%) of the Z-methoxime as a slightly yellow oil.

5) A solution of Z-methoxime (0.59 g, 1.18 mmol) in anhydrous CH$_2$Cl$_2$ (6 ml) and TFA (3 ml) is stirred 1 h at RT. After concentration, the residue is taken up in aqueous 1 N NaOH, extracted with CH$_2$Cl$_2$, dried over Na$_2$SO$_4$ and concentrated to give 0.47 g (100%) of the free amine as a white foam.

6) A solution of the product of step 5 (470 mg, 1.18 mmol), 2,4-dimethylnicotinic acid (220 mg, 1.45 mmol), DEC (280 mg, 1.45 mmol), HOBT (243 mg, 1.80 mmol) and N-methylmorpholine (0.33 ml, 3.0 mmol) in anhydrous DMF is stirred 14 h. After concentration, the residue is taken up in aqueous 0.1 N NaOH, extracted with CH$_2$Cl$_2$, and dried over $Na_2SO_4$. The residue obtained after concentration of the solvent is purified by flash chromatography over silica gel (eluting with $CH_2Cl_2$/acetone, 7:3 to 1:1) to afford 640 mg (100%) of a colorless oil.

$^1$H-NMR (400 MHz, $CDCl_3$) δ 8.35 (d, J=7.8 Hz, 1H), 7.25 (AB system, 4H), 6.98 (d, J=7.8 Hz, 1H), 4.22 (m, 1H), 3.82 (s, 3H), 3.43 (m, 1H), 3.33 (m, 1H), 2.99 (m, 2H), 2.85 (m, 1H), 2.49 (s, 3H, atropisomer a) and 2.51 (s,3H, atropisomer b), 2.26 (s, 3H, atropisomer a) and 2/28 (s, 3H, atropisomer b), 1.95–2.21 (m, 3H), 1.20–1.90 (m, 7H), 0.92 (s, 3H). HRMS (M+H$^+$) 533.2747.

Following steps B-4, B-5, and B-6 using the E-oxime yields the corresponding E-methoxime product.

The following compounds are prepared via similar procedures:

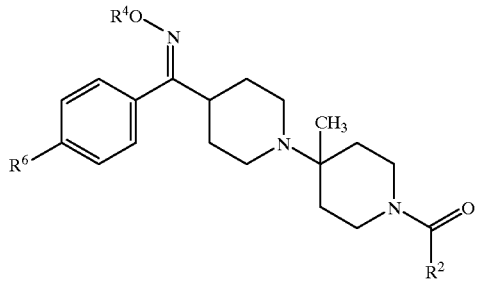

wherein $R^4$, $R^6$ and $R^2$ are as defined in the table:

| Ex. | $R^6$ | $R^4$ | $R^2$ | HRMS (MH$^+$) found |
|---|---|---|---|---|
| 6A | Br | isopropyl | 2,6-dimethylphenyl | 554.3000 |
| 6B | Br | isopropyl | 2,4-dimethylpyridin-3-yl | 555.2335 |
| 6C | Br | isopropyl | 3-methyl-2-hydroxyphenyl | 556.2175 |
| 6D | Br | 2-methoxyethyl | 2,4-dimethylpyridin-3-yl | 571.2284 |
| 6E | Br | 2-methoxyethyl | 2,6-dimethylphenyl | 570.2331 |
| 6F | Br | cyclopropylmethyl | 2,4-dimethylpyridin-3-yl | 569.1000 |
| 6G | $F_3CO-$ | 2,2,2-trifluoroethyl | 2,4-dimethylpyridin-3-yl | 601.2628 |

-continued

| Ex. | R⁶ | R⁴ | R² | HRMS (MH⁺) found |
|---|---|---|---|---|
| 6H | F₃CO— | F₃C-CH₂-CH₂- (wavy) | 3,5-dimethyl-4-oxyphenyl (H₃C, CH₃, O) | 617.2549 |
| 6I | F₃CO— | —CH₃ | 3,5-dimethylpyrimidin-4-yl (H₃C, CH₃, N, N) | 534.2708 |
| 6J | F₃CO— | F₃C-CH₂-CH₂- | 3-methyl-2-hydroxyphenyl (H₃C, OH) | 602.2465 |
| 6K | F₃CO— | F₃C-CH₂-CH₂- | 3,5-dimethylpyrimidin-4-yl (H₃C, CH₃, N, N) | 602.2579 |
| 6L | F₃CO— | cyclopropyl-CH₂- | 3,5-dimethyl-4-oxyphenyl (H₃C, CH₃, O) | 589.3013 |
| 6M | Cl | CH₃CH₂— | 3,5-dimethylpyridin-4-yl N-oxide (H₃C, CH₃, N→O) | 513.2633 |
| 6N | Cl | CH₃— | 2,4-dimethylpyridin-3-yl (H₃C, CH₃, N) | 483.2516 |
| 6O | F₃C— | CH₃— | 3,5-dimethyl-4-oxyphenyl (H₃C, CH₃, O) | 533.2758 |
| 6P | Cl | CH₃CH₂— | 2,4-dimethylpyridin-3-yl (H₃C, CH₃, N) | 497.2683 |

-continued
| Ex. | R⁶ | R⁴ | R² | HRMS (MH⁺) found |
|---|---|---|---|---|
| 6Q | Cl | CH₃CH₂— | 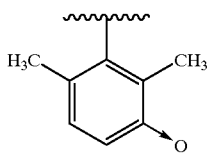 | 513.2642 |
| 6R | Cl | CH₃CH₂— | 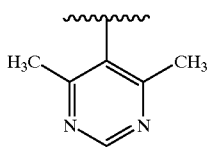 | 498.2633 |
| 6S | F₃C— | CH₃— | 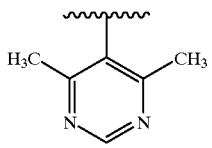 | 518.2749 |
| 6T | Cl | CH₃CH₂— | 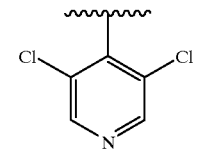 | 537.1603 |
| 6U | F₃C— | CH₃— | 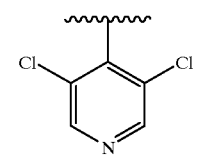 | 557.1680 |
| 6V | F₃C— | CH₃CH₂— | 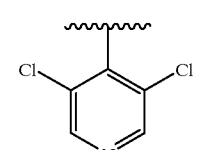 | 571.1838 |
| 6W | Cl | CH₃CH₂— | 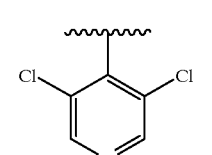 | 555.8401 |
| 6X | Cl | CH₃CH₂— | 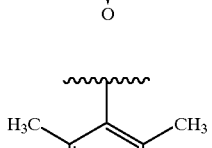 | 497.2682 |

-continued

| Ex. | R⁶ | R⁴ | R² | HRMS (MH⁺) found |
|-----|-----|-----|-----|-----|
| 6Y | F₃CO— | CH₃— | 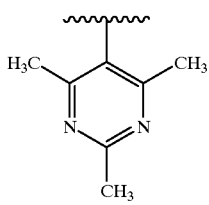 | 548.2853 |
| 6Z | F₃CO— | CH₃CH₂— | 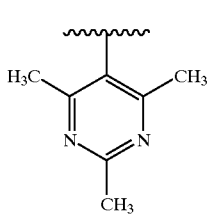 | 562.3017 |
| 6AA | F₃CO— | CH₃CH₂— | 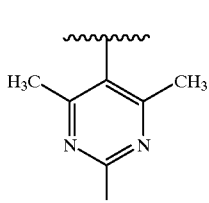 | 563.2939 |

Additional data for compounds of Example 6:

| Ex. | ¹H—NMR (300 MHZ ¹H NMR (CDCl₃)) |
|-----|-----|
| 6F | 8.31 (d, 1H), 7.51 (d, 2H), 7.10 (d, 2H), 6.95 (d, 2H), 4.20 (m, 2H), 3.40 (d, 2H), 3.30 (m, 2H), 3.35 (m, 3H), 2.80–3.05 (m, 5H), 2.45 (d, 3H), 2.25 (d, 3H), 1.25–2.20 (m, 10H), 0.50 (m, 2 H), 0.22 (m, 2H), 0.90 (s, 3H) |
| 6G | 8.34 (d, J=5.1 Hz, 1H), 7.24 (br s, 4H), 6.96 (d, J=5.1 Hz, 1H), 4.33 (q, J=8.6 Hz, 2H), 4.13 (m, 1H), 3.45 (m, 1H), 3.30 (m, 1H), 2.98 (m, 2H), 2.82 (m, 1H), 2.46 and 2.49 (s, 3H), 2.41 (m, 1H), 2.24 and 2.27 (s, 3H), 2.10 (m, 2H), 1.96 (m, 1H), 1.15–1.90 (m, 7H), 0.92 (s, 3H) |
| 6I | 8.92 (s, 1H), 7.23 (br s, 4H), 4.11 (m, 1H), 3.79 (s, 3H), 3.30–3.45 (m, 2H), 2.97 (m, 2H), 2.81 (m, 1H), 2.45 and 2.42 (s, 6H), 2.40 (m, 1H), 1.90–2.20 (m, 3H), 1.15–1.90 (m, 7H), 0.92 (s, 3H) |

EXAMPLE 7

Alternate Synthesis of the Compounds of Example 6

1) The product of Example 6, step B-2 (566 mg, 1.20 mmol) is treated with H₃CONH₂.HCl using conditions similar to those shown in Example 6, step B-3. The resulting crude mixture of Z- and E-methoximes is separated on a preparative silica gel TLC plate (eluting with hexanes/ EtOAc, 80:20) to afford, in order of elution, first the E-methoxime (175 mg; 29%), then the Z-methoxime (175 mg; 29%), both products as oils.

2) The Z-methoxime (75 mg; 0.15 mmol) of step 1 is deprotected following conditions similar to those shown in Example 6, step B-5 and the resulting free amine (46 mg) is directly subjected to amidation with 2,4-dimethyinicotinic acid using conditions similar to those shown in Example 6, step B-6 to yield 50 mg (82%) of a colorless oil.

The following compounds are prepared via similar procedures:

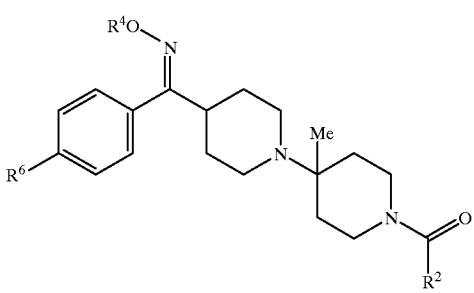

wherein R⁴, R⁶ and R² are as defined in the table:

| Ex. | R⁶ | R⁴ | R² | HRMS (MH⁺) found |
|---|---|---|---|---|
| 7A | F₃CO— | CH₃— | 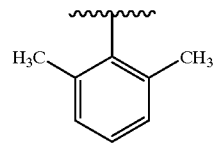 | 532.2795 |
| 7B | F₃CO— | CH₃— | 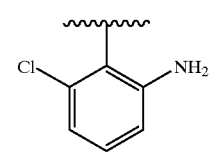 | 553.2192 |
| 7C | F₃CO— | CH₃— | 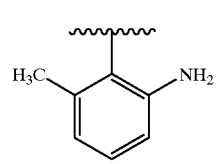 | 533.2730 |
| 7D | F₃CO— | CH₃CH₂— | 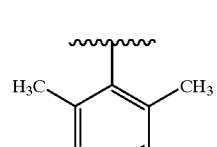 | 546.2940 |
| 7E | F₃C— | CH₃— | 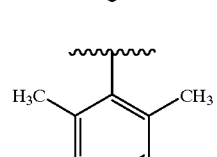 | 516.2833 |
| 7F | F₃CO— | CH₃— | 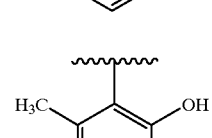 | 534.2571 |
| 7G (E isomer) | F₃C— | CH₃— | 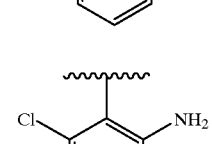 | 537.2234 |
| 7H | F₃C— | CH₃— | 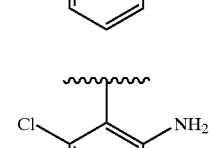 | 537.2234 |
| 7I | F₃C— | CH₃— | 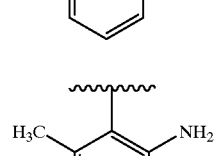 | 537.2234 |

-continued

| Ex. | R$^6$ | R$^4$ | R$^2$ | HRMS (MH$^+$) found |
|---|---|---|---|---|
| 7J | F$_3$CO— | CH$_3$CH$_2$— | 2-chloro-6-aminophenyl | 567.2362 |
| 7K | F$_3$C— | CH$_3$— | 2,4-dimethylpyridin-3-yl | 517.2812 |
| 7L | F$_3$C— | CH$_3$CH$_2$— | 3-methyl-2-hydroxyphenyl | 532.2787 |
| 7M | F$_3$CO— | CH$_3$CH$_2$— | 2,4-dimethylpyridin-3-yl | 547.2888 |
| 7N | F$_3$CO— | cyclopropylmethyl | 2,6-dimethylphenyl | 572.3093 |
| 7O | F$_3$CO— | CH$_3$CH$_2$— | 3-methyl-2-hydroxyphenyl | 548.2732 |
| 7P (E isomer) | F$_3$C— | CH$_3$— | 2,4-dimethylpyridin-3-yl | 517.2831 |
| 7Q | F$_3$CO— | CH$_3$— | 2,6-dimethylpyridin-N-oxide | 549.2686 |
| 7R | F$_3$CO— | CH$_3$CH$_2$— | 3-methyl-2-acetoxyphenyl | 590.2854 |

-continued

| Ex. | R⁶ | R⁴ | R² | HRMS (MH⁺) found |
|---|---|---|---|---|
| 7S | F₃C— | CH₃CH₂— | 2,4-dimethylpyridin-3-yl | 531.1002 |
| 7T | F₃C— | CH₃CH₂— | 2,5-dimethyl-3-oxidophenyl | 547.1348 |
| 7U (E isomer) | F₃CO— | CH₃— | 2,6-dimethylphenyl | 532.2784 |
| 7V | F₃CO— | H₃COCH₂CH₂— | 2,6-dimethylphenyl | 576.3049 |
| 7W | F₃CO— | CH₃CH₂— | 2,5-dimethyl-3-oxidophenyl | 563.2855 |
| 7X | F₃CO— | cyclopropylmethyl | 2,4-dimethylpyridin-3-yl | 573.3052 |
| 7Y | F₃CO— | cyclopropylmethyl | 3-methyl-2-hydroxyphenyl | 574.2889 |
| 7Z | F₃CO— | CF₃CH₂— | 3,5-dichloropyridin-4-yl | 641.1537 |
| 7AA | F₃CO— | CH₃— | 3,5-dichloropyridin-4-yl | 573.1638 |

-continued

| Ex. | R⁶ | R⁴ | R² | HRMS (MH⁺) found |
|---|---|---|---|---|
| 7BB | F₃CO— | CH₃CH₂— | 3,5-dichloropyridin-4-yl | 587.1821 |
| 7CC | F₃CO— | CH₃CH₂— | 4,6-dimethylpyrimidin-5-yl | 548.2861 |
| 7DD | F₃CO— | CH₃— | 3,5-dichloropyridin-4-yl N-oxide | 589.1610 |
| 7EE | F₃CO— | CH₃CH₂— | 3,5-dichloropyridin-4-yl N-oxide | 603.1748 |
| 7FF | F₃CO— | CH₃(CH₂)₂— | 4,6-dimethylpyrimidin-5-yl | 562.3030 |
| 7GG | F₃CO— | CH₃(CH₂)₂— | 3,5-dichloropyridin-4-yl N-oxide | 617.1918 |
| 7HH | F₃CO— | CH₃(CH₂)₂— | 2,6-dimethylphenoxy | 577.3019 |

Additional data for compounds of Example 7:

| Ex. | ¹H—NMR (300 MHz ¹H NMR (CDCl₃)) |
|---|---|
| 7H | 7.55 (d, 2H), 7.30 (d, 2H), 7.15 (t, 1H), 6.75 (d, 1H), 6.60 (d, 1H), 4.25 (m, 2H), 3.80 (s, 3H), 3.40 (m, 2H), 2.80–3.20 (m, 3H), 2.40 (m, 1H), 1.40–2.20 (m, 13H), 0.90 (s, 3H) |
| 7K | 8.31 (d, 1H), 7.61 (d, 2H), 7.31 (d, 2H), 6.95 (d, 2H), 4.30 (m, 2H), 3.80 (3, 2H), 3.20–3.50 (m, 2H), 2.75–3.05 (m, 3H), 2.45 (d, 3H), 2.25 (d, 3H), 1.45–2.20 (m, 11H), 0.92 (s, 3H) |
| 7Q | 8.11 (d, J=6.8 Hz, 1H), 7.25 (br s, 4H), 6.94 (d, J=6.8 Hz, 1H), 4.16 (m, 1H), 3.75 (s, 3H), 3.20–3.45 (m, 2H), 2.85–3.00 (m, 3H), |

| Ex. | ¹H—NMR (300 MHz ¹H NMR (CDCl₃)) |
|---|---|
| | 2.41 (d, J=11.6 Hz, 3H), 2.45 (m, 1H), 2.20 (d, J=11.6 Hz, 3H), 1.85–2.20 (m, 3H), 1.15–1.85 (m, 7H), 0.88 (s, 3H) |
| 7R | 7.13–7.30 (m, 5H), 7.14 (m, 1H), 6.95 (m, 1H), 4.13 (m, 1H), 4.03 (q, J=7.1 Hz, 2H), 3.15–3.50 (m, 2H), 2.86–3.10 (m, 2H), 2.80 (m, 1H), 2.39 (m, 1H), 2.15–2.30 (m, 6H), 1.85–2.15 (m, 3H), 1.10–1.85 (m, 7H), 1.28 (t, J=7.1 Hz, 3H), 0.88 (br s, 3H) |
| 7S | 8.31 (d, 1H), 7.61 (d, 2H), 7.32 (d, 2H), 6.95 (d, 2H), 4.25 (m, 2H), 4.05 (q, 2H), 3.20–3.50 (m, 2H), 2.80–3.15 (m, 3H), 2.45 (d, 3H), 2.25 (d, 3H), 1.45–2.20 (m, 9H), 1.20 (t, 3H), 0.90 (s, 3H) |

EXAMPLE 8

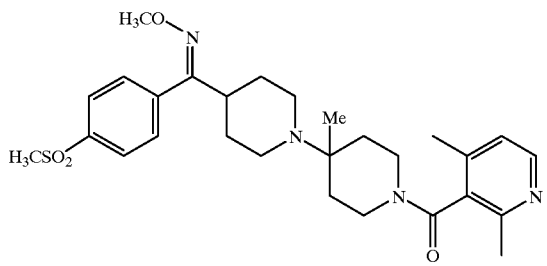

1) To a stirred solution of the product of Example 5, step 8 (0.500 g, 1.07 mmol) in DMF (25 ml) is added sodium methylmercaptide (0.113 g, 1.62 mmol) and the mixture is heated to 70° C. for 12 h. The reaction mixture is then cooled to RT, diluted with Et₂O, washed with brine, dried and concentrated to yield 0.437 g (97%) of sulfide.

2) A solution of the product of step 1 (1.00 g; 2.31 mmol), H₃CONH₂.HCl (3.80 g, 46.2 mmol), and AcONa (3.79 g, 46.2 mmol) in EtOH (30 ml) is heated at reflux under N₂ for 4 h. After evaporation of the solvent, the residue is taken up in aqueous 0.1 N NaOH and extracted with CH₂Cl₂. The residue obtained after evaporation of the solvents is subjected to flash chromatography over silica gel, to afford first the E-oxime (eluting Et₂O/CH₂Cl₂, 1:4; 0.45 g; 24%), then the Z-oxime (0.25 g, 15%).

3) To a solution of Z-oxime (0.250 g, 0.543 mmol) of step 2 in CH₃OH (5 ml) is at 0° C. is added oxone (1.00 g, 1.627 mmol in 5 ml of CH₃OH) and the mixture is stirred at 0° C. for 4 h. The reaction is then quenched with 10% NaOH, concentrated, poured into water (1 0 ml) and extracted with CH₂Cl₂, dried and concentrated to yield 0.220 g (82%) of sulfone.

4) To a stirred solution of the product of step 3 (0.300 g, 0.608 mmol) in CH₂Cl₂ (5 ml) is added TFA(1 ml) and the mixture is stirred at RT for 2 h. The reaction mixture is concentrated, poured into 10% NaOH and extracted with CH₂Cl₂. The combined extracts are dried and concentrated to afford 0.240 g (100%) of amine.

5) To stirred solution of the product of step 4 (0.45 g, 0.114 mmol) in CH₂Cl₂ is added 2,6-dimethyinicotinic acid (0.26 g, 0.172 mmol), DEC (0.33 g, 0.172 mmol), N,N,N-diisopropylethylamine (DIPEA) (0.2 ml) and HOBT (0.249, 0.172 mmol) and the mixture is stirred for 12 h at RT. The reaction mixture is quenched with NaHCO₃, extracted with CH₂Cl₂, dried, concentrated and purified by preparative chromatography (20% EtOH/EtOAc) to afford 0.046 g (76%) of Z-oxime amide.

300 MHz-¹H NMR (CDCl₃) δ 8.32 (d, 1H), 7.95 (d, 2H), 7.40 (d, 2H), 6.95 (d, 1H), 4.20 (m, 1H), 3.82 (s, 3H), 3.30–3.45 (m, 3H), 3.10 (s, 3H), 2.80–3.00 (m, 3H), 2.50 (d, 2H), 2.25 (d, 2H), 1.30–2.20 (m, 12H), 0.92 (s, 3H).

The following compounds were prepared in a similar manner:

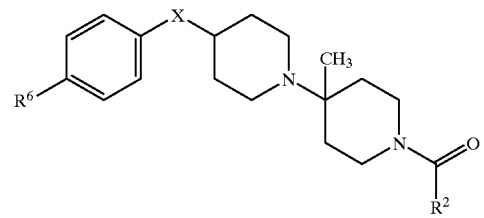

wherein X, R⁶ and R² are as defined in the table:

| Ex. | R⁶ | X | R² | HRMS (MH⁺) found |
|---|---|---|---|---|
| 8A (mixture E/Z) | O=S(=O)(CH₃)– | =N–OCH₃ | 2,6-dimethylphenyl | 526.2753 |
| 8B | O=S(=O)(CH₃)– | =N–OCH₃ | 2-Cl-6-NH₂-phenyl | 547.2135 |
| 8C | Br | =N–OCH₃ | 2-Cl-6-NH₂-phenyl | 549.2133 |

-continued

| Ex. | R⁶ | X | R² | HRMS (MH⁺) found |
|---|---|---|---|---|
| 8D | -SO₂CH₃ | CH₃CH₂O-N=C- | 3,4-dimethylpyridin-? | 541.2849 |
| 8E | -SO₂CH₃ | CH₃CH₂O-N=C- | 2,6-dimethylphenol | 557.2798 |
| 8F | -SO₂CH₃ | CH₃O-N=C- | 3,4-dimethylpyridin-? | 543.2641 |
| 8G | -SO₂CH₃ | CH₃O-N=C- | 2,6-dimethylphenol | 527.2692 |
| 8H | F₃C— | CH₃CH₂O-N=C- | 4,6-dimethylpyrimidin-5-yl | 532.2895 |
| 8I | -SO₂CH₃ | CH₃O-N=C- | 4,6-dimethylpyrimidin-5-yl | 542.2796 |

EXAMPLE 9

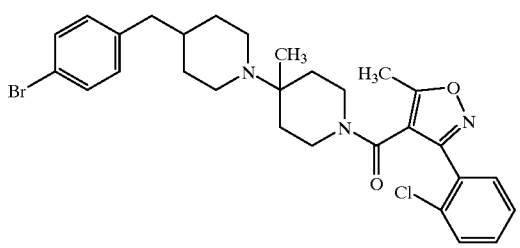

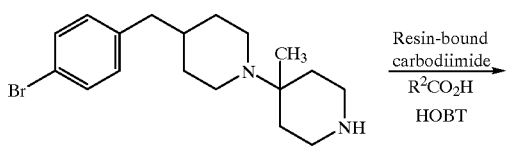

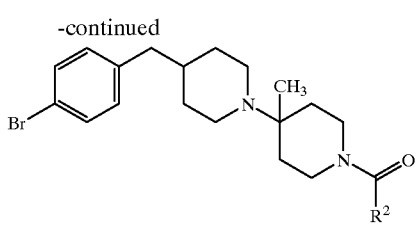

Dissolve the starting amine (2.0 g, 5.7 mmol) in CHCl₃ (57 ml; =Stock solution A~0.1 M). Add 430 µl of stock solution A (0.043 mmol) to a slurry of 0.25 g (~0.22 mmol) of resin bound cardodiimide (prepared by reacting Argopore-Cl resin with 1-(3-dimethylaminopropyl)3-ethyl carbodiimide in DMF at 100 C) in DMF (2 ml) in a polyethylene SPE cartridge. To this mixture add 0.12 ml of a 1M solution of 5-methyl-3-[2-chlorophenyl]isoxazole-4-carboxylic acid in DMF (0.12 mmol), HOBT (86 µl of a 0.5M solution in DMF) and DMAP (25 μl of a 0.05M solution in DMF). Shake this mixture for 14 h, filter and add 0.3 g of Amberlyst-15 resin (~1.5 mmol) to the filtrate. Shake for 1 to 2 h, filter and wash the resin twice with each of the following solvents: THF, CH$_2$Cl$_2$ and CH$_3$OH, then wash with THF and CH$_2$Cl$_2$. Treat the resin with 2M NH$_3$ in CH$_3$OH (1 time for 30 min, and 1 time for 5 min.). Combine and concentrate the filtrates under reduced pressure to afford the title compound. LCMS found MH$^+$=570, 572 (calculated MW 571); TLC R$_f$=0.45 (CH$_2$Cl$_2$/CH$_3$OH/NH$_4$OH (95/5/0.5)).

Using a similar procedure, the following compounds were prepared

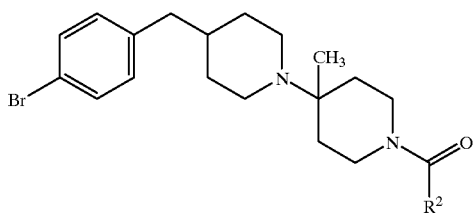

wherein R$^2$ is as defined in the table:

| Ex. | R2 | Data | TLC R$_f$ values |
|---|---|---|---|
| 9A | ![H3C-isoxazole-phenyl] | LCMS: MH$_+$ = 538.1 R$_t$ = 6.27 min | 0.58 |
| 9B | ![H3C-isoxazole-NH2] | MS m/e = 475.2, 477.2 (Electrospray) | |
| 9C | ![H3C-isoxazole-dichlorophenyl] | LCMS: MH$_+$ = 606 | 0.57 |
| 9D | ![naphthyl] | LCMS: MH$_+$ = 507.1 R$_t$ = 6.39 min | 0.49 |
| 9E | ![cyclopropyl-phenyl] | LCMS: MH$_+$ = 497.1 R$_t$ = 6.32 min | 0.48 |

EXAMPLE 10

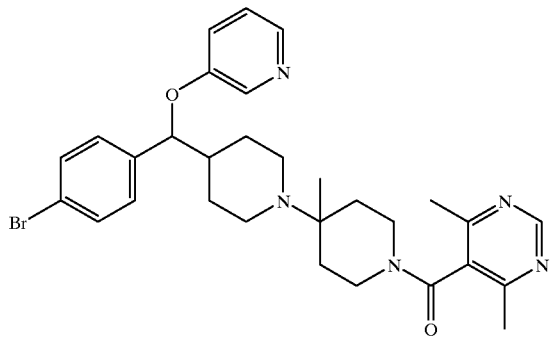

Step 1: To a solution of alcohol 39ab (406 mg; 0.87 mmol), 3-hydroxypyridine (95.1 mg; 1 mmol) and PPh$_3$ (262 mg; 1 mmol) in anhydrous THF (2 ml) at 0° C. was added diethylazodicarboxylate (160 ml; 1 mmol) and the mixture was allowed to warm to RT overnight. The reaction was poured into 5% aqueous NaHCO$_3$, extracted with CH$_2$Cl$_2$, and dried over Na$_2$SO$_4$. After concentration of the solvents, the resulting oil was purified by flash chromatography over silica gel (eluting CH$_2$Cl$_2$/CH$_3$OH 97:3 to 95:5) to afford the desired compound (290 mg; 61%), as an oil.

Step 2: Removal of the Boc-protecting group of the product of step 1 (290 mg; 0.53 mmol) proceeded as in Example 2 to obtain the desired amine (210 mg; 89%), as a white foam.

Step 3: The amine of step 2 (50 mg; 0.11 mmol) was coupled with 4,6-dimethylpyrimidine-5-carboxylic acid following the conditions described in Example 2 to obtain the title compound (32 mg; 49%) as a colorless oil:

$^1$H-NMR (300 MHz, CDCl$_3$) δ 8.91 (s, 1H), 8.20 (br s, 1H), 8.10 (d, J=4.5 Hz, 1H), 7.43 (br d, J=8.4 Hz, 2H), 7.14 (br d, J=8.4 Hz, 2H), 6.95–7.10 (m, 2H), 4.75 (br d, J=6.8 Hz, 1H), 4.15 (m, 1H), 3.44 (m, 1H), 3.33 (m, 1H), 2.95 (m, 2H), 2.79 (m, 1H), 2.42 and 2.44 (s, 3H), 1.85–2.15 (m, 3H), 1.65–1.85 (m, 2H), 1.15–1.50 (m, 5H), 0.90 (s, 3H); HRMS (MH$^+$) 578.2115.

Using similar procedures, compounds of the following structure were prepared

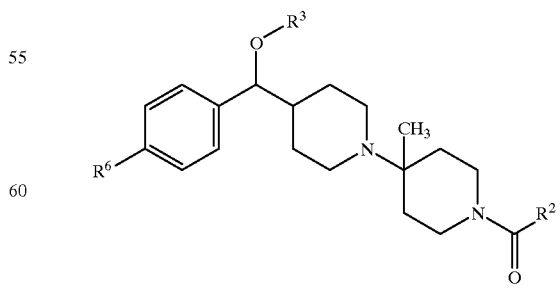

wherein R$^3$, R$^6$ and R$^2$ are as defined in the table:

| Ex. | R⁶ | R³ | R² | HRMS (MH⁺) found |
|---|---|---|---|---|
| 10A | CH₃SO₂— | phenyl | 2,6-dimethyl-4-oxo-phenyl | 592.2848 |
| 10B | Br | pyridin-3-yl | 2,4-dimethylpyridin-3-yl | 577.2166 |
| 10C | Br | 4-fluorophenyl | 4,6-dimethylpyrimidin-5-yl | 595.2078 |
| 10D | F | phenyl | 4,6-dimethylpyrimidin-5-yl | 517.2992 |
| 10E | F | phenyl | 2,4-dimethylpyridin-3-yl | 516.3031 |
| 10F | F | phenyl | 2,6-dimethyl-4-oxo-phenyl | 532.2981 |
| 10G | Br | 3-fluorophenyl | 4,6-dimethylpyrimidin-5-yl | 595.2072 |
| 10H | Cl | 3-chlorophenyl | 4,6-dimethylpyrimidin-5-yl | 567.2308 |
| 10I | F₃C— | phenyl | 2,6-dimethyl-4-oxo-phenyl | 582.2955 |

-continued

| Ex. | R⁶ | R³ | R² | HRMS (MH⁺) found |
|---|---|---|---|---|
| 10J | CH₃SO₂— | phenyl | 4,6-dimethylpyrimidin-5-yl | 577.2853 |
| 10K | CH₃SO₂— | 2-fluorophenyl | 4,6-dimethylpyrimidin-5-yl | 595.2764 |
| 10L | F₃CO— | 3-fluorophenyl | 4,6-dimethylpyrimidin-5-yl | 601.2817 |
| 10M | F₃CO— | 3-chlorophenyl | 4,6-dimethylpyrimidin-5-yl | 617.2514 |
| 10N | CH₃SO₂— | 3-chlorophenyl | 4,6-dimethylpyrimidin-5-yl | 611.2460 |
| 10O | CH₃SO₂— | 3-fluorophenyl | 4,6-dimethylpyrimidin-5-yl | 595.2749 |
| 10P | F₃C— | phenyl | 4,6-dimethylpyrimidin-5-yl | 597.2951 |
| 10Q | F₃CO— | benzyl | 4,6-dimethylpyrimidin-5-yl | 583.2905 |
| 10R | F₃CO— | benzyl | 2,6-dimethylpyran-3-yl | 598.2903 |

-continued

| Ex. | R⁶ | R³ | R² | HRMS (MH⁺) found |
|---|---|---|---|---|
| 10S | F₃C— | 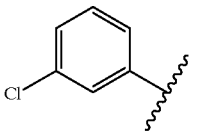 | 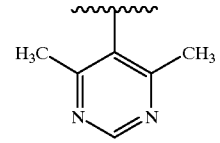 | 601.2556 |
| 10T | F₃C— | 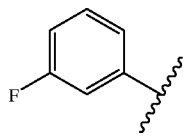 | 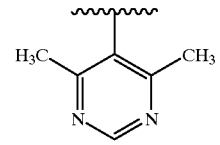 | 585.2559 |
| 10U | F₃CO— | 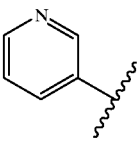 | 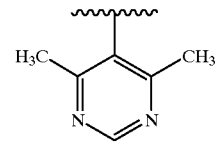 | 584.2860 |

Additional data for compounds of Example 10:

| Ex. | ¹H—NMR (300 MHz ¹H NMR (CDCl₃)) |
|---|---|
| 10C | 8.95 (s, 1H), 7.46 (br d, J=8.4 Hz, 2H), 7.17 (br d, J=8.4 Hz, 2H), 6.86 (t, J=9 Hz, 2H), 6.70–6.72 (m, 2H), 4.69 (br d, J=6.4 Hz, 1H), 4.19 (m, 1H), 3.47 (m, 1H), 3.37 (m, 1H), 2.99 (m, 2H), 2.82 (m, 1H), 2.47 and 2.50 (s, 3H), 1.90–2.15 (m, 3H), 1.65–1.90 (m, 2H), 1.20–1.50 (m, 5H), 0.93 (s, 3H) |
| 10F | 8.17 (d, J=6.8 Hz, 1H), 7.28 (m, 2H), 7.18 (t, J=7.5 Hz, 1H), 6.95–7.10 (m, 3H), 6.87 (t, J=7.5 Hz, 1H), 6.80 (d, J=7.5 Hz, 2H), 4.80 (d, J=6.8 Hz, 1H), 4.17 (m, 1H), 3.25–3.50 (m, 2H), 2.99 (m, 2H), 2.80 (m, 1H), 2.43 (br s, 3H), 2.24 (br s, 3H), 1.65–2.20 (m, 5H), 1.15–1.50 (m, 5H), 0.90 (s, 3H) |
| 10H | 8.95 (s, 1H), 7.32 (br d, J=8.4 Hz, 2H), 7.23 (br d, J=8.4 Hz, 2H), 7.08 (t, J=8.1 Hz, 1H), 6.80–6.90 (m, 2H), 6.68 (m, 1H), 4.77 (br d, J=6.8 Hz, 1H), 4.19 (m, 1H), 3.46 (m, 1H), 3.37 (m, 1H), 3.00 (m, 2H), 2.81 (m, 1H), 2.47 and 2.49 (s, 3H), 1.90–2.15 (m, 3H), 1.65–1.90 (m, 2H), 1.20–1.50 (m, 5H), 0.93 (s, 3H) |
| 10K | 8.81 (s, 1H), 7.78 (d, J=8.4 Hz, 2H), 7.53 (m, 1H), 7.47 (d, J=8.4 Hz, 2H), 6.90 (m, 1H), 6.74 (m, 1H), 6.59 (m, 1H), 4.83 (d, J=6.8 Hz, 1H), 4.08 (m, 1H), 3.20–3.40 (m, 2H), 2.70–3.00 (m, 3H), 2.35 (br s, 3H), 1.65–2.15 (m, 5H), 1.15–1.50 (m, 5H), 0.87 (s, 3H) |
| 10L | 8.33 (d, J=5.1 Hz, 1H), 7.99 (dd, J=4.8 and 1.8 Hz, 1H), 7.86 (d, J=8.4 Hz, 2H), 7.56 (d, J=8.4 Hz, 2H), 7.53 (m, 1H), 6.96 (d, J=6.4 Hz, 1H), 6.75–6.85 (m, 2H), 4.15 (m, 1H), 3.45 (m, 1H), 3.30 (m, 1H), 3.02 (s, 3H), 2.99 (m, 2H), 2.79 (m, 1H), 2.47 and 2.48 (s, 3H), 2.45 (m, 1H), 2.25 and 2.26 (s, 3H), 1.65–2.15 (m, 5H), 1.15–1.55 (m, 5H), 0.90 (s, 3H) |

EXAMPLE 11

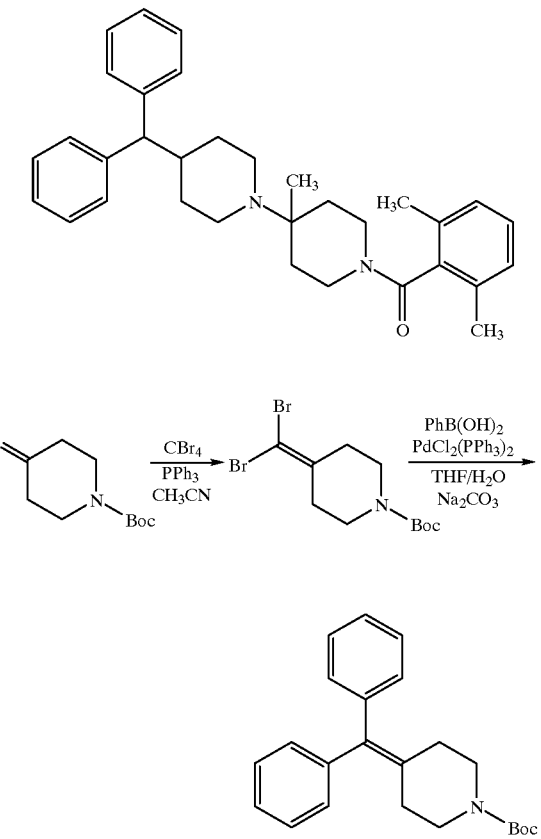

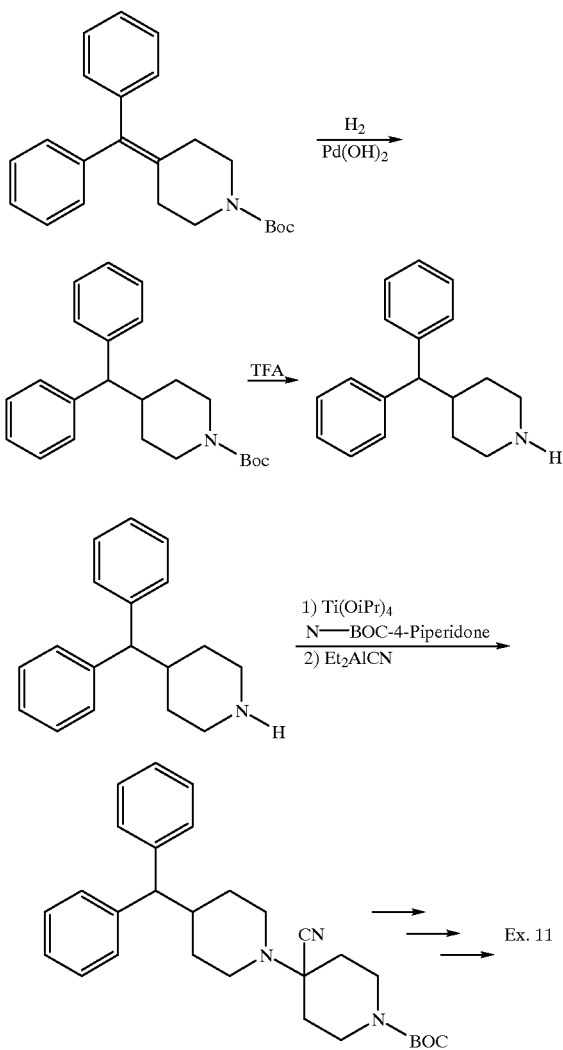

1) N-Boc-4-piperidone (10 g, 50 mmol) and PPh₃ (53 g, 200 mmol) were taken up in CH₃CN (100 ml). The solution was cooled to 0° C. and CBr₄ (33 g, 100 mmol) was added to the solution at 0° C. The solution was stirred at 0° C. for 15 min. and at 25° C. for 2 h. Et₂O (200 ml) was added, and the resulting mixture was filtered through a plug of SiO₂. Concentration gave a yellow solid. Purification via flash chromatography (9/1 hexanes/Et₂O, SiO₂) gave 10 g (56%) of the di-bromo product as a white solid.

2) A solution of the product of step 1 (1 g, 2.8 mmol), PhB(OH)₂ (1.2 g, 9.9 mmol), PdCl₂(PPh₃)₂ (197 mg, 0.28 mmol), and Na₂CO₃ (897 mg, 8.5 mmol) were taken up in THF/H₂O (4/1, 20 ml) and stirred at 65° C. under N₂ for 24 h. The reaction was partitioned between EtOAc and H₂O, the aqueous layer was extracted with EtOAc and the combined organic layers were washed with brine and dried over Na₂SO₄. Filtration and concentration gave a dark brown oil. Purification via flash chromatography (9/1 hexanes/Et₂O, SiO₂) gave 941 mg (96%) of the desired product as a white solid, m.p.=152–153° C.

3) A solution of the product of step 2 (500 mg, 1.4 mmol) and Pd(OH)₂ on carbon (100 mg, 20 wt % Pd (dry basis), 50 wt % H₂O) were taken up in CH₃OH (20 ml) and shaken in a Parr apparatus under H₂ (50 psi) for 15 h. The mixture was filtered and concentrated to give 501 mg (99%) of the diphenylmethyl piperidine as a colorless oil.

4) TFA (1.4 ml) was added to a solution of the product of step 3 (500 mg, 1.4 mmol) in CH₂Cl₂ (15 ml). The solution was stirred at 25° C. for 23 h. The solution was concentrated and the residue partitioned between CH₂Cl₂ and 1 N NaOH. The aqueous layer was extracted with CH₂Cl₂, the combined organic layers were dried over Na₂SO₄, filtered and concentrated to obtain 349 mg (99%) of the free amine as a yellow oil, m.p. (HCl)= decomp. above 220–230° C. HRMS calc'd for C₁₈H₂₂N (MH⁺): 252.1752, Found: 252.1751.

5) A solution of the product of step 4 (349 mg, 1.4 mmol), N-Boc-4-piperidone 280 mg, 1.4 mmol), and Ti(OiPr)₄ (0.42 ml, 1.4 mmol) were taken up CH₂Cl₂ (15 ml) under N₂. After stirring at 25° C. for 17 h, Et₂AlCN (2.8 mmol, 2.8 ml of 1.0 M in toluene) was added and the solution was stirred an additional 18 h at 25° C. The solution was quenched with sat. NaHCO₃, diluted with EtOAc and filtered through Celite. The aqueous layer was extracted with EtOAc and the combined EtOAc layers were dried over Na₂SO₄. Filtration and concentration gave a yellow oil. Purification via preparative layer chromatography (3/1 hexanes/EtOAc, SiO₂) gave 430 mg (67%) of the desired product as an oil.

6) A solution of the product of step 5 (430 mg, 0.94 mmol) in THF (20 ml) was cooled to 0° C. under N₂. CH₃MgBr (1.6 ml of 3.0 M in Et₂O, 4.7 mmol) was added at 0° C. and the solution stirred at 25° C. for 19 h. The reaction mixture was quenched with sat. NH₄Cl, diluted with CH₂Cl₂ and 1 N NaOH (check aqueous layer with pH paper, pH=8–10). The layers were separated and the aqueous layer extracted with CH₂Cl₂. The combined organic layers were dried over Na₂SO₄, filtered and concentrated to obtain a yellow oil. Purification via flash chromatography (3/1 hexanes/EtOAc, SiO₂) gave 275 mg (65%) of the product as a yellow oil.

7) TFA (0.60 ml) was added to a solution of the product of step 6 (275 mg, 0.61 mmol) in CH₂Cl₂ (15 ml) and the solution was stirred at 25° C. for 18 h. The solution was concentrated and the residue was partitioned between CH₂Cl₂ and 1 N NaOH. The aqueous layer was extracted with CH₂Cl₂, the combined organic layers were dried over Na₂SO₄, filtered and concentrated to obtain 209 mg (99%) of thje amine as a yellow oil. HRMS calc'd for C₂₄H₃₃N₂ (MH⁺): 349.2644, Found: 349.2638.

8) A solution of the product of step 7 (50 mg, 0.14 mmol), 2.6-dimethylbenzoic acid (63 mg, 0.42 mmol), EDCl (54 mg, 0.28 mmol), HOBT (38 mg, 0.28 mmol), and iPr₂NEt (0.10 ml) were taken up in CH₂Cl₂ (3 ml). The solution was stirred at 25° C. for 18 h, then diluted with CH₂Cl₂ and washed with 1 N NaOH. The aqueous layer was extracted with CH₂Cl₂, the combined organic layers were dried over Na₂SO₄, and filtered and concentrated to give a yellow oil. Purification via preparative thin-layer chromatography (3/1 hexanes/EtOAc SiO₂) gave 47 mg (70%) of the title compound as a colorless oil, m.p. (HCl salt)=195–201° C. HRMS calc'd for C₃₃H₄₁N₂O (MH⁺): 481.3219, Found: 481.3225.

Using similar procedures, compounds of the following structure were prepared
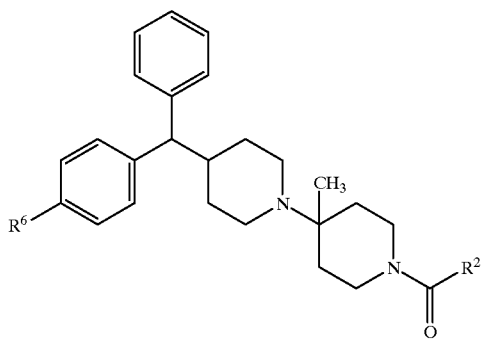
wherein $R^6$ and $R^2$ are as defined in the table:
| Ex. | $R^6$ | $R^2$ | HRMS (MH$^+$) found | M.p., °C. (HCl salt) |
|---|---|---|---|---|
| 11A | H | 2,4-dimethylpyridin-3-yl | 482.3156 | 201–207 |
| 11B | F$_3$CO— | 2,4-dimethylpyridin-3-yl | 565.3069 | 204–209 |
| 11C | H | 3-methyl-2-aminophenyl | 482.3168 | 187–192 |
| 11D | F$_3$CO— | 4,6-dimethylpyrimidin-5-yl | 567.2957 | 175–181 |
| 11E | F$_3$CO— | 2,4-dimethyl-aryloxy | 582.2966 | 92–98 |
| 11F | F$_3$CO— | 2,4-dimethylpyridin-3-yl | 566.3020 | 175–181 |
EXAMPLE 12
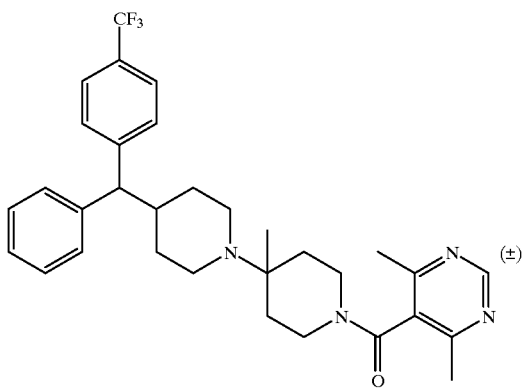
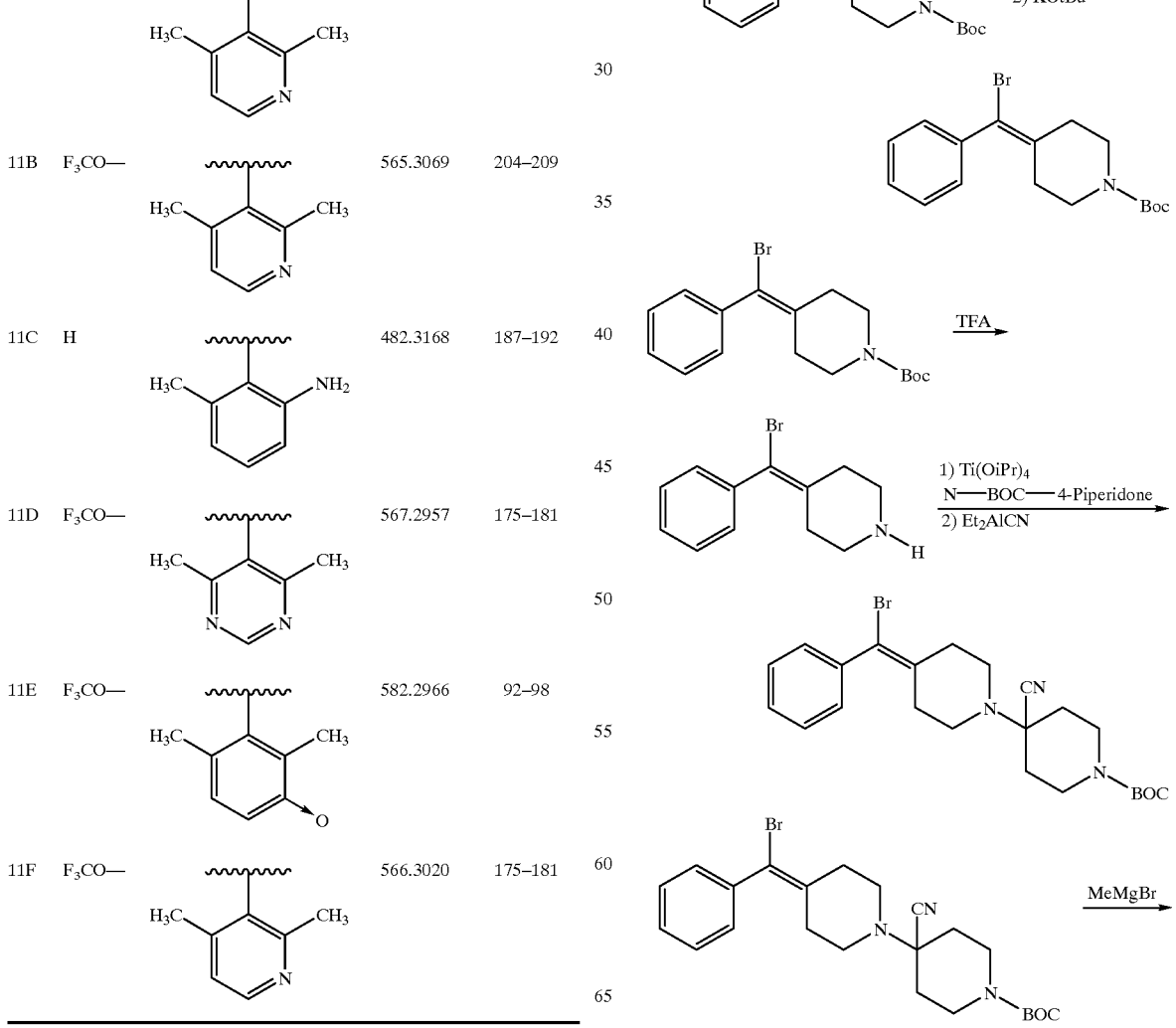

-continued

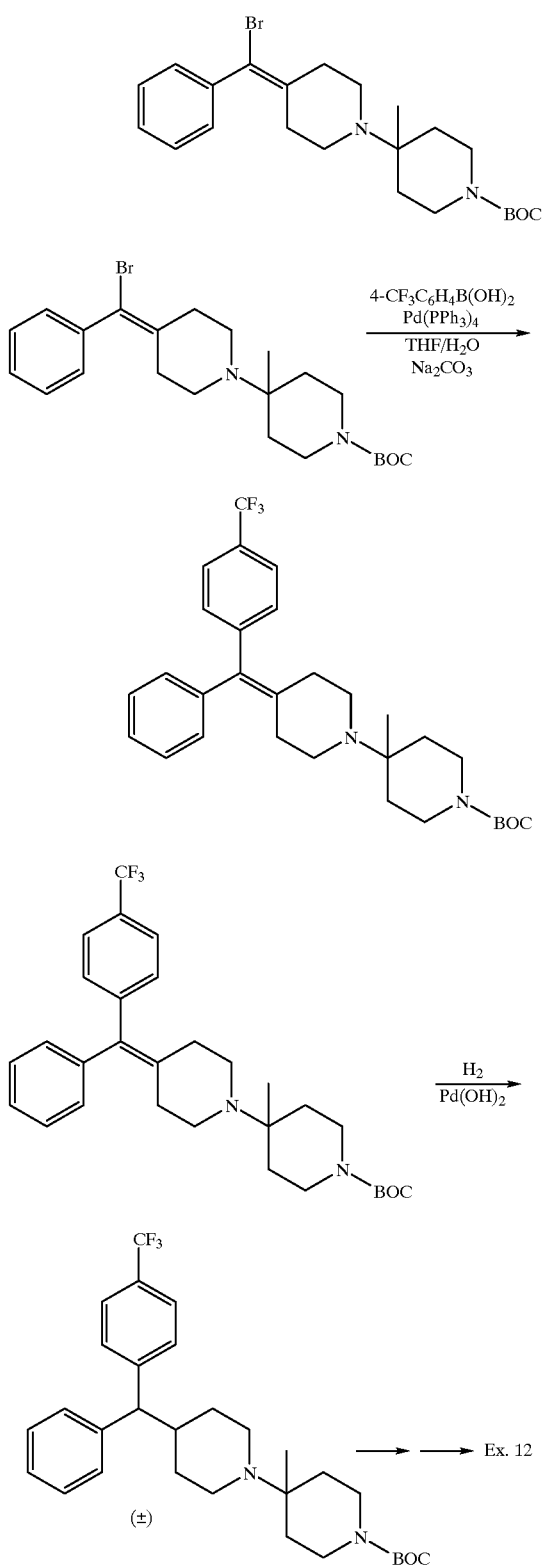

1) N-Boc-4-piperidone (10 g, 50 mmol) and diethyl benzyi-phosponate (12.6g, 55 mmol) were taken up in dry THF (50 ml) under $N_2$. NaH (2.4 g, 60 mmol, 60 wt % in oil dispersion) was added to the solution at 25° C. The resulting mixture was heated at reflux for 3.5 h. The solution was partitioned between EtOAc and saturated $NH_4Cl$, the aqueous layer was extracted with EtOAc and the combined EtOAc layers were washed with brine and dried over $MgSO_4$. Filtration and concentration afforded a yellow oil. Purification via flash chromatography (10/1 hexanes/$Et_2O$, $SiO_2$) gave 9.85 g (72%) of the desired compound as a solid, m.p.=63–65° C.

2) Bromine (1 ml, 20 mmol; dissolved in 10 ml $CH_2Cl_2$) was added dropwise to a $CH_2Cl_2$ (100 ml) solution of the product of step 1 (5.0 g, 18 mmol) at 0° C. The solution was stirred at 0° C. for 15 min, then concentrated under reduced pressure. The crude product was taken up in tert-butanol/THF (4/1, 100 ml), and KOtBu (4.1 g, 36 mmol) was added to the solution in portions. The yellow mixture was stirred at 25° C. for 5 h, then concentrated under reduced pressure. The residue was partitioned between EtOAc and saturated $NH_4Cl$, the aqueous layer was extracted with EtOAc, and the combined EtOAc layers were washed with brine and dried over $MgSO_4$. Filtration and concentration gave a yellow solid. Purification via flash chromatography (7/1 hexanes/$Et_2O$, $SiO_2$) gave 5.2 g (81%) of the desired product as a yellow solid. m.p.=80–83° C.

3) TFA (5.9 ml) was added to a solution of the product of step 2 (2.1 g, 5.9 mmol) in $CH_2Cl_2$ (25 ml). The solution was stirred at 25° C. for 5 h, concentrated and the residue was partitioned between $CH_2Cl_2$ and 1 N NaOH. The aqueous layer was extracted with $CH_2Cl_2$ and the combined organic layers were dried over $Na_2SO_4$, filtered and concentrated to obtain 1.46 g (98%) of the amine as an orange oil, m.p. (HCl salt)=decomp. above 185–195° C. HRMS calc'd for $C_{12}H_{15}BrN$ ($MH^+$): 254.0367, Found: 254.0374.

4) A solution of the product of step 3 (1.4 g, 5.6 mmol), N-Boc-4-piperidone (1.1 g, 5.6 mmol), and $Ti(OiPr)_4$ (1.7 ml, 5.6 mmol) were taken up in $CH_2Cl_2$ (30 ml) under $N_2$. After stirring at 25° C. for 18 h, $Et_2ALCN$ (6.7 mmol, 6.7 ml, 1.0 M in toluene) was added to the solution and the solution was stirred an additional 18 h at 25° C. The solution was quenched with sat. $NaHCO_3$, diluted with EtOAc and filtered through Celite. The aqueous layer was extracted with EtOAc and the combined EtOAc layers were dried over $Na_2SO_4$. Filtration and concentration gave a yellow oil. Purification via flash chromatography (3/1 hexanes/EtOAc, $SiO_2$) gave 2.0 g (78%) of the desired product as an off-white solid.

5) A solution of the product of step 4 (2.0 g, 4.3 mmol) in THF (30 ml) was cooled to 0° C. under N2. $CH_3MgBr$ (7.2 ml of 3.0 M in $Et_2O$, 21 mmol) was added to the solution at 0° C. The solution was warmed to 25° C. and stirred at that temperature for 16 h. The reaction mixture was quenched with sat. $NH_4Cl$ and diluted with $CH_2Cl_2$ and 1 N NaOH (check aqueous layer with pH paper, pH=8–10). The layers were separated, the aqueous layer was extracted with $CH_2Cl_2$ and the combined organic layers were dried over $Na_2SO_4$. Filtration and concentration gave a yellow oil. Purification via flash chromatography (3/1 hexanes/EtOAc, $SiO_2$) gave 1.56 g (82%) of the desired product as a yellow oil.

6) A solution of the product of step 5 (300 mg, 0.67 mmol), 4-$CF_3C_6H_4B(OH)_2$ (380 mg, 2 mmol), $PdCl_2(PPh_3)_2$ (50 mg, 0.067 mmol), and $Na_2CO_3$ (210 mg, 2 mmol) were taken up THF/$H_2O$ (4/1, 15 ml) and stirred at 65° C. under $N_2$ for 18 h. The solution was partitioned between EtOAc and $H_2O$ and the aqueous layer was extracted with EtOAc. The combined organic layers were washed with brine and dried over $Na_2SO_4$. Filtration and concentration gave a dark brown oil. Purification via flash chromatography (4/1 hexanes/EtOAc, SiO$_2$) gave 229 mg (67%) of the desired product as a colorless oil.

7) A solution of the product of step 6 (229 mg, 0.45 mmol) and Pd(OH)$_2$ on carbon (200 mg, 20 wt % Pd (dry basis), 50 wt % H$_2$O) were taken up in CH$_3$OH (35 ml) and shaken in a Parr apparatus under H$_2$ (50 psi) for 20 h. The mixture was filtered and concentrated to obtain 232 mg (100%) of the (±)-product as a colorless foam. HRMS calc'd for C$_{30}$H$_{40}$O$_2$N$_3$ (MH$^+$): 517.3042, Found: 517.3050.

8) TFA (0.45 ml) was added to a solution of the product of step 7 (235 mg, 0.45 mmol) in CH$_2$Cl$_2$ (15 ml). The solution was stirred at 25° C. for 24 h, then concentrated and the residue was partitioned between CH$_2$Cl$_2$ and 1 N NaOH. The aqueous layer was extracted with CH$_2$Cl$_2$, the combined organic layers were dried over Na$_2$SO$_4$, filtered and concentrated to obtain 146 mg (78%) of the (±)-amine as a yellow oil.

9) A solution of the product of step 8 (102 mg, 0.25 mmol), 4,6-.S dimethylpyrimidine-5-carboxylic acid (110 mg, 0.75 mmol), EDCl (96 mg, 0.50 mmol), HOBT (70 mg, 0.50 mmol), and iPr$_2$NEt (0.17 ml) was taken up in CH$_2$Cl$_2$ (3 ml). The solution was stirred at 25° C. for 18 h, then diluted with CH$_2$Cl$_2$ and washed with 1 N NaOH. The aqueous layer was extracted with CH$_2$Cl$_2$, the combined organic layers were dried over Na$_2$SO$_4$, filtered and concentrated to obtain a yellow oil. Purification via preparative thin-layer chromatography (1/1 acetone/hexanes SiO$_2$) gave 121 mg (88%) of the title compound as a colorless oil, m.p. (HCl salt)=186–191° C. HRMS calc'd for C$_{32}$H$_{38}$N$_4$OF$_3$ (MH$^+$): 551.2998, Found: 551.3012.

The 4,6-dimethylpyrimidine-5-carboxylic acid used in step 9 was made by the following process:

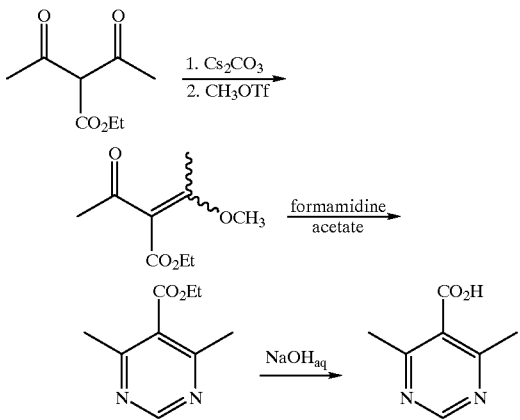

Step 1: Ethyl diacetoacetate (93.4 g), Cs$_2$CO$_3$ (185 g) and CH$_3$CN (550 ml) were mixed together, using an overhead mechanical stirrer. CH$_3$CN (50 ml) was added and the resulting mixture was cooled to 0° C. Methyl trifluoromethane sulfonate (88.6 g) was added dropwise and after addition, the cooling bath was removed. The mixture was stirred for 1 h at RT, filtered, and the salts were washed with Et$_2$O (2×50 ml). The organic extracts were combined and Et$_2$O (300 ml) was added. The resulting mixture was filtered, the filter cake was washed with Et$_2$O (2×100 ml), the Et$_2$O extracts were combined and evaporated to half volume. The solution was cooled in an ice bath and washed once with cooled (0° C.) 2 N NaOH (pH=11). The Et$_2$O layer was dried over MgSO$_4$, filtered and evaporated to give the desired product as a yellow liquid (64.7 9) in 65% yield, which was used directly in the next step.

Step 2: The product of step 1 (64.2 g), sodium ethoxide in ethanol (commercial solution; 21 wt %; 113 g) and formamidine acetate (36.2 g) were mixed together at RT. After refluxing for 4 h, the mixture was cooled to RT, the resulting precipitate was filtered off and the ethanol was removed under vacuum. The resulting liquid was partitioned between water and CH$_2$Cl$_2$ and the aqueous layer was extracted with CH$_2$Cl$_2$ (3×150 ml). The CH$_2$Cl$_2$ extracts were dried over MgSO$_4$, filtered and evaporated to give a dark crude liquid (50.7 g) which was purified by silica gel chromatography (980 g; 4:1 hexanes:EtOAc as eluant). After evaporation of the appropriate fractions, the desired product (28.5 g) was isolated in 46% yield and used directly in the next step.

Step 3: The product of step 2 (28.1 g), NaOH (6.72 g), water (65 ml) and EtOH (130 ml) were mixed together at RT and heated at reflux for 1 h. The resulting solution was cooled to RT and the volatile materials were removed in vacuo until a thick paste resulted. Water (20 ml) was added, the mixture was cooled to 0° C. and conc. HCl (14.3 ml) was added dropwise with stirring. The resulting white precipitate was collected by filtration, washed with ice water (2×10 ml) and air dried with suction for 30 min. The resulting white solid was treated with toluene (2×20 ml), the solvent was removed in vacuo at 50° C. and then dried under vacuum (1 mm Hg) for 18 h. The desired product (14.9 g) was isolated as a white solid in 63% yield, mp: 176–178° C. Elemental analysis of C$_7$H$_8$N$_2$O$_2$: calc'd C 55.26%, H 5.30%, N 18.41%; found: C 55.13%, H 5.44%, N 18.18%.

A second crop of product was isolated by evaporation of the aqueous filtrate (from above) to dryness and addition of water (20 ml). The resulting mixture was stirred at RT for 5 min, cooled in an ice bath and the precipitate formed was collected by filtration. The resulting solid was washed with ice water (2×5 ml) and dried as described above to give the product (4.68 g) as a cream colored solid to give a combined yield of 83%.

EXAMPLE 13

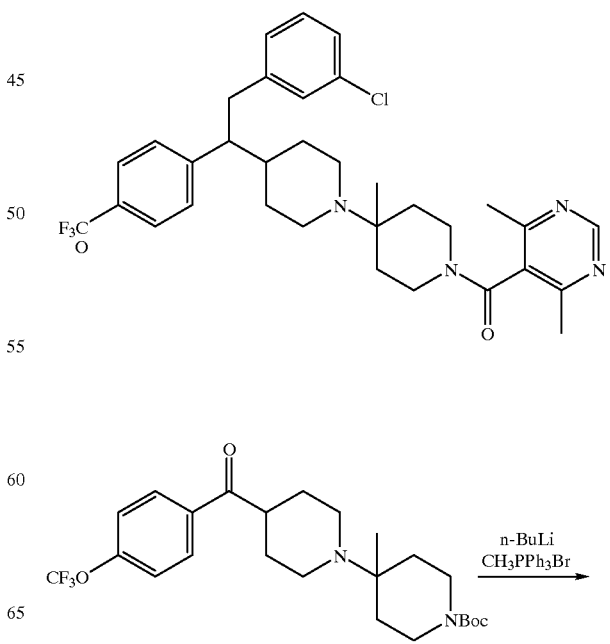

-continued

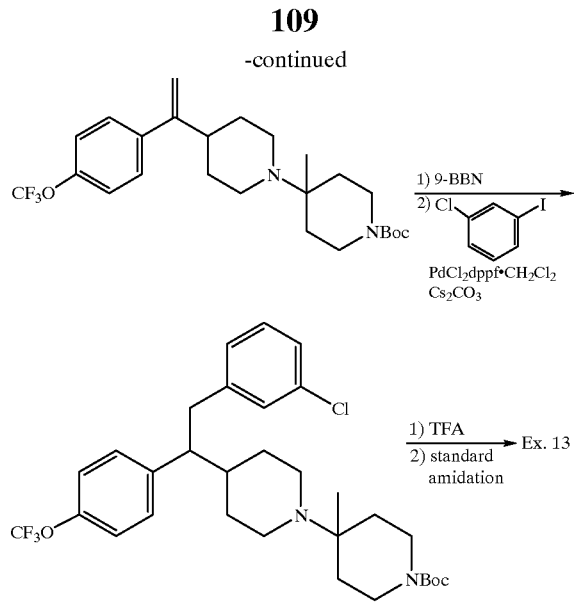

Step 1: To a suspension of methyltriphenylphosphonium bromide (1.89 g; 4.80 mmol) in anhydrous THF (15 ml) at −40° C. is added n-BuLi 2.5 N in hexanes (2.12 ml; 5.3 mmol) via syringe. The reaction is allowed to warm to 0° C., stirred 30 min at this temperature, and a solution of the product of Example 6, step B-2 (2.24 g; 4.8 mmol) is added. The solution is then allowed to warm to RT overnight, poured into $CH_2Cl_2$, and washed with saturated $NaHCO_3$ then brine. The residue obtained after concentration of the organic layer is purified by flash chromatography over silica gel (eluting with $CH_2Cl_2$/EtOAc, 9:1) to afford 0.56 g (25%) of an oil.

Step 2: A solution of the product of step 1 (0.56 g; 1.2 mmol) and 9-BBN 0.5 N in THF (3 ml; 1.5 mmol) is refluxed 2 h under inert atmosphere. Part of this solution (1.5 ml; 0.59 mmol of theoretical intermediate) is added to a mixture of 1-chloro-3-iodobenzene (88 μl; 0.71 mmol), $PdCl_2dppf \cdot CH_2Cl_2$ (19.8 mg), triphenylarsine (24.1 mg) and $Cs_2CO_3$ (250 mg) in DMF (0.40 ml) and water (80 μl). The reaction is stirred 2 h at 60° C. and overnight at RT, poured into 5% aqueous $NaHCO_3$, and extracted with $CH_2Cl_2$. Combined organic layers are dried over $Na_2SO_4$, concentrated, and purified by chromatography over silica gel (eluting with EtOAc/hexanes, 8:2) to provide 100 mg (29%) of an oil.

Step 3: The Boc-protecting group of the product of step 2 (100 mg; 0.17 mmol) was removed as in Example 2 to obtain the desired amine (70 mg; 86%). This amine (45 mg; 0.09 mmol) was coupled with 4,6-dimethylpyrimidine-5-carboxylic acid following the conditions described in Example 2 to obtain the title compound as a colorless oil(32 mg). $^1$H-NMR (300 MHz, $CDCl_3$) δ 8.93 (d, J=3.8 Hz, 1H), 6.90–7.10 (m, 5H), 6.88 (br s, 1H), 6.71 (d, J=7 Hz, 1H), 4.20 (m, 1H), 3.25–3.55 (m, 2H), 3.19 (m, 2H), 2.50–3.10 (m, 5H), 2.47 and 2.48 (s, 3H), 2.42 and 2.43 (s, 3H), 1.70–2.20 (m, 5H), 1.20–1.65 (m, 5H), 0.92 (s, 3H); HRMS (MH+) 615.2722.

Using a similar procedure, the following compound was also prepared:

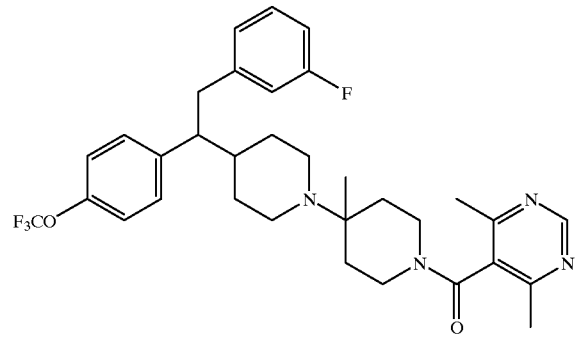

13A HRMS (MH+) 599.3015

EXAMPLE 14

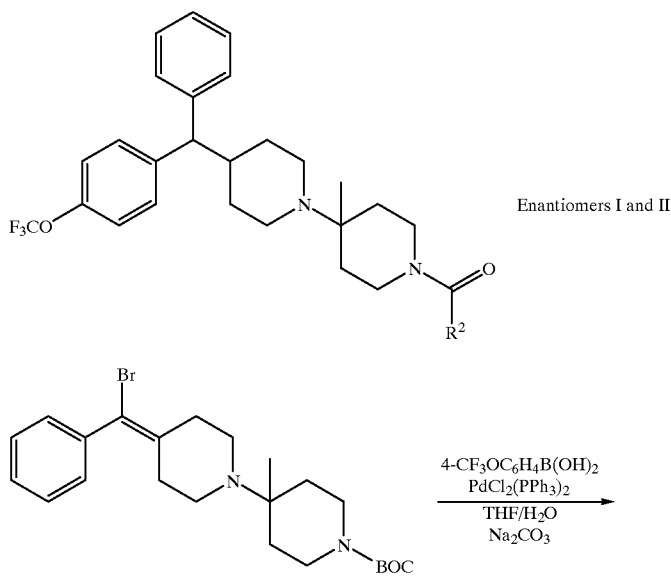

Enantiomers I and II

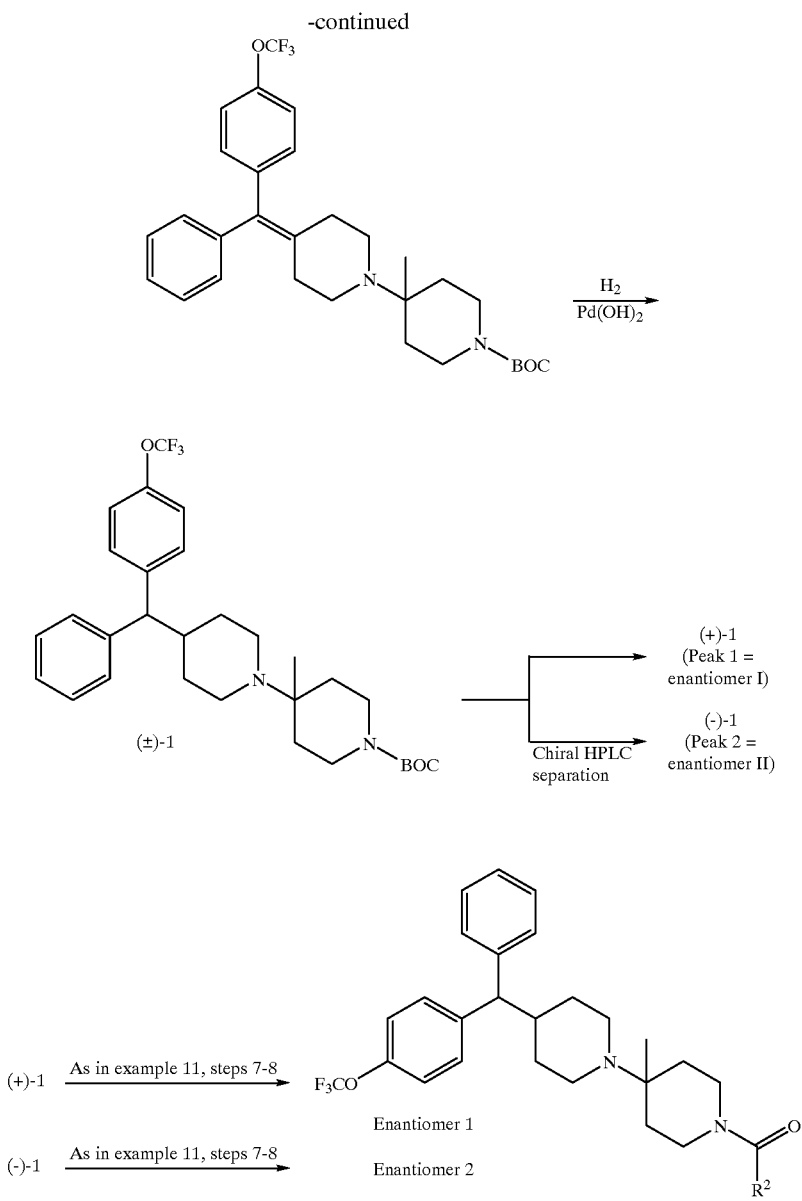

To prepare a compound wherein $R^2$ is 2,6-dimethylphenyl:

1) A solution of the product of step 5 in example 12 (300 mg, 0.67 mmol), 4-$CF_3OC_6H_4B(OH)_2$ (410 mg, 2 mmol), $PdCl_2(PPh_3)_2$ (50 mg, 0.067 mmol), and $Na_2CO_3$ (210 mg, 2 mmol) were taken up in THF/$H_2O$ (4/1, 15 ml) and stirred at 65° C. under $N_2$ for 19 h. The solution was partitioned between EtOAc and $H_2O$, and the aqueous layer was extracted with EtOAc. The combined organic layers were washed with brine and dried over $Na_2SO_4$. Filtration and concentration gave a dark brown oil. Purification via flash chromatography (4/1 hexanes/$Et_2O$, $SiO_2$) gave 356 mg (100%) of the desired product as a yellow oil.

2) A solution of the product in step 1 (340 mg, 0.64 mmol) and $Pd(OH)_2$ on carbon (300 mg, 20 wt % Pd (dry basis), 50 wt % $H_2O$) were taken up in $CH_3OH$ (35 ml) and shaken in a Parr apparatus under $H_2$ (50 psi) for 18 h. The mixture was filtered and concentrated to obtain 341 mg (100%) of the product, (±)-1, as a colorless foam.

3) The amine (±)-1 was resolved via chiral HPLC separation. The conditions are as follows: CHIRALCEL® OD™ (5 cm×30 cm); Hexane/isopropyl alcohol/diethylamine 75/25/0.05) at 25° C.; 254 nm detection. The retention times for peak 1, (+)-enantiomer, and peak 2, (−)-enantiomer were 3.8 and 4.9 minutes, respectively [CHIRALCEL® OD™ (hexane/ethanol/diethylamine 90/10/0.1) 25° C. at 254 nm]. Peak 1 and peak 2 are the first and second eluting peaks from the column, respectively. The enantiomers (I and II) were deprotected ($CH_2Cl_2$/TFA), and the free amine was coupled to the 2,6-dimethylbenzoic acid using the conditions described in example 11, steps 7 and 8. The hydrochloride salts were obtained by taking the free base up in EtOAc and triturating with 1 M HCl in $Et_2O$.

Data for the above compounds, 14A and 14B, and for additional compounds made in a similar manner, are given in the following table. In each case, the enantiomer designator I is derived from (+)-1 and the enantiomer designated II is derived from (−)-1.

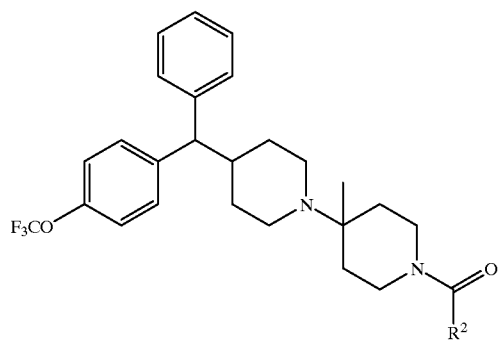
| Ex. | Ar | Enantiomer | m.p. (HCl) | HRMS calc | HRMS found |
|---|---|---|---|---|---|
| 14A | 2,6-dimethylphenyl | I | 185–190 | 565.3042 | 565.3050 |
| 14B | 2,6-dimethylphenyl | II | 175–180 | 565.3042 | 565.3050 |
| 14C | 4,6-dimethylpyrimidinyl | I | 168–174 | 567.2947 | 567.2951 |
| 14D | 4,6-dimethylpyrimidinyl | II | 170–175 | 567.2947 | 567.2957 |
| 14E | 2,4-dimethylpyridinyl N-oxide | I | 195–201 | 582.2944 | 582.2944 |
| 14F | 2,4-dimethylpyridinyl N-oxide | II | 180–185 | 582.2944 | 582.2958 |
| 14G | 3,5-dimethyl-4-hydroxyphenyl | II | 214–218 | 581.2991 | 581.2984 |

-continued
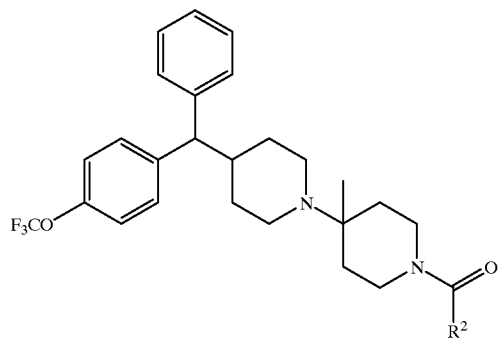
| Ex. | Ar | Enantiomer | m.p. (HCl) | HRMS calc | found |
|---|---|---|---|---|---|
| 14H | 3,4,5-trimethylphenyl-pyridine N-oxide | II | 145–151 | 658.3257 | 658.3251 |
| 14I | 3,4,5-trimethylphenyl-CHF₂ | II | 193–198 | 615.3010 | 615.3016 |
| 14J | 3,4,5-trimethylphenyl-NH-C(O)-NHEt | II | 195–200 | 651.3522 | 651.3526 |
EXAMPLE 15
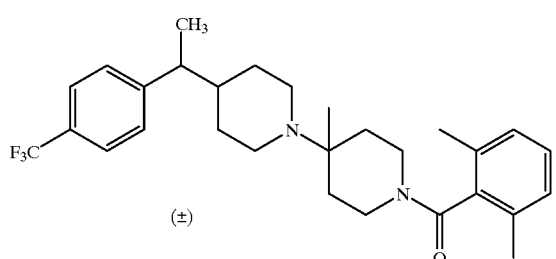
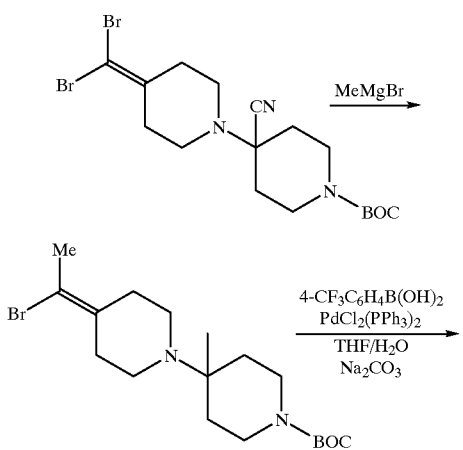

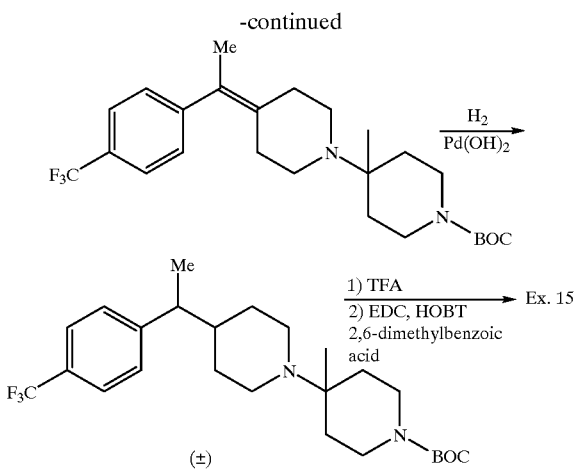

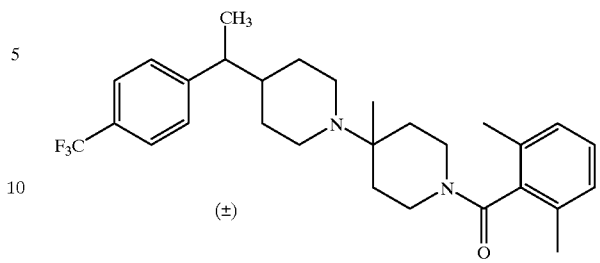

(±)

1) The dibromo-olefin (3.55 g, 10 mmol) and TFA (10 ml) were taken up in $CH_2C_{12}$ and stirred at 25° C. for 20 h. The solution was concentrated. The residue was partitioned between $CH_2Cl_2$ and 1 N NaOH. The aqueous layer was extracted with $CH_2Cl_2$. The combined organic layers were dried ($Na_2SO_4$). Filtration and concentration gave the 2.4 g (94%) of the free piperdine as a colorless oil. The free piperdine (2.41 g, 9.45 mmol) was treated sequentially with (a) N-Boc-4-piperidone/Ti(OiPr)$_4$, and (b) $Et_2AlCN$, to give the cyano-amine as described in Step 5 of Example 11.

2) The product of Step 1 and MeMgBr (16 ml, 3.0 M in $Et_2O$) were taken up in THF (30 ml) and stirred at 25° C. for 19 h. The solution was quenched with 1 N NaOH and EtOAc. The mixture was filtered (Celite). The aqueous layer was extracted with EtOAc, the combined EtOAc layers were washed with brine and dried ($Na_2SO_4$). Filtration and concentration gave a yellow oil. Purification via flash chromatography (6/1 hexanes/EtOAc, $SiO_2$) gave 2.54 g (69% from the free piperidine) of the vinyl bromide as a solid. m.p. (free base) 85–90° C. HRMS (MH+) calcd. for $C_{18}H_{32}O_2N_2Br$, 387.1647; Found, 387.1638.

3) The product of Step 2 (200 mg, 0.52 mmol), 4-$CF_3C_6H_4B$(OH)$_2$ (344 mg, 1.8 mmol), PdCl$_2$(PPh$_3$)$_2$ (36 mg, 0.052 mmol), and $Na_2CO_3$ (165 mg, 1.56 mmol) were taken up in THF/$H_2O$ (4/1, 10 ml) and heated at 75° C. (oil bath) for 21 hours. The solution was partitioned between EtOAc and $H_2O$. The aqueous layer was extracted with EtOAc, the combined EtOAc layers were washed with brine and dried ($Na_2SO_4$). Filtration and concentration gave a yellow oil. Purification via flash chromatography (3/1 to 1/1 hexanes/EtOAc, $SiO_2$) gave 210 mg (89%) of the phenyl substitued olefin as an oil. HRMS (MH$^+$) calcd. for $C_{25}H_{36}O_2N_2F_3$, 453.2729; Found, 453.2728.

4) The product of Step 3 was hydrogenated as described in Step 3 of Example 11. The reduced product was deprotected and coupled to 2,6-dimethyl benzoic acid as described in Example 11, steps 7–8 to give the title compound as a yellow oil (37 mg, 55%). m.p. (HCl salt) 130–140° C. HRMS (MH$^+$) calcd. for $C_{29}H_{38}ON_2F_3$, 487.2936; Found, 487.2928.

Using a similar procedure, the following compound was prepared:

m.p. (HCl salt) 135–145° C. HRMS (MH$^+$) calcd. for $C_{29}H_{38}O_2N_2F_3$, 503.2885; Found, 503.2896.

The following assays can be used to determine the CCR5 inhibitory and antagonistic activity of the compounds of the invention.

CCR5 Membrane Binding Assay:

A high throughput screen utilizing a CCR5 membrane binding assay identifies inhibitors of RANTES binding. This assay utilizes membranes prepared from NIH 3T3 cells expressing the human CCR5 chemokine receptor which have the ability to bind to RANTES, a natural ligand for the receptor. Using a 96-well plate format, membrane preparations are incubated with $^{125}$I-RANTES in the presence or absence of compound for one hour. Compounds are serially diluted over a wide range of 0.001 ug/ml to 1 ug/ml and tested in triplicates. Reaction cocktails are harvested through glass fiber filters, and washed thoroughly. Total counts for replicates are averaged and data reported as the concentration required to inhibit 50 percent of total $^{125}$I-RANTES binding. Compounds with potent activity in the membrane binding assay are further characterized in seconday cell-based HIV-1 entry and replication assays.

HIV-1 Entry Assay:

Replication defective HIV-1 reporter virions are generated by cotransfection of a plasmid encoding the NL4-3 strain of HIV-1 (which has been modified by mutation of the envelope gene and introduction of a luciferase reporter plasmid) along with a plasmid encoding one of several HIV-1 envelope genes as described by Connor et al, *Virology*, 206 (1995), p. 935–944. Following transfection of the two plasmids by calcium phosphate precipitation, the viral supernatants are harvested on day 3 and a functional viral titer determined. These stocks are then used to infect U87 cells stably expressing CD4 and the chemokine receptor CCR5 which have been preincubated with or without test compound. Infections are carried out for 2 hours at 37° C., the cells washed and media replaced with fresh media containing compound. The cells are incubated for 3 days, lysed and luciferase activity determined. Results are reported as the concentration of compound required to inhibit 50% of the luciferase activity in the control cultures.

HIV-1 Replication Assay:

This assay uses primary peripheral blood mononuclear cells or the stable U87-CCR5 cell line to determine the effect of anti-CCR5 compounds to block infection of primary HIV-1 strains. The primary lymphocytes are purified from normal healthy donors and stimulated in vitro with PHA and IL-2 three days prior to infection. Using a 96-well plate format, cells are pretreated with drug for 1 hour at 37° C. and subsequently infected with an M-tropic HIV-1 isolates. Following infection, the cells are washed to remove residual inoculum and cultured in the presence of compound for 4 days. Culture supernatants are harvested and viral replication measured by determination of viral p24 antigen concentration.

Calcium Flux Assay:

Cells expressing the HIV coreceptor CCR5 are loaded with calcium sensitive dyes prior to addition of compound or the natural CCR5 ligand. Compounds with agonist properties will induce a calcium flux signal in the cell, while CCR5 antagonists are identified as compounds which do not induce signaling by themselves but are capable of blocking signaling by the natural ligand RANTES.

GTPγS Binding Assay (secondary membrane binding assay):

A GTPγS binding assay measures receptor activation by CCR5 ligands. This assay measures the binding of $^{35}$S labeled-GTP to receptor coupled G-proteins that occurs as a result of receptor activation by an appropriate ligand. In this assay, the CCR5 ligand, RANTES, is incubated with membranes from CCR5 expressing cells and binding to the receptor activation (or binding) is determined by assaying for bound $^{35}$S label. The assay quantitatively determines if compounds exhibit agonist characteristics by inducing activation of the receptor or alternatively antagonist properties by measuring inhibition of RANTES binding in a competitive or non-competitive fashion.

Chemotaxis Assay:

The chemotaxis assay is a functional assay which characterizes the agonist vs. antagonist properties of the test compounds. The assay measures the ability of a non-adherent murine cell line expressing human CCR5 (BaF-550) to migrate across a membrane in response to either test compounds or natural ligands (i.e., RANTES, MIP-1β). Cells migrate across the permeable membrane towards compounds with agonist activity. Compounds that are antagonists not only fail to induce chemotaxis, but are also capable of inhibiting cell migration in response to known CCR5 ligands.

The role of CC chemokine receptors such as CCR-5 receptors in inflammatory conditions has been reported in such publications as *Immunology Letters*, 57, (1997), 117–120 (arthritis); *Clinical & Experimental Rheumatology*, 17 (4) (1999), pp. 419–425 (rheumatoid arthritis); *Clinical & Experimental Immunology*, 117 (2) (1999), pp.237–243 (atopic dermatitis); *International Journal of Immunopharmacology*, 20 (11) (1998), pp. 661–7 (psoriasis); *Journal of Allergy & Clinical Immunology*, 100 (6, Pt 2) (1997), pp. S52–5 (asthma); and *Journal of Immunology*, 159 (6) (1997), pp. 2962–72 (allergies).

In the assay to determine inhibition of RANTES binding, compounds of the invention range in activity from a Ki of 0.1 to 2000 nM, with preferred compounds having a range of activity from 0.1 to 1000 nM, more preferably 0.1 to 500 nM, and most preferably 0.1 to 100 nM. The results for preferred and representative compounds of formulas I and II in the test to determine inhibition of RANTES binding are given in the table below. In the table, "Ex. No." stands for "Example Number" and "nM" stands for "nanomolar."

| Ex. No. | Ki (nM) Inhibition of RANTES binding |
|---|---|
| 1B | 14 |
| 1J | 1 |
| 2 | 9.6 |
| 2G | 1.8 |
| 2S | 17.9 |
| 2JJ | 0.58 |
| 4B | 0.5 |

-continued

| Ex. No. | Ki (nM) Inhibition of RANTES binding |
|---|---|
| 4C | 0.5 |
| 5L | 7.9 |
| 5N | 1.7 |
| 5O | 0.4 |
| 5Z | 0.3 |
| 5AB | 0.1 |
| 6V | 0.8 |
| 7U | 62.5 |
| 9D | 588 |

For preparing pharmaceutical compositions from the CCR5 antagonist compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 10 mg to about 500 mg, preferably from about 25 mg to about 300 mg, more preferably from about 50 mg to about 250 mg, and most preferably from about 55 mg to about 200 mg, according to the particular application.

The actual dosage of CCR5 compound employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the CCR5 compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 100 mg/day to about 300 mg/day, preferably 150 mg/day to 250 mg/day, more preferably about 200 mg/day, in two to four divided doses.

The doses and dosage regimens of the NRTIs, NNRTIs, PIs and other agents used in combination with the CCR5 antagonists will be determined by the attending clinician inview of the approved doses and dosage regimens in the package inserts or as set forth in the protocols, taking into consideration the age, sex and condition of the patient and the severity of the condition treated.

The goal of the HIV-1 therapy of the present invention is to reduce the HIV-1-RNA viral load below the detectable limit. The "detectable limit of HIV-1-RNA" in the context of the present invention means that there are fewer than about 200 to fewer than about 50 copies of HIV-1-RNA per ml of plasma of the patient as measured by quantitative, multi-cycle reverse transcriptase PCR methodology. HIV-1-RNA is preferably measured in the present invention by the methodology of Amplicor-1 Monitor 1.5 (available from Roche Diagnsotics) or of Nuclisens HIV-1 QT-1.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound represented by the structural formula II

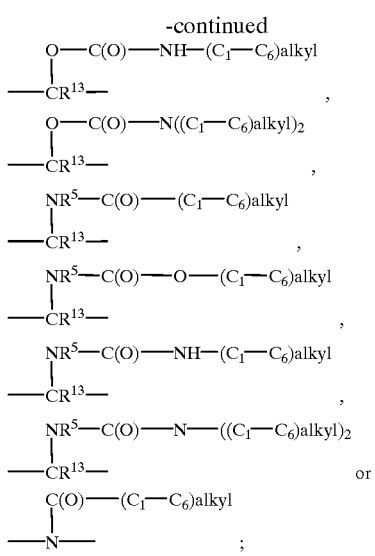

or a pharmaceutically acceptable salt thereof, wherein (1) $X^a$ is —C($R^{13}$)$_2$—, —C($R^{13}$)($R^{19}$)—, —C(O)—, —O—, —NH—, —N(($C_1$-$C_6$)alkyl)—,

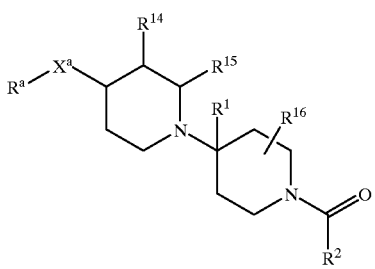

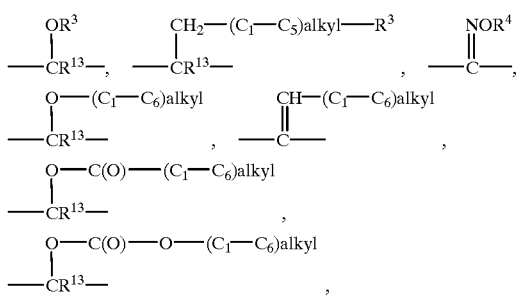

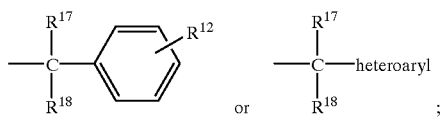

$R^a$ is $R^{6a}$-phenyl, $R^{6a}$-pyridyl, $R^{6a}$-thiophenyl or $R^6$-naphthyl;

$R^1$ is hydrogen, $C_1$-$C_6$ alkyl or $C_2$-$C_6$ alkenyl;

$R^2$ is $R^7$, $R^8$, $R^9$-phenyl; $R^7$, $R^8$, $R^9$-substituted 6-membered heteroaryl; $R^7$, $R^8$, $R^9$-substituted 6-membered heteroaryl N-oxide; $R^{10}$, $R^{11}$-substituted 5-membered heteroaryl; naphthyl; fluorenyl; diphenylmethyl

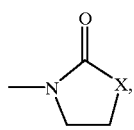

$R^3$ is $R^{10}$-phenyl, pyridyl, pyrimidyl, pyrazinyl or thiazolyl;

$R^4$ is hydrogen, $C_1$-$C_6$ alkyl, fluoro-$C_1$-$C_6$ alkyl, cyclopropylmethyl, —CH$_2$CH$_2$OH, —CH$_2$CH$_2$—O—($C_1$-$C_6$)alkyl, —CH$_2$C(O)—O—($C_1$-$C_6$)alkyl, —CH$_2$C(O)NH$_2$, —CH$_2$C(O)—NH($C_1$-$C_6$)alkyl or —CH$_2$C(O)—N(($C_1$-$C_6$)alkyl)$_2$;

$R^5$ and $R^{11}$ are independently selected from the group consisting of hydrogen and ($C_1$-$C_6$)-alkyl;

$R^{6a}$ is 1 to 3 substituents independently selected from the group consisting of hydrogen, halogen, —CF$_3$, CF$_3$O—, —CN, —CF$_3$SO$_2$—, —NHCOCF$_3$, 5-membered heteroaryl and wherein X is —O—, —NH— or —N(CH$_3$)—;

$R^6$ is independently selected from the group consisting of $R^{6a}$ and CH$_3$SO$_2$—;

$R^7$ and $R^8$ are independently selected from the group consisting of ($C_1$-$C_6$)alkyl, halogen, —NR$^{20}$R$^{21}$, —OH, —CF$_3$, —OCH$_3$, —O-acyl, and —OCF$_3$;

$R^9$ is $R^7$, hydrogen, phenyl, —NO$_2$, —CN, —CH$_2$F, —CHF$_2$, —CHO, —CH=NOR$^{20}$, pyridyl, pyridyl N-oxide, pyrimidinyl, pyrazinyl, —N($R^{20}$)
CON$R^{21}R^{22}$, —NHCONH(chloro-($C_1$-$C_6$)alkyl),
—NHCONH(($C_3$-$C_{10}$)-cycloalkyl($C_1$-$C_6$)alkyl),
—NHCO($C_1$-$C_6$)alkyl, —NHCOCF$_3$, —NHSO$_2$N
(($C_1$-$C_6$)alkyl)$_2$, —NHSO$_2$($C_1$-$C_6$)alkyl,
—N(SO$_2$CF$_3$)$_2$, —NHCO$_2$($C_1$-$C_6$)alkyl, $C_3$-$C_{10}$
cycloalkyl, —S$R^{23}$, —SO$R^{23}$, —SO$_2$$R^{23}$, —SO$_2$NH
($C_1$-$C_6$ alkyl), —OSO$_2$($C_1$-$C_6$)alkyl, —OSO$_2$CF$_3$,
hydroxy($C_1$-$C_6$)alkyl, —CON $R^{20}R^{21}$, —CON
(CH$_2$CH$_2$—O—CH$_3$)$_2$, —OCONH($C_1$-$C_6$)alkyl,
—CO$_2$$R^{20}$, —Si(CH$_3$)$_3$ or —B(OC(CH$_3$)$_2$)$_2$;

$R^{10}$ is ($C_1$-$C_6$)alkyl, —NH$_2$ or $R^{12}$-phenyl;

$R^{12}$ is 1 to 3 substituents independently selected from the group consisting of hydrogen, ($C_1$-$C_6$) alkyl, —CF$_3$, —CO$_2R_{20}$, —CN, ($C_1$-$C_6$)alkoxy and halogen;

$R^{13}$, $R^{14}$, $R^{15}$ and $R^{16}$ are independently selected from the group consisting of hydrogen and ($C_1$-$C_6$)alkyl;

$R^{17}$ and $R^{18}$ are independently selected from the group consisting of hydrogen and $C_1$-$C_6$ alkyl, or $R^{17}$ and $R^{18}$ together are a $C_2$-$C_5$ alkylene group and with the carbon to which they are attached form a spiro ring of 3 to 6 carbon atoms;

$R^{19}$ is $R^6$-phenyl, $R^6$-heteroaryl, $R^6$-naphthyl, $C_3$-$C_{10}$ cycloalkyl, ($C_3$-$C_{10}$)cycloalkyl($C_1$-$C_6$)alkyl or ($C_1$-$C_6$)alkoxy($C_1$-$C_6$)alkyl;

$R^{20}$, $R^{21}$ and $R^{22}$ are independently selected from the group consisting of H and $C_1$-$C_6$ alkyl; and $R^{23}$ is $C_1$-$C_6$ alkyl or phenyl; or (2): $X^a$ is —C($R^{13}$)($R^{19}$)—, —C(O)—, —O—, —NH—, —N(($C_1$-$C_6$)alkyl)—,

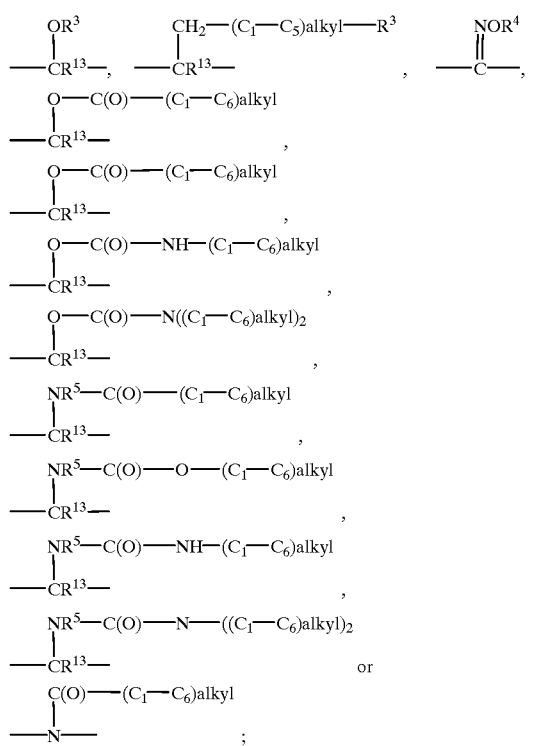

$R^a$ is $R^{6b}$-phenyl, $R^{6b}$-pyridyl or $R^{6b}$-thiophenyl;

$R^{4a}$ is fluoro-$C_1$-$C_6$ alkyl, cyclopropylmethyl, —CH$_2$CH$_2$OH, —CH$_2$CH$_2$—O—($C_1$-$C_6$)alkyl, —CH$_2$C(O)—O—($C_1$-$C_6$)alkyl, —CH$_2$C(O)NH$_2$, —CH$_2$C(O)—NH—($C_1$-$C_6$)alkyl or —CH$_2$C(O)—N(($C_1$-$C_6$)alkyl)$_2$;

$R^{6b}$ is CH$_3$SO$_2$—; and $R^1$, $R^2$, $R^3$, $R^5$, $R^{14}$, $R^{15}$, $R^{16}$ and $R^{19}$ are as defined in (1).

2. A compound of claim 1 wherein $R^a$ is

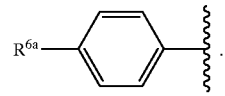

3. A compound of claim 1, formula II(1), wherein $X^a$ is —CHO$R^3$, —C($R^{13}$)($R^{19}$)— or —C(=NO$R^4$)—.

4. A compound of claim 3 wherein $R^3$ is pyridyl, $R^4$ is ($C_1$-$C_6$)alkyl, or $R^{13}$ is hydrogen and $R^{19}$ is $R^6$-phenyl.

5. A compound of claim 1, formula II(2), wherein $X^a$ is —CHO$R^3$, —C($R^{13}$)($R^{19}$)— or —C(=NO$R^{4a}$)—.

6. A compound of claim 5 wherein $R^3$ is pyridyl, $R^{4a}$ is cyclopropylmethyl or trifluoroethyl, or $R^{13}$ is hydrogen and $R^{19}$ is $R^6$-phenyl.

7. A compound of claim 1 wherein $R^2$ is $R^7$, $R^8$, $R^9$-phenyl; $R^7$, $R^8$, $R^9$-pyridyl or an N-oxide thereof; or $R^7$, $R^8$, $R^9$-pyrimidyl.

8. A compound of claim 7 wherein $R^2$ is selected from the group consisting of

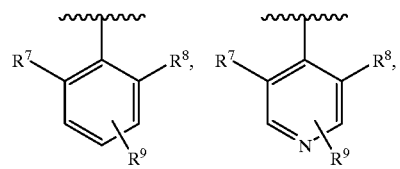

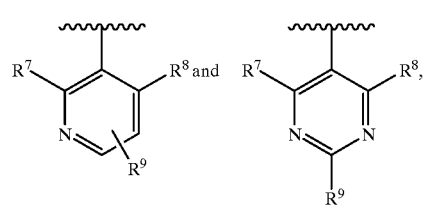

wherein $R^7$ and $R^8$ are selected from the group consisting of ($C_1$-$C_6$)alkyl, halogen, and —NH$_2$, and $R^9$ is hydrogen.

9. A compound selected from the group consisting of those represented by the formula

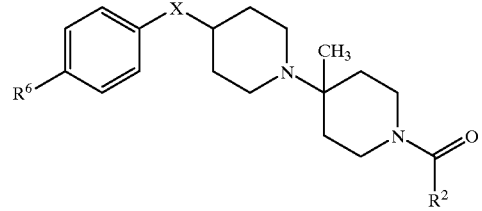

wherein $R^6$, X and $R^2$ are as defined in the following table:

| R⁶ | X | R² |
|---|---|---|
| Br | 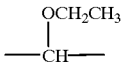 | 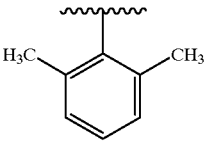 |
| Br | 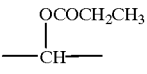 | 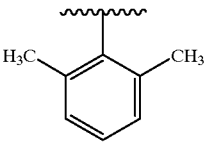 |
| Br | 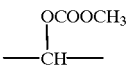 | 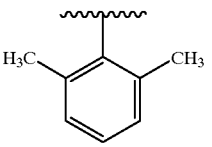 |
| Br | 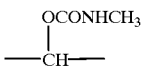 | 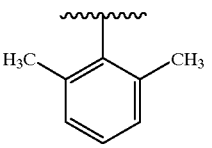 |
| Br | 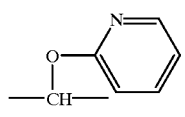 | 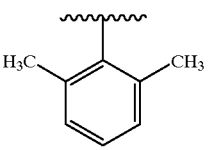 |
| Br | 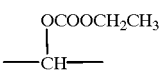 | 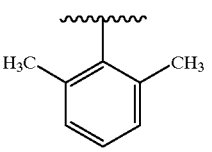 |
| Br | 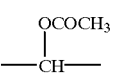 | 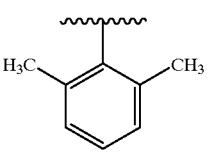 |
| Br | 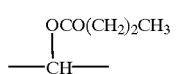 | 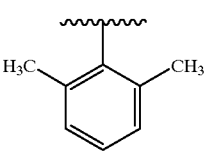 |
| Br | 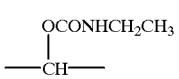 | 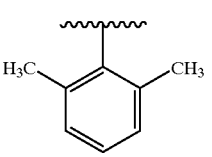 |

-continued

| R⁶ | X | R² |
|---|---|---|
| Br | 2-thiazolyl-O-CH- | 2,6-dimethylphenyl |
| Br | 2-pyrimidinyl-O-CH- | 2,6-dimethylphenyl |
| Br | 2-pyrazinyl-O-CH- | 2,6-dimethylphenyl |
| CH₃SO₂— | 2-pyridyl-O-CH- | 2,4-dimethylpyridin-3-yl |
| Br | 2-pyridyl-O-CH- | 2-amino-6-chlorophenyl |
| Br | 2-pyridyl-O-CH- | 2-hydroxy-6-methylphenyl |
| Br | 2-pyridyl-O-CH- | 2,4-dimethylpyridin-3-yl |
| Br | 2-pyridyl-O-CH- | 2-amino-6-methylphenyl |
| H₃CSO₂— | 2-pyridyl-O-CH- | 2-amino-6-chlorophenyl |

-continued
| R⁶ | X | R² |
|---|---|---|
| H₃CSO₂— | 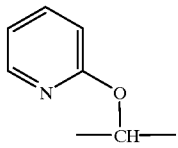 | 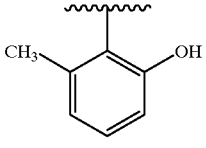 |
| F₃C— | 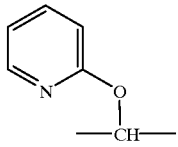 | 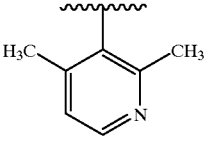 |
| H₃CSO₂— | 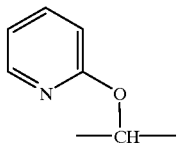 | 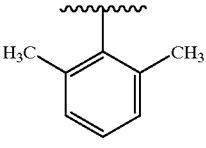 |
| H₃CSO₂— | 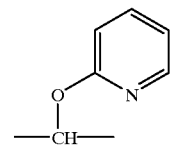 | 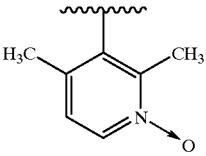 |
| F₃CO— | 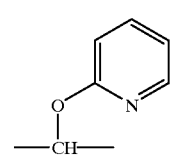 | 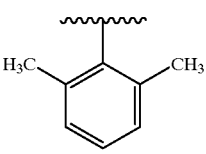 |
| F₃CO— | 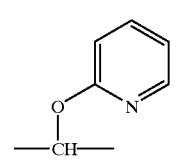 | 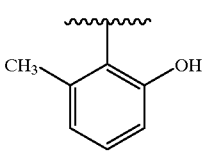 |
| F₃CO— | 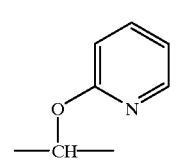 | 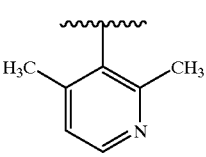 |
| Br | 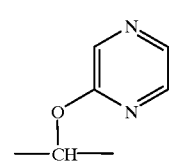 | 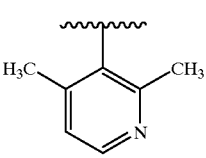 |
| Br | 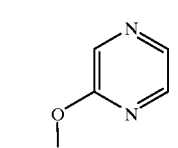 | 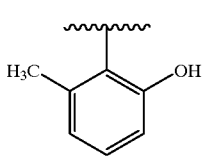 |

-continued

| R⁶ | X | R² |
|---|---|---|
| F₃CO— | 2-pyridyl-O-CH< | 2,4-dimethylpyridin-3-yl N-oxide |
| Br | 2-pyridyl-O-CH< | 2,4-dimethylpyridin-3-yl N-oxide |
| Br | 2-pyrazinyl-O-CH< | 2,4-dimethylpyridin-3-yl N-oxide |
| H₃CSO₂— | 2-pyridyl-O-CH< | 4,6-dimethylpyrimidin-5-yl |
| H₃CSO₂— | 2-pyrazinyl-O-CH< | 2,4-dimethylpyridin-3-yl |
| H₃CSO₂— | 2-pyrazinyl-O-CH< | 2,4-dimethylpyridin-3-yl N-oxide |
| H₃CSO₂— | 2-thiazolyl-O-CH< | 2,4-dimethylpyridin-3-yl |
| H₃CSO₂— | phenyl-O-CH< | 2,4-dimethylpyridin-3-yl |
| H₃CSO₂— | 2-thiazolyl-O-CH< | 2,4-dimethylpyridin-3-yl N-oxide |

-continued
| R⁶ | X | R² |
|---|---|---|
| F₃C— | 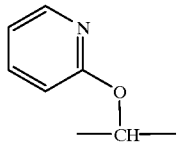 | 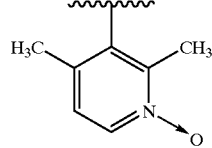 |
| F₃CO— | 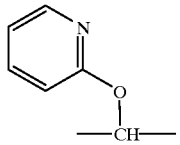 | 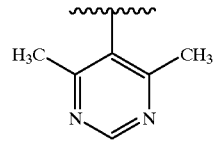 |
| F₃CO— | 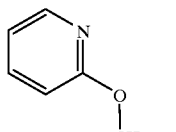 | 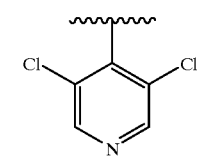 |
| Cl | 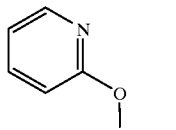 | 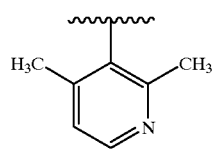 |
| Cl | 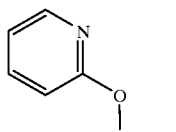 | 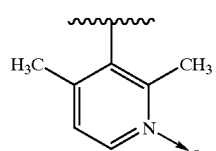 |
| Cl | 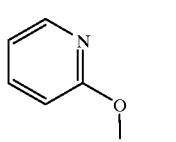 | 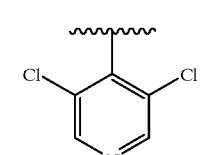 |
| Cl | 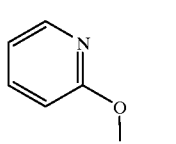 | 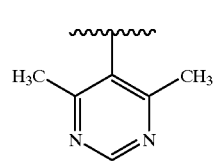 |
| Br | 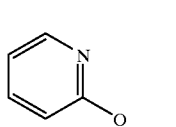 | 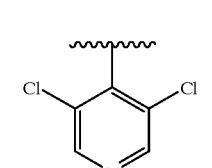 |
| H₃CSO₂— | 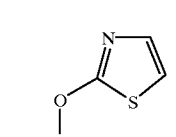 | 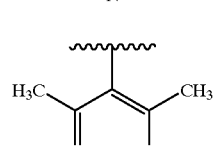 |

| R⁶ | X | R² |
|---|---|---|
| F₃C— | 2-pyridyl-O-CH— | 4,6-dimethylpyrimidin-5-yl |
| H₃CSO₂— | pyrazin-2-yl-O-CH— | 3,5-dichloropyridin-4-yl |
| H₃CSO₂— | pyrazin-2-yl-O-CH— | 4,6-dimethylpyrimidin-5-yl |
| F₃C— | 2-pyridyl-O-CH— | 3,5-dichloropyridin-4-yl |
| F | 2-pyridyl-O-CH— | 2,4-dimethylpyridin-3-yl |
| F | 2-pyridyl-O-CH— | 2,4-dimethylpyridin-3-yl N-oxide |
| F | 2-pyridyl-O-CH— | 4,6-dimethylpyrimidin-5-yl |
| Cl | 2-pyridyl-O-CH— | 3,5-dichloropyridin-4-yl N-oxide |

-continued
| R⁶ | X | R² |
|---|---|---|
| F | 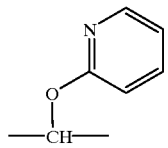 | 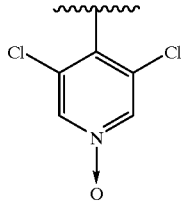 |
| Br | 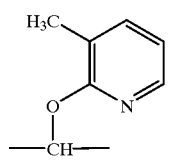 | 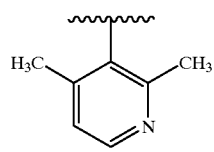 |
| Br | 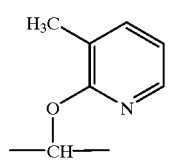 | 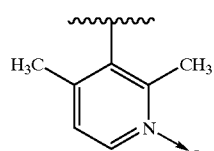 |
| Br | 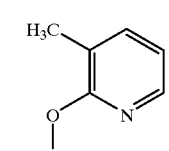 | 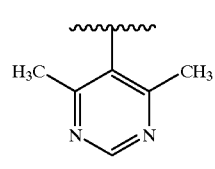 |
| Br | 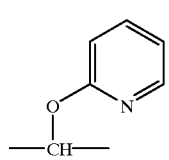 | 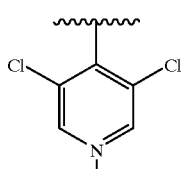 |
| F₃C— | 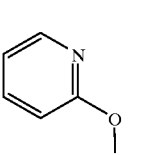 | 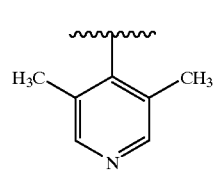 |
| F₃C— | 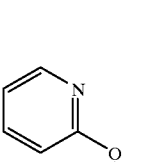 | 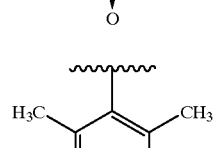 |
| F₃C— | | |

-continued
| R⁶ | X | R² |
|---|---|---|
| F | 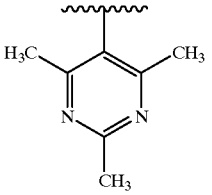 | 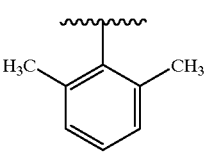 |
| Br | 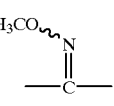 | 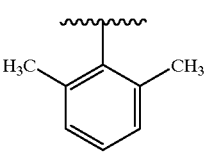 |
| Br | 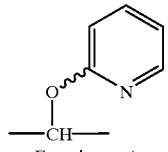 Enantiomer A | 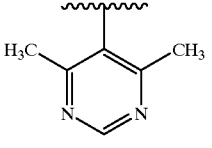 |
| Br | 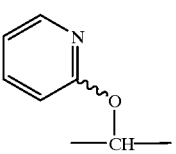 Enantiomer A | 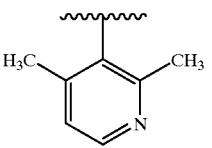 |
| Br | 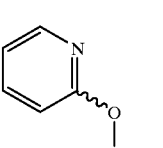 Enantiomer B | 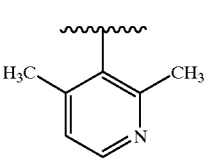 |
| Br | 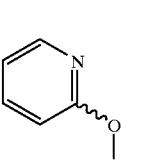 Enantiomer B | 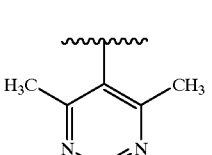 |
| F₃CO— | 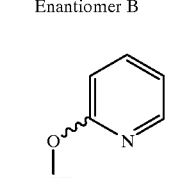 Enantiomer A | |
| F₃CO— | 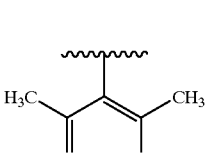 Enantiomer B | |

-continued
| R⁶ | X | R² |
|---|---|---|
| F₃CO— | 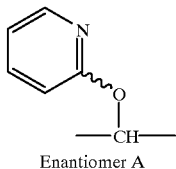<br>Enantiomer A | 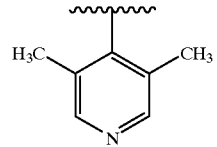 |
| F₃CO— | 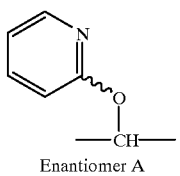<br>Enantiomer A | 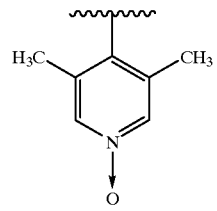 |
| F₃CO— | 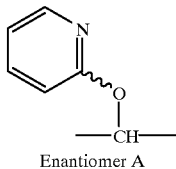<br>Enantiomer A | 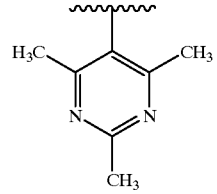 |
| F₃CO— | 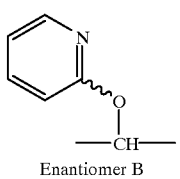<br>Enantiomer B | 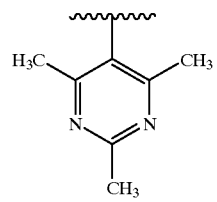 |
| Cl | 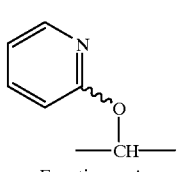<br>Enantiomer A | 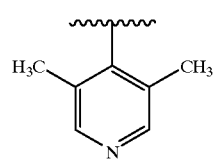 |
| Cl | 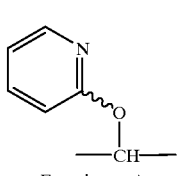<br>Enantiomer A | 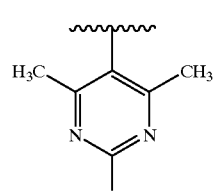 |
| Cl | 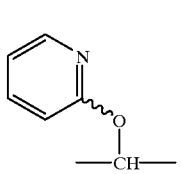<br>Enantiomer B | 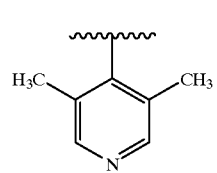 |

-continued

| R⁶ | X | R² |
|---|---|---|
| Cl | pyridyl-O-CH- (Enantiomer B) | 4,6-dimethyl-2-methylpyrimidin-5-yl |
| F₃CO— | O-pyridyl-CH- (Enantiomer B) | 2-amino-4,6-dimethylpyrimidin-5-yl |
| Br | H₃CO-N=C- (Z-isomer) | 2,6-dimethylphenyl |
| Br | -C(=N-OCH₃)- (E-isomer) | 2,6-dimethylphenyl |
| Br | -C(=N-OCH₃)- (Mixture E/Z) | 2-amino-3-methylphenyl |
| Br | -C(=N-OCH₃)- (Mixture E/Z) | 2-amino-3-chlorophenyl |
| Br | CH₃CH₂O-N=C- | 2,6-dimethylphenyl |
| Br | -C(=N-OCH₃)- | 2-amino-3-chlorophenyl |
| Br | -C(=N-OCH₃)- | 2-amino-3-methylphenyl |

-continued

| R⁶ | X | R² |
|---|---|---|
| Br | H₃CO-N=C (methoxyimino) | 2-methyl-6-hydroxyphenyl (H₃C, OH) |
| Br | H₃CO-N=C (methoxyimino) | 2-methyl-6-aminophenyl (H₃C, NH₂) |
| Br | CH₃CH₂O-N=C (ethoxyimino) | 2-methyl-6-hydroxyphenyl (H₃C, OH) |
| Br | CH₃CH₂O-N=C (ethoxyimino) | 2,4-dimethylpyridin-3-yl (H₃C, CH₃) |
| Br | H₃CO-N=C (methoxyimino) | 2,4-dimethylpyridin-3-yl (H₃C, CH₃) |
| Br | CH₃CH₂O-N=C (ethoxyimino) | 2,4-dimethylpyridin-3-yl N-oxide (H₃C, CH₃, N⁺–O⁻) |
| Br | H₃CO-N=C (methoxyimino) | 4,6-dimethylpyrimidin-5-yl (H₃C, CH₃) |
| Br | N-OCH₂CH₃ (E/Z ethoxyimino) | 2,4-dimethylpyridin-3-yl (H₃C, CH₃) |
| Br | CH₃CH₂O-N=C (ethoxyimino) | 4,6-dimethylpyrimidin-5-yl (H₃C, CH₃) |

-continued
| R⁶ | X | R² |
|---|---|---|
| Br | 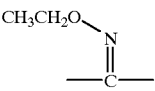 | 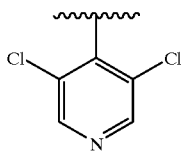 |
| Br | 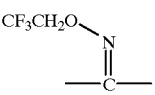 | 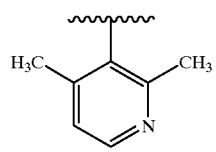 |
| Br | 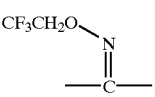 | 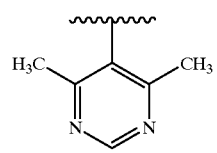 |
| Br | 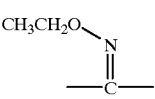 | 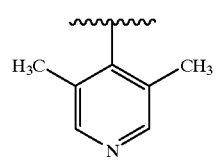 |
| Br | 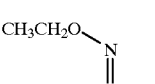 | 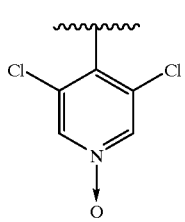 |
| Br | 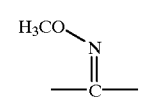 | 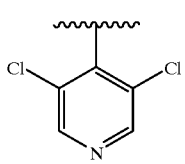 |
| Br | 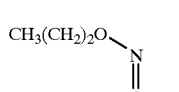 | 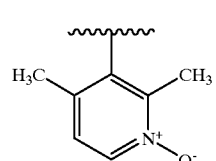 |
| Br | 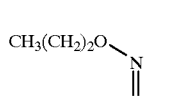 | 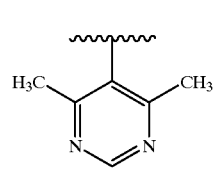 |

-continued
| R⁶ | X | R² |
|---|---|---|
| Br | 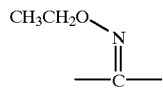 | 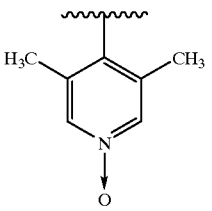 |
| Br | 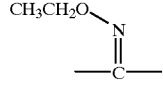 | 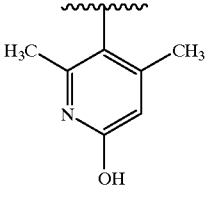 |
| Br | 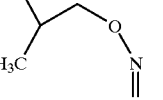 | 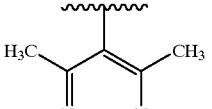 |
| Br | 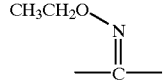 | 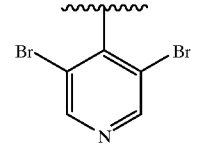 |
| Br | 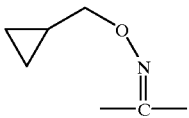 | 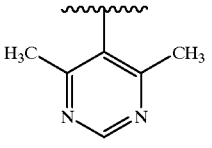 |
| Br | 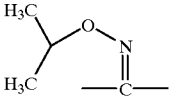 | 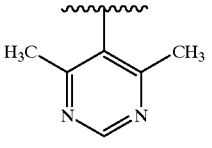 |
| Br | 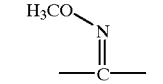 | 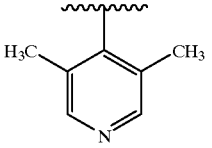 |
| Br | 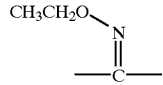 | 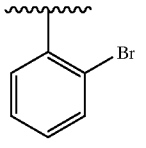 |

| R⁶ | X | R² |
|---|---|---|
| Br | CH₃CH₂O-N=C- | 3,5-dibromopyridin-4-yl N-oxide |
| Br | CH₃CH₂O-N=C- | 2,4,6-trimethylpyrimidin-5-yl |
| F₃C— | CH₃CH₂O-N=C- | 4,6-dimethylpyrimidin-5-yl |
| Br | CH₃CH₂O-N=C- | 5-methyl-3-phenylisoxazol-4-yl |
| Br | CH₃CH₂O-N=C- | 4,6-dimethyl-2-methylthiopyrimidin-5-yl |
| Br | CH₃CH₂O-N=C- | 3-(2-chlorophenyl)-5-methylisoxazol-4-yl |
| Br | CH₃CH₂O-N=C- | 2,6-dimethyl-4-hydroxyphenyl |

-continued
| R⁶ | X | R² |
|---|---|---|
| Br | 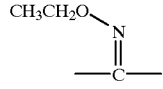 | 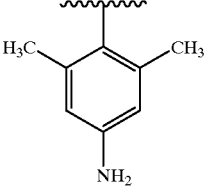 |
| Br | 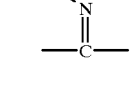 | 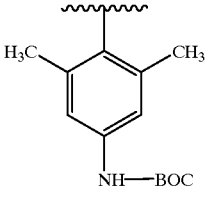 |
| Br | 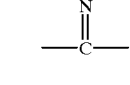 | 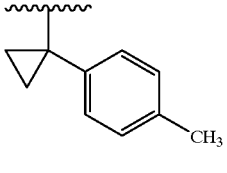 |
| Br | 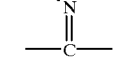 | 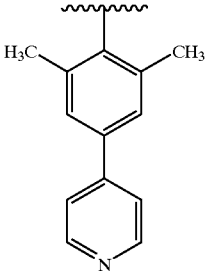 |
| Br | 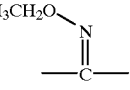 | 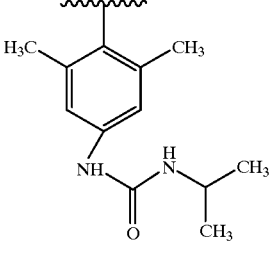 |
| F₃CO— | 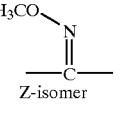 Z-isomer | 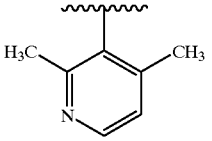 |
| F₃CO— | 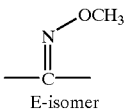 E-isomer | 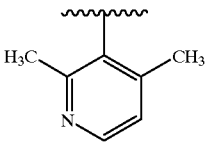 |

-continued
| R⁶ | X | R² |
|---|---|---|
| Br | 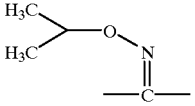 | 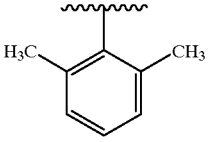 |
| Br | 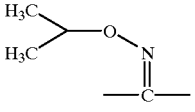 | 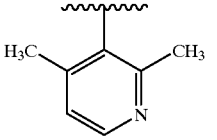 |
| Br | 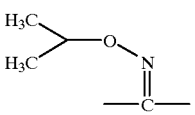 | 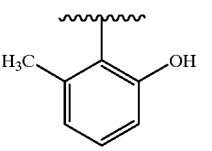 |
| Br | 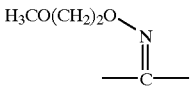 | 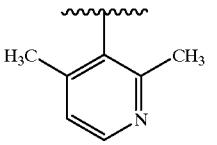 |
| Br | 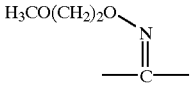 | 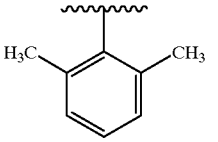 |
| Br | 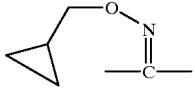 | 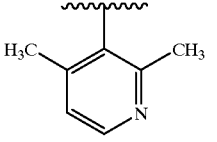 |
| F₃CO— | 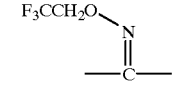 | 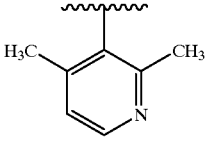 |
| F₃CO— | 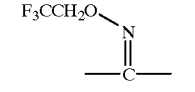 | 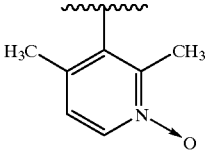 |
| F₃CO— | 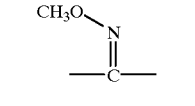 | 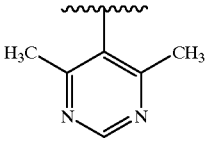 |

-continued

| R⁶ | X | R² |
|---|---|---|
| F₃CO— | F₃CCH₂O-N=C | 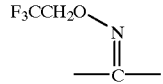 3-methyl-phenol with OH |
| F₃CO— | F₃CCH₂O-N=C | 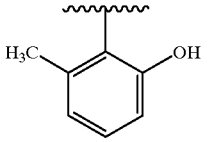 4,6-dimethylpyrimidine |
| F₃CO— | cyclopropyl-CH₂-O-N=C | 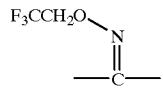 2,4-dimethylpyridine N-oxide |
| Cl | CH₃CH₂O-N=C | 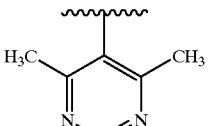 3,5-dimethylpyridine N-oxide |
| Cl | CH₃O-N=C | 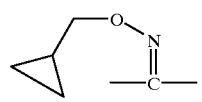 2,4-dimethylpyridine |
| F₃C— | CH₃O-N=C | 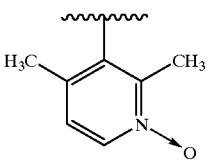 2,4-dimethylpyridine N-oxide |
| Cl | CH₃CH₂O-N=C | 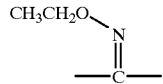 2,4-dimethylpyridine |
| Cl | CH₃CH₂O-N=C | 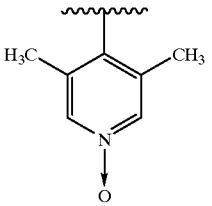 2,5-dimethylpyridine N-oxide |
| Cl | CH₃CH₂O-N=C | 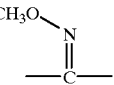 4,6-dimethylpyrimidine |

-continued
| R⁶ | X | R² |
|---|---|---|
| F₃C— | 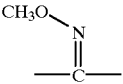 | 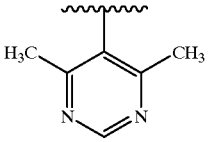 |
| Cl | 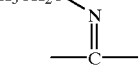 | 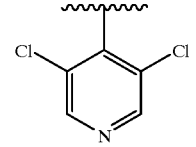 |
| F₃C— | 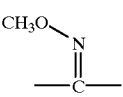 | 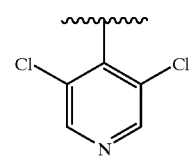 |
| F₃C— | 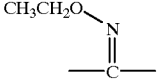 | 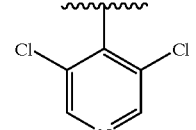 |
| Cl | 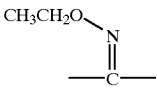 | 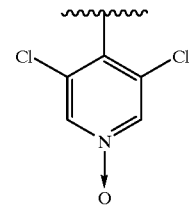 |
| Cl | 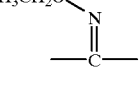 | 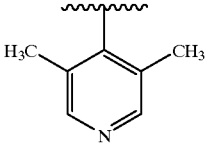 |
| F₃CO— | 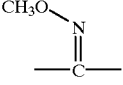 | 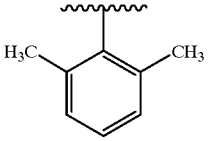 |
| F₃CO— | 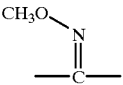 | 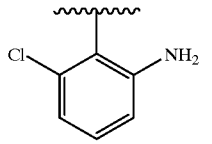 |
| F₃CO— | 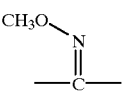 | 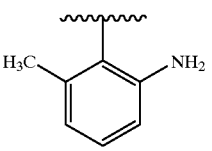 |

-continued

| $R^6$ | X | $R^2$ |
|---|---|---|
| $F_3CO-$ | $CH_3CH_2O-N=C$ | 2,6-dimethylphenyl |
| $F_3C-$ | $CH_3O-N=C$ | 2,6-dimethylphenyl |
| $F_3CO-$ | $CH_3O-N=C$ | 2-methyl-6-hydroxyphenyl |
| $F_3C-$ | $CH_3O-N=C$ (E isomer) | 2-chloro-6-aminophenyl |
| $F_3C-$ | $CH_3O-N=C$ | 2-chloro-6-aminophenyl |
| $F_3C-$ | $CH_3O-N=C$ | 2-methyl-6-aminophenyl |
| $F_3CO-$ | $CH_3CH_2O-N=C$ | 2-chloro-6-aminophenyl |
| $F_3C-$ | $CH_3O-N=C$ | 2,4-dimethylpyridin-3-yl |
| $F_3C-$ | $CH_3CH_2O-N=C$ | 2-methyl-6-hydroxyphenyl |

-continued
| R⁶ | X | R² |
|---|---|---|
| F₃CO— |  | 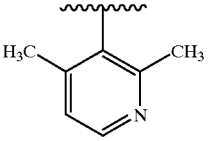 |
| F₃CO— | 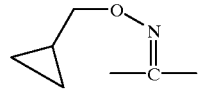 | 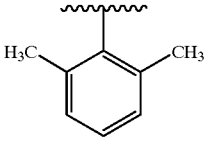 |
| F₃CO— |  | 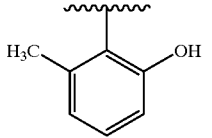 |
| F₃C— | <br>E isomer | 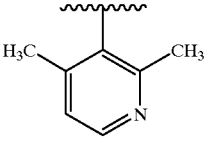 |
| F₃CO— |  | 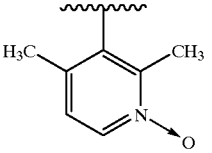 |
| F₃CO— | 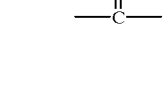 | 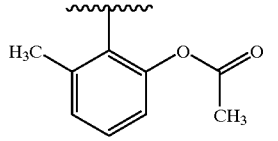 |
| F₃C— | 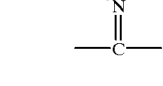 | 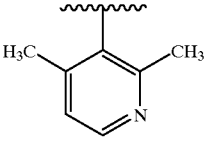 |
| F₃C— | 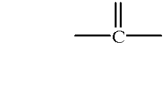 | 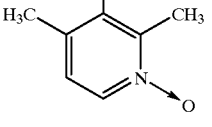 |
| F₃CO— | <br>E isomer | 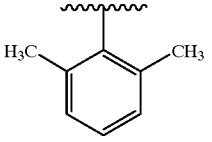 |

-continued

| R⁶ | X | R² |
|---|---|---|
| F₃CO— | H₃CO(CH₂)₂O—N=C | 2,6-dimethylphenyl |
| F₃CO— | CH₃CH₂O—N=C | 2,4-dimethylpyridin-3-yl N-oxide |
| F₃CO— | cyclopropylmethyl-O—N=C | 2,4-dimethylpyridin-3-yl |
| F₃CO— | cyclopropylmethyl-O—N=C | 2-methyl-6-hydroxyphenyl (H₃C, OH) |
| F₃CO— | CH₃CH₂O—N=C | 3,5-dichloropyridin-4-yl |
| F₃CO— | CH₃O—N=C | 3,5-dichloropyridin-4-yl |
| F₃CO— | CH₃CH₂O—N=C | 3,5-dichloropyridin-4-yl |
| F₃CO— | CH₃CH₂O—N=C | 4,6-dimethylpyrimidin-5-yl |
| F₃CO— | CH₃O—N=C | 3,5-dichloropyridin-4-yl N-oxide |

-continued

| R⁶ | X | R² |
|---|---|---|
| F₃CO— | CH₃CH₂O−N=C− | 3,5-dichloropyridin-4-yl N-oxide |
| F₃CO— | CH₃(CH₂)₂O−N=C− | 4,6-dimethylpyrimidin-5-yl |
| F₃CO— | CH₃(CH₂)₂O−N=C− | 3,5-dichloropyridin-4-yl N-oxide |
| F₃CO— | CH₃(CH₂)₂O−N=C− | 2,4-dimethylpyridin-3-yl N-oxide |
| Br | CH₃O−N=C− | 3-chloro-2-aminophenyl (with Cl and NH₂ substituents) |
| F₃C— | CH₃CH₂O−N=C− | 4,6-dimethylpyrimidin-5-yl |
| Br | —CH₂— | 3-(2-chlorophenyl)-5-methylisoxazol-4-yl |
| Br | —CH₂— | 5-methyl-3-phenylisoxazol-4-yl |

-continued

| R⁶ | X | R² |
|---|---|---|
| Br | —CH₂— | 3-methyl-5-amino-isoxazol-4-yl |
| Br | —CH₂— | 3-(2,6-dichlorophenyl)-5-methyl-isoxazol-4-yl |
| Br | —CH₂— | naphthalen-1-yl |
| Br | —CH₂— | 1-phenylcyclopropyl |
| Br | —CH(pyridin-3-yloxy)— | 4,6-dimethylpyrimidin-5-yl |
| CH₃SO₂— | —CH(phenoxy)— | 2,4-dimethylpyridin-3-yl N-oxide |
| Br | —CH(pyridin-3-yloxy)— | 2,4-dimethylpyridin-3-yl |
| Br | —CH(4-fluorophenoxy)— | 4,6-dimethylpyrimidin-5-yl |
| F | —CH(phenoxy)— | 4,6-dimethylpyrimidin-5-yl |

-continued

| R⁶ | X | R² |
|---|---|---|
| F | phenyl-O-CH (benzyloxy via CH) | 2,4-dimethylpyridin-3-yl |
| F | phenyl-O-CH | 2,4-dimethylpyridin-3-yl N-oxide |
| Br | 3-fluorophenyl-O-CH | 4,6-dimethylpyrimidin-5-yl |
| Cl | 3-chlorophenyl-O-CH | 4,6-dimethylpyrimidin-5-yl |
| F₃C— | phenyl-O-CH | 2,4-dimethylpyridin-3-yl N-oxide |
| CH₃SO₂— | phenyl-O-CH | 4,6-dimethylpyrimidin-5-yl |
| CH₃SO₂— | 2-fluorophenyl-O-CH | 4,6-dimethylpyrimidin-5-yl |
| F₃CO— | 3-fluorophenyl-O-CH | 4,6-dimethylpyrimidin-5-yl |
| F₃CO— | 3-chlorophenyl-O-CH | 4,6-dimethylpyrimidin-5-yl |

-continued
| R⁶ | X | R² |
|---|---|---|
| CH₃SO₂— | 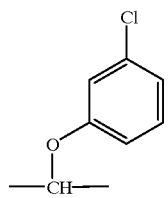 | 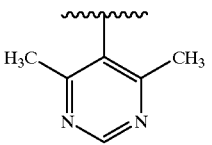 |
| CH₃SO₂— | 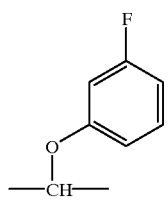 | 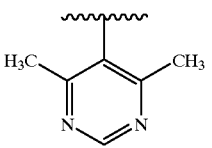 |
| F₃C— | 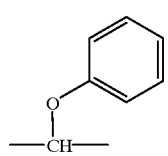 | 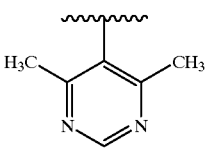 |
| F₃CO— | 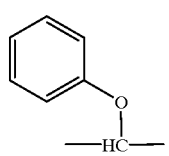 | 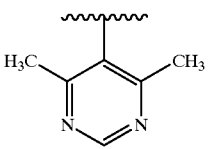 |
| F₃CO— | 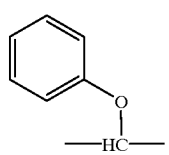 | 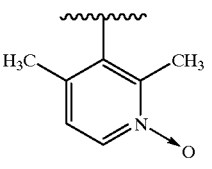 |
| F₃C— | 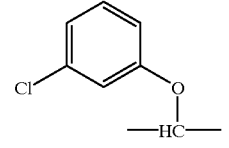 | 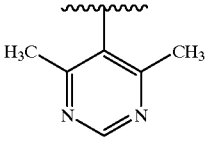 |
| H | 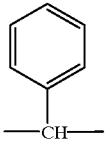 | 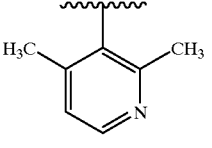 |
| F₃CO— | 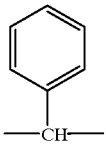 | 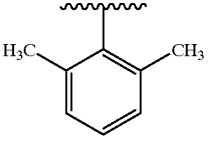 |

-continued
| R⁶ | X | R² |
|---|---|---|
| F₃CO— | 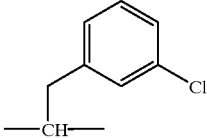 | 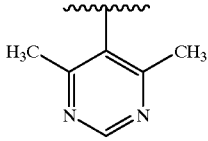 |
| F₃CO— | 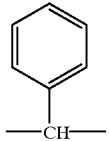 | 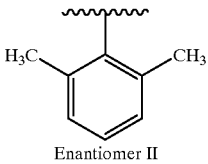<br>Enantiomer II |
| F₃CO— | 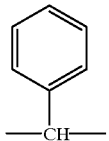 | 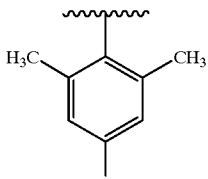<br>Enantiomer II |
| F₃CO— | 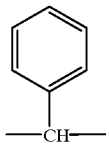 | 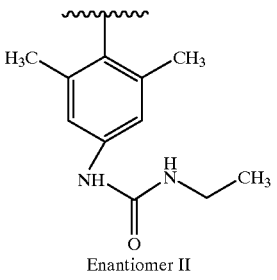<br>Enantiomer II |
| CH₃SO₂— | 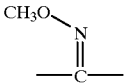 | 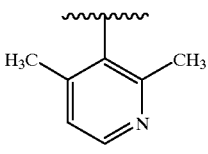 |
| CH₃SO₂— | 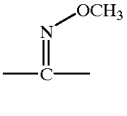 | 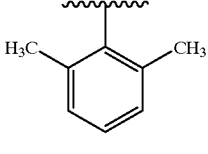 |
| CH₃SO₂— | 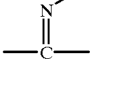 | 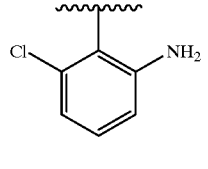 |
| CH₃SO₂— | 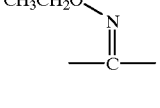 | 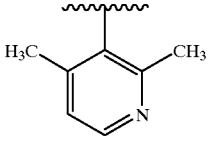 |

-continued

| R⁶ | X | R² |
|---|---|---|
| CH₃SO₂— | CH₃CH₂O−N=C− | 2,4-dimethylpyridin-3-yl N-oxide |
| CH₃SO₂— | CH₃O−N=C− | 2,4-dimethylpyridin-3-yl |
| CH₃SO₂— | CH₃O−N=C− | 2,4-dimethylpyridin-3-yl N-oxide |
| CH₃SO₂— | CH₃O−N=C− | 4,6-dimethylpyrimidin-5-yl |

10. A pharmaceutical composition comprising an effective amount of a CCR5 antagonist of claim 1 in combination with a pharmaceutically acceptable carrier.

11. A method of treating Human Immunodeficiency Virus comprising administering to a human in need of such treatment a therapeutically effective amount of a CCR5 antagonist of claim 1.

12.

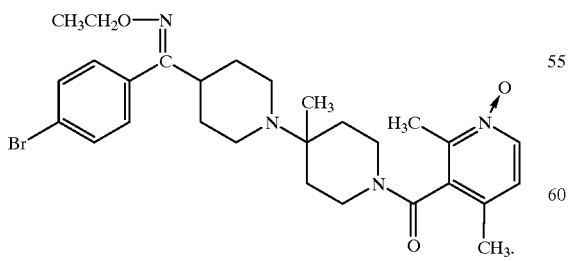

13.

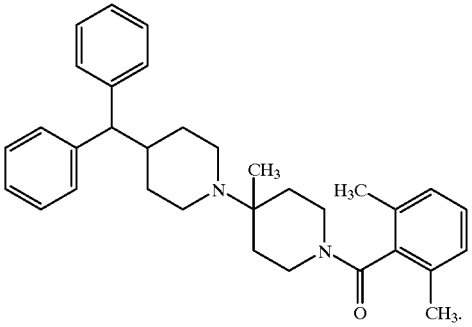

14.

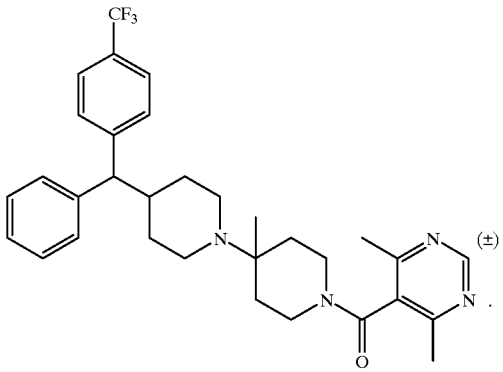

* * * * *

UNITED STATES PATENT AND TRADEMARK OFFICE
CERTIFICATE OF CORRECTION

PATENT NO.     : 6,387,930 B1
DATED          : May 14, 2002
INVENTOR(S)    : Bahige M. Baroudy et al.

It is certified that error appears in the above-identified patent and that said Letters Patent is hereby corrected as shown below:

<u>Title page,</u>
Item [75], delete "Mark A. Laughlin, Edison".

Signed and Sealed this

Sixth Day of May, 2003

JAMES E. ROGAN
*Director of the United States Patent and Trademark Office*